(12) United States Patent
Niederwerder

(10) Patent No.: US 11,612,623 B2
(45) Date of Patent: Mar. 28, 2023

(54) MICROBIOME TRANSPLANTATION

(71) Applicant: Kansas State University Research Foundation, Manhattan, KS (US)

(72) Inventor: Megan C. Niederwerder, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 54 days.

(21) Appl. No.: 16/692,411

(22) Filed: Nov. 22, 2019

(65) Prior Publication Data

US 2020/0078419 A1 Mar. 12, 2020

Related U.S. Application Data

(63) Continuation-in-part of application No. PCT/US2018/033910, filed on May 22, 2018.
(Continued)

(51) Int. Cl.
*A61K 35/745* (2015.01)
*A23K 50/30* (2016.01)
(Continued)

(52) U.S. Cl.
CPC ............ *A61K 35/745* (2013.01); *A23K 10/18* (2016.05); *A23K 50/30* (2016.05); *A61K 9/0053* (2013.01); *A61K 2035/115* (2013.01)

(58) Field of Classification Search
CPC ............ A61K 2300/00; A61K 2039/58; A61K 39/0011; A61K 31/19; A61K 31/375; A61K 31/59; A61K 33/30; A61K 38/19; A61K 38/446; A61K 9/0053; A61K 39/02; A61K 39/35; A61K 45/06; A61K 2039/521; A61K 9/14; A61K 35/745; A61K 35/747; A61K 39/0008; A61K 39/04; A61K 39/39; A61K 2039/505; A61K 2039/55516; A61K 2039/55572; A61K 31/407; A61K 31/421; A61K 31/4965; A61K 31/65; A61K 38/465; A61K 38/47; A61K 38/482; A61K 38/4826; A61K 38/4873; A61K 39/015; A61K 39/12; A61K 39/395; A61K 9/12; A61K 2035/11; A61K 2039/5252; A61K 2039/585; A61K 31/295; A61K 31/733; A61K 35/12; A61K 35/36; A61K 35/37; A61K 9/0031; A61K 9/0078; A61K 2039/52; A61K 2039/542; A61K 2039/545; A61K 2039/70; A61K 31/726; A61K 35/741; A61K 35/744; A61K 38/54; A61K 39/0258; A61K 39/0266; A61K 39/0275; A61K 39/05; A61K 39/085; A61K 39/092; A61K 39/095; A61K 39/102; A61K 47/10; A61K 9/0043; A61K 9/08; A61K 9/48; A61K 2035/115; A61K 2039/5254; A61K 2039/55594; A61K 35/00; A61K 35/742; A61K 35/76; A61K 36/062; A61K 38/1729; A61K 39/00; A61K 39/1045; A61K 39/145; A61K 9/0014; Y02A 50/30; Y02A 50/385; Y02A 50/475; Y02A 50/481; A61P 11/00; A61P 1/00; A61P 31/00; A61P 31/04; A61P 1/14; A61P 37/04; A61P 35/00; A61P 37/02; A61P 43/00; A61P 17/00; A61P 1/04; A61P 29/00; A61P 37/00; A61P 37/08; A61P 39/00; A61P 3/00; A61P 7/00; A61P 11/02; A61P 11/08; A61P 19/02; A61P 1/02; A61P 1/12; A61P 25/30; A61P 25/32; A61P 31/06; A61P 31/14; A61P 31/16; A61P 3/02; A61P 9/00; A23K 50/30; A23K 20/30; A23K 50/10; A23K 50/75; A23K 20/10; A23K 10/18; A23K 20/105; A23K 20/142; A23K 20/158; A23K 20/174; A23K 20/179; A23K 20/189; A23K 20/195; A61M 16/0666; A61M 16/14; A61M 16/208; A61M 11/002; A61M 11/003; A61M 11/005; A61M 11/06; A61M 15/0085; A61M 15/0086; A61M 15/025; A61M 16/0057; A61M 16/0672; A61M 2202/0275; A61M 2205/33; A61M 2205/52; A61M 2206/14; A61M 2206/16; A61M 16/0683;
(Continued)

(56) References Cited

U.S. PATENT DOCUMENTS

| | | | |
|---|---|---|---|
| 6,962,718 B2 * | 11/2005 | Ramaekers ............ | A61K 33/30 424/535 |
| 7,427,397 B2 * | 9/2008 | Adams ................... | A61P 37/04 424/93.4 |

(Continued)

OTHER PUBLICATIONS

Hong et al, "The use of bacterial spore formers as probioitics", FEMS Microbio. Rev. 29(2005) pp. 813-835. (Year: 2005).*
(Continued)

*Primary Examiner* — David W Berke-Schlessel
(74) *Attorney, Agent, or Firm* — Tracey S. Truitt; Armstrong Teasdale LLP

(57) ABSTRACT

The present disclosure provides compositions and methods for improving disease resistance, increasing weight gain, and reducing the incidence and/or severity of clinical signs of infection. The composition generally comprises one or more microorganisms that is administered to an animal in need thereof. Preferred infections that can be combated with the compositions and methods of this disclosure are respiratory infections including PRRSV and PCV2.

17 Claims, 25 Drawing Sheets

Specification includes a Sequence Listing.

Related U.S. Application Data

(60) Provisional application No. 62/509,731, filed on May 22, 2017, provisional application No. 62/587,240, filed on Nov. 16, 2017.

(51) Int. Cl.
*A23K 10/18* (2016.01)
*A61K 9/00* (2006.01)
*A61K 35/00* (2006.01)

(58) Field of Classification Search
CPC .......... A61M 16/0808; A61M 16/1095; A61M 2205/3368; C12N 2760/16134; C12N 15/113; C12N 2310/14; C12N 2710/10343; C12N 2730/10134; C12N 2760/16234; C12N 2770/24234; C12N 7/00; C12N 15/1037; C12N 15/74; C12N 15/79; C12N 15/86; C12N 15/87; C12N 15/907; C12N 1/20; C12N 2770/10034; C12N 2795/10222; C12N 2795/10223; C12N 5/10; C12N 7/02; A23L 29/065; A23L 33/105; A23L 33/135; C12Y 304/21075; A01N 37/10; A01N 37/36; A01N 37/44; A01N 43/40; A01N 55/02; A01N 59/16; C09D 5/14; A23Y 2320/29; C07K 14/005; C07K 14/35; C07K 2319/31; C12R 1/01; G01N 2500/10; G01N 33/569; Y10S 514/867
See application file for complete search history.

(56) References Cited

U.S. PATENT DOCUMENTS

| | | | | |
|---|---|---|---|---|
| 8,945,605 B2* | 2/2015 | Boucher | .................. | A61K 9/12 424/434 |
| 8,980,279 B2* | 3/2015 | Gunn | ................. | A61K 39/0266 424/206.1 |
| 10,130,692 B2* | 11/2018 | Gunn | ................. | A61K 39/0258 |
| 10,272,141 B2* | 4/2019 | Fallon | .................... | A61K 38/47 |
| 10,369,205 B2* | 8/2019 | Agrawal | ................ | A61K 39/12 |
| 10,653,658 B2* | 5/2020 | Ala'Aldeen | ........... | A01N 55/02 |
| 10,668,118 B2* | 6/2020 | Lynch | ................... | A23L 29/065 |
| 10,716,835 B2* | 7/2020 | Fallon | .................... | A61P 31/16 |
| 2003/0077254 A1* | 4/2003 | Ramaekers | .......... | A61K 38/446 424/93.3 |
| 2006/0018890 A1* | 1/2006 | Isolauri | ................... | A61P 11/00 424/93.45 |
| 2006/0029585 A1* | 2/2006 | Ramaekers | ............ | A61K 38/19 424/93.45 |
| 2009/0280099 A1* | 11/2009 | Bachman | ................ | A61P 31/00 424/93.45 |
| 2014/0109899 A1* | 4/2014 | Boucher | ............... | A61M 16/14 128/200.18 |
| 2014/0158127 A1* | 6/2014 | Boucher | ............... | A61M 16/14 128/203.22 |
| 2015/0150803 A1* | 6/2015 | Boucher | ............... | A61K 38/482 128/200.16 |
| 2016/0317637 A1* | 11/2016 | Agrawal | ................ | A61K 39/02 |
| 2017/0304355 A1* | 10/2017 | Baker | ...................... | A61K 9/08 |

OTHER PUBLICATIONS

Schroeder, B; et al; "Preventive Effects of the Probiotic *Escherichia coli* Strain Nissle 1917 on Acute Secretory Diarrhea in a Pig Model of Intestinal Infection" Digestive Diseases and Sciences, 51, 724-731,2006 (Year: 2006).*

Mutaflor Package Leaflet; https://www.mutaflor.com/index.html (Year: 2000).*

Niederwerder, Megan C; et al; "Microbiome associations in pigs with the best and worst clinical outcomes following co-infection with porcine reproductive and respiratory syndrome virus (PRRSV) and porcine circovirus type 2(PCV2)" Veterinary Microbiology, 188, 1-11, 2016 (Year: 2016).*

Ober, Rebecca A; et al; "Increased microbiome diversity at the time of infection is associated with improved growth rates of pigs after co-infection with porcine reproductive and respiratory syndrome virus (PRRSV) and porcine circovirus type 2(PCV2)" Veterinary Microbiology, 208, 203-211, 2017 (Year: 2017).*

* cited by examiner

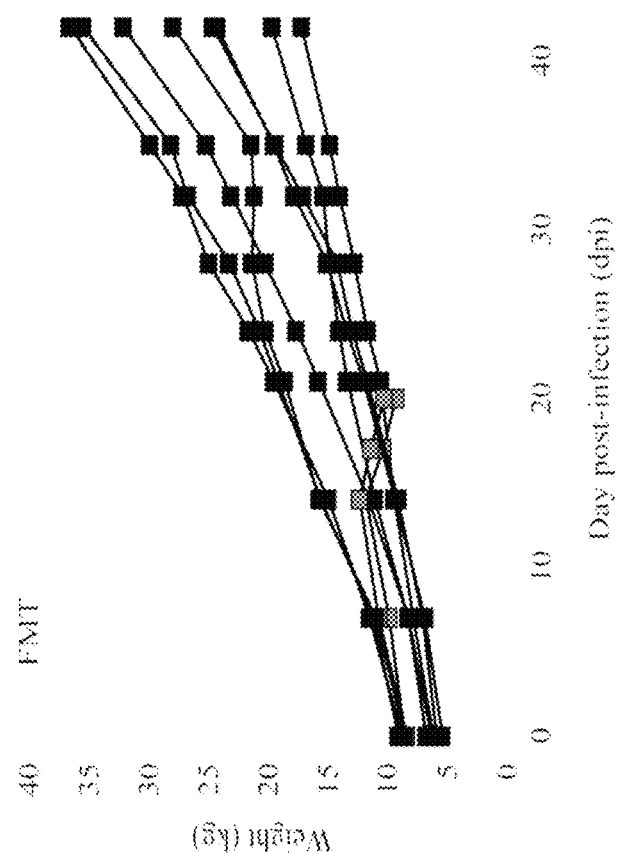
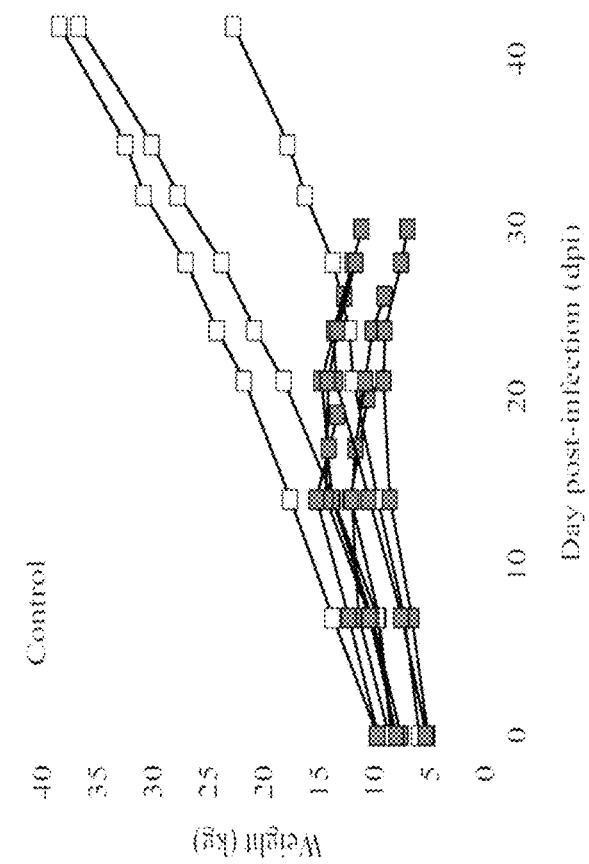

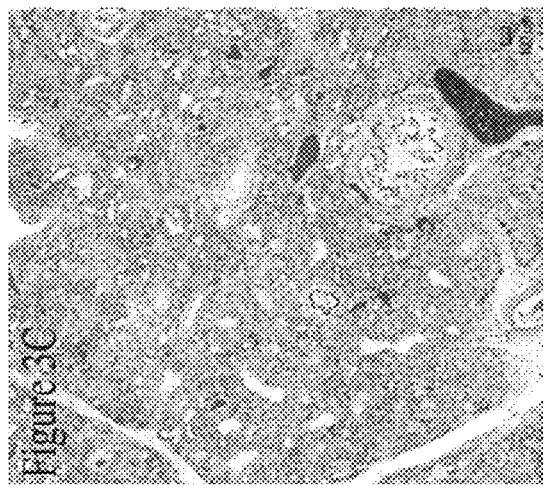
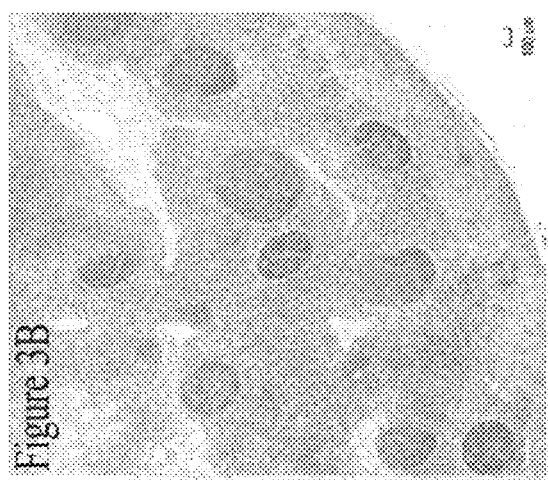
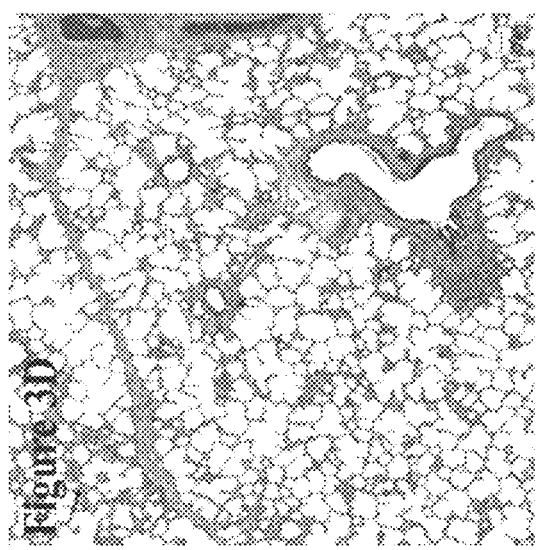

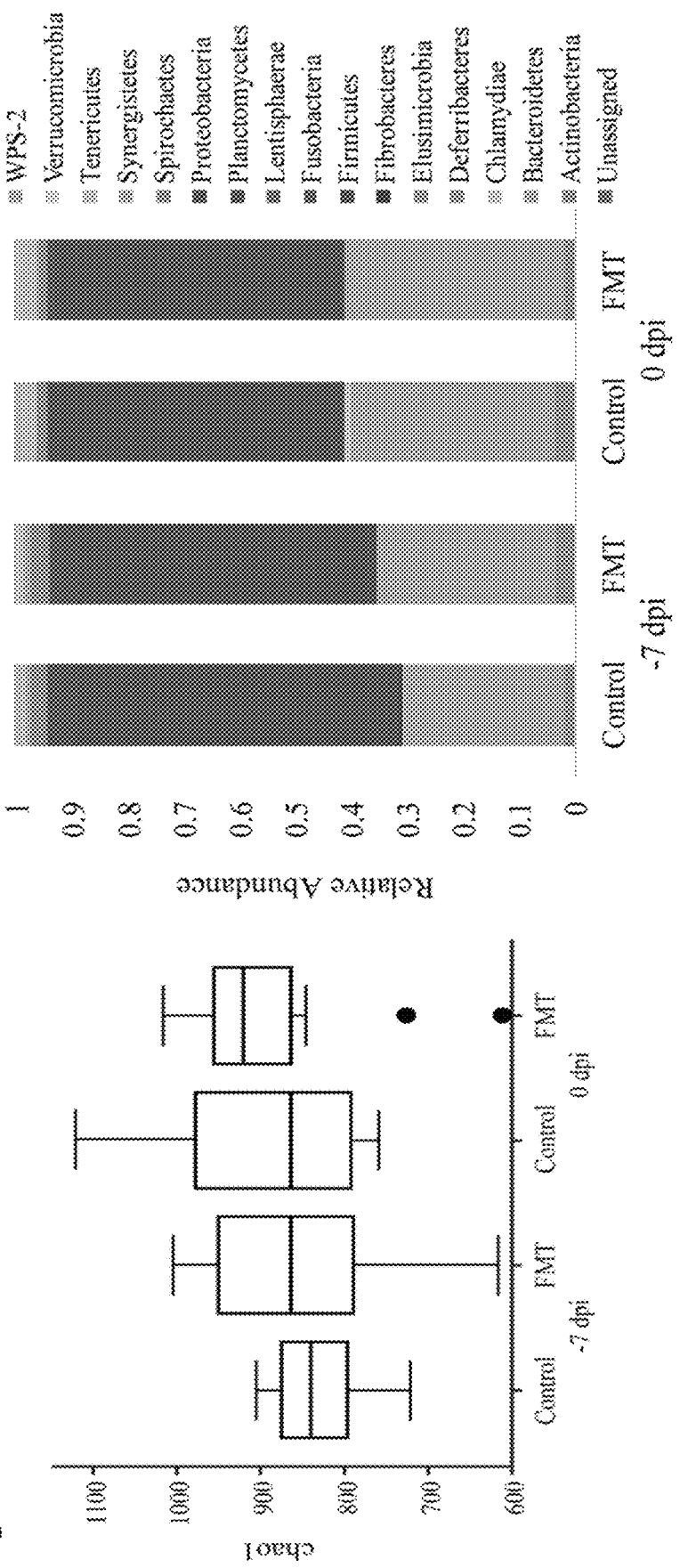

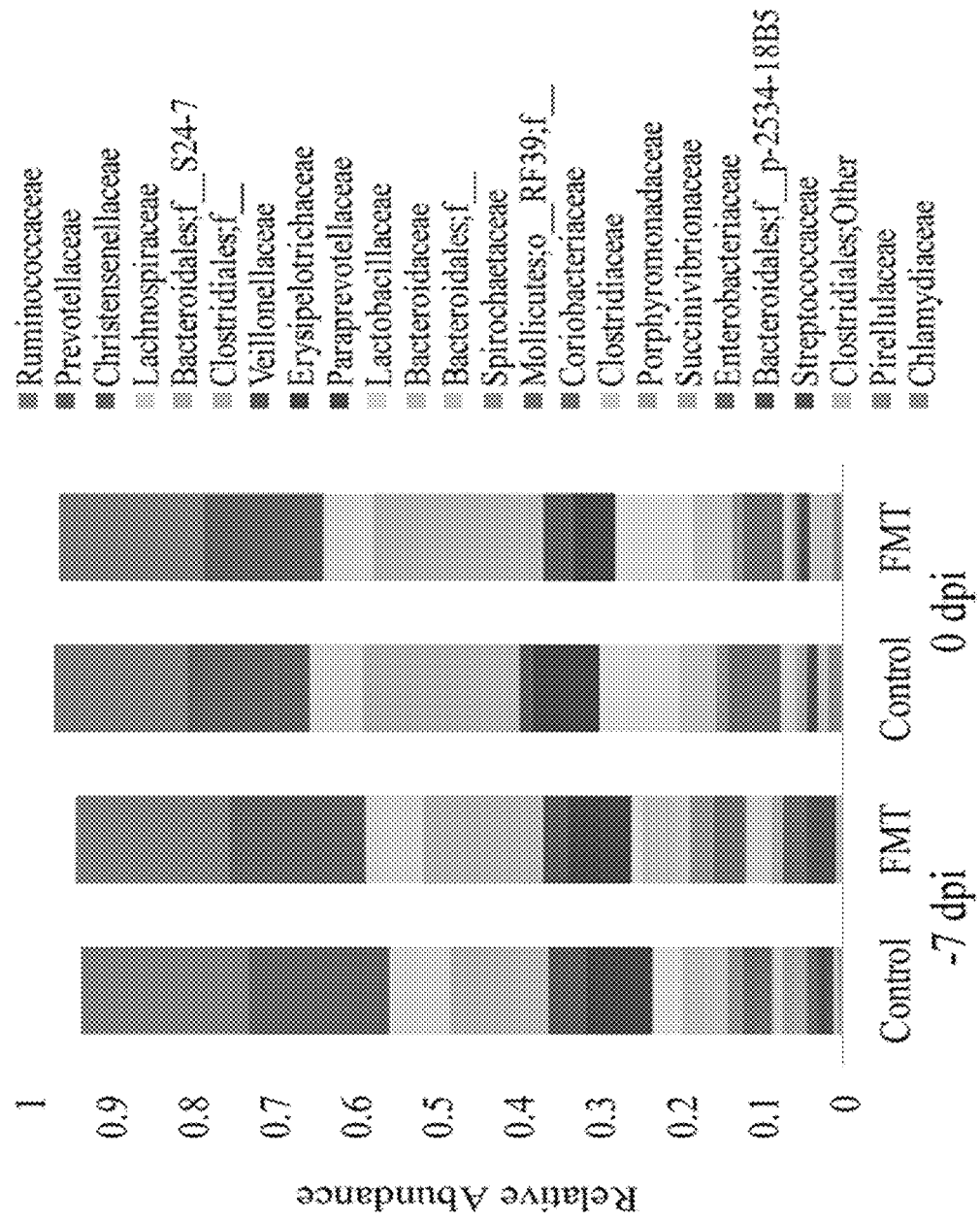

Chao1

Observed OTUs

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
aatgcagagg cgtgattgga                                        20

<210> SEQ ID NO 2
<211> LENGTH: 20
<212> TYPE: DNA
<213> ORGANISM: Artificial Sequence
<220> FEATURE:
<223> OTHER INFORMATION: primer

```
<400> SEQUENCE: 2
ccagtatgtg gtttccgggt                                              20
```

MICROBIOME TRANSPLANTATION

BACKGROUND

Fecal microbiota transplantation (FMT) is the process by which fecal microorganisms amodere donated by a healthy individual and subsequently transplanted into a diseased individual. The actual process of fecal transplantation has been described for centuries, being reported as early as the 4th century in China for the treatment of diarrhea in humans and in the 17th century in Italy as transfaunation for the treatment of diseases in ruminants. The recent uptick in FMT usage and application is evidenced by a search in PubMed, where publication results for either "fecal microbiota transplantation" or "fecal microbiota transplant" comprise approximately 1,200 publications, with almost all being published within the last decade (NCBI, 2017). For several human disease states, FMT has been shown to improve treatment outcome or resolve complex disease conditions. Although recurrent *Clostridium difficile* infections are by far the most frequent application of FMT, other FMT-treatable digestive diseases include inflammatory bowel disease, ulcerative colitis, and metabolic syndrome. The mechanism by which FMT is effective for the treatment of digestive diseases is likely associated with the restoration of normal flora and/or improved nutrient assimilation. FMT is also associated with the improvement of non-digestive diseases, such as neurologic and respiratory disorders. For these conditions, the mechanism for the beneficial effect is likely more complex. For example, FMT restored the production of cytokines, including TNF-α and IL-10, in antibiotic-treated mice after respiratory infection with *Streptococcus pneumoniae*.

A different role for FMT is in the prevention of disease. Traditionally, antibiotics and other growth promoters have been used in food animal production as prophylactics. Part of the benefit is derived from the maintenance of a microbiome that optimizes growth along with the prevention of common bacterial infections. The application of FMT in young animals creates opportunities to establish an optimal normal gut flora as well as modulate innate and adaptive immune responses. As beneficial microbial populations are further characterized for their role in both growth and immunity, FMT or other microbiome therapeutics may provide an alternative to antibiotics and growth promoters in food animal production.

On a global basis, co-infections involving porcine circovirus type 2 (PCV2) and porcine reproductive and respiratory syndrome virus (PRRSV) are common in growing pigs and contribute to a range of polymicrobial disease syndromes. PCV2 is a single-stranded DNA virus in the family Circoviridae which contributes to a group of disease syndromes collectively termed porcine circovirus associated disease or PCVAD. Although PCV2 is essential for PCVAD, PCV2 infection alone rarely results in clinical signs and co-infections are often necessary for disease expression. Three important syndromes associated with PCVAD include PCV2-associated respiratory disease, poor growth performance, and postweaning multisystemic wasting syndrome (PMWS). The hallmark lesion of PCVAD is lymphoid depletion, which reduces the ability of the host to respond to primary and secondary pathogens. Since 2006, the application of PCV2 vaccines has largely controlled PCVAD in North America and Europe. However, the disease still maintains a global impact, especially in countries without vaccination programs.

PRRSV is a single-stranded RNA virus in the family Arteriviridae and causes the single most costly disease affecting swine production worldwide. Losses due to PRRSV infection are associated with increased mortality and reduced growth rates due to respiratory disease in weaned pigs. PRRSV infection also contributes to a number of immunological outcomes that increase the susceptibility of the host to secondary infections by primary and secondary pathogens. PRRSV is frequently isolated along with PCV2 in the field and is one of the major co-factors linked with increasing PCV2 replication and pathogenesis. Outcome following co-infection with PRRSV and PCV2 is often subclinical, with overt clinical disease occurring in only a subpopulation of pigs. Morbidity varies drastically, from subclinical infections and reduced growth performance to increased mortality. Host genetics, immunity, environmental stressors and secondary pathogens are all factors which can impact clinical outcome following PRRSV or PCV2 infections.

Porcine reproductive and respiratory syndrome virus (PRRSV) is the most costly disease of swine worldwide, with estimated annual losses to the U.S. industry at $664 million, primarily due to respiratory disease and reduced weight gain in growing pigs. Porcine circovirus type 2 (PCV2) is also a significant and widely distributed pathogen of swine. PCV2 is a causative factor associated with a group of disease syndromes termed porcine circovirus associated disease or PCVAD, characterized by muscle wasting, respiratory disease, jaundice or pallor, and reduced weight gain in growing pigs. Models for PCVAD include co-infection with PRRSV and PCV2, both of which cause systemic infections primarily targeting pulmonary tissue.

SUMMARY OF THE INVENTION

The present disclosure provides methods and compositions useful for fecal microbiome transplantation. Advantageously, the methods and compositions reduce the incidence of and severity of clinical signs of infections in animals receiving such composition through such methods. In some forms, the clinical signs are caused by or associated with PCV2, PRRSV, or any combination thereof.

One aspect of the disclosure was to determine if FMT could reduce the clinical signs associated with PCVAD in a PRRSV/PCV2 co-infection model. The sources of the FMT material were high-parity sows with long histories of high-health and efficient production characteristics, such as the absence of antimicrobial treatment, low pre-weaning mortality rates, large healthy litters, and a lack of clinical disease. The results showed that FMT reduces the number of pigs affected by PCVAD, including a reduction in virus load and increased viral antigen-specific antibodies. Therefore, FMT provides a potential therapeutic for the prevention of disease.

Previous work utilizing a PRRSV/PCV2 co-infection model has shown a consistent association between increased fecal microbiota diversity and improved outcome in nursery pigs. Specifically, both pre and post-infection fecal microbiome diversity was associated with several improved outcome characteristics after co-infection, including reduced clinical disease severity, reduced virus replication, decreased lung lesions, and improved weight gain. Increased microbiome diversity, as measured by a pan-microbial microarray, was correlated with a reduction in PCVAD clinical signs as well as improved growth in subclinically-affected pigs.

Examples of clinical presentations where treatment was administered included 1) dyspnea and/or tachypnea, 2) mucoid rhinorrhea, 3) conjunctivitis with swelling, 4) pallor or jaundice with muscle wasting, 5) lethargy or depression with pyrexia, and 6) rectal temperature of ≥104° F.

In another aspect of the present disclosure, a population of experimentally infected pigs and a pan-pathogen microarray technology, the Lawrence Livermore Microbial Detection Array (LLMDA), was used to evaluate differences between the best and worst clinical outcomes following co-infection with PRRSV and PCV2.

In another aspect of the present disclosure, the early microbiome properties that predispose high and low growth rates after co-infection in subclinically affected pigs was investigated. The results demonstrated that both microbiome diversity and composition prior to infection play a role in weight gain following PRRSV/PCV2 co-infection.

In another aspect of the present disclosure, a composition for reducing the incidence of or severity of clinical signs associated with or caused by a pathogen is provided. In some forms, the composition is administered to a subject susceptible to infection by the pathogen prior to contact with the pathogen. In some forms, the composition is administered to a subject susceptible to infection by the pathogen after contact with or infection by the pathogen. In some forms, the pathogen is infective and causes clinical signs in a mammal. In some forms, the mammal is a pig. In some forms, the pathogen is selected from the group consisting of PRRSV, PCV2, and any combination thereof. In some forms, the composition is administered via a bolus, chewable product, oral drench, nasal drench, placement on feed (feed additive or top dress), placement in water, or placed on the mammary gland of a sow for subsequent consumption by suckling animals. In some forms, the composition is administered at any time. In some forms, the composition is administered 1-2 days after birth. In other forms, the composition is administered up to or at the time of weaning. In other forms, the composition is administered immediately after weaning in the early nursery period. In still other forms, the composition is administered after the presence of a pathogen is discovered in a herd or group of animals. In still other forms, the composition is administered on a repeated basis to members of the group used for breeding purposes. In some forms, the composition comprises one or more microorganisms including bacteria or viruses that are found in the gastrointestinal microbiome. In some forms, the composition comprises one or more microorganisms that are found in the microbiome of an animal that is resistant to infection by a pathogen capable of causing clinical signs in animals of the same species as the animal that is resistant. In some forms, the composition comprises one or microorganisms that is found in greater numbers or in a higher proportion relative to an animal that is not resistant to infection by the pathogen. In some forms, the microorganism is selected from the group consisting of a member of a family selected from the group consisting of Intrasporangiaceae, Veillonellaceae, Lachnospiraceae, Ruminococcaceae, Streptococcaceae, and any combination thereof (List 1). In some forms, the microorganism is selected from the group consisting of Intrasporangiaceae bacterium JGI 0001002-M5, Rhinovirus B, *Escherichia coli*, *Streptococcus equi* and any combination thereof (List 2). In some forms, the microorganism is selected from the group consisting of one or more of the microorganisms provided in the List 3 below:

List 3:

| OTUID | taxonomy | taxonomy | Highly_Abundant_In |
|---|---|---|---|
| 10 | o_Erysipelotrichales | f_Erysipelotrichaceae | D0_Unaffected |
| 47 | o_Clostridiales | f_Ruminococcaceae | D0_Unaffected |
| 55 | o_Clostridiales | f_Veillonellaceae | D0_Unaffected |
| 14 | o_Clostridiales | f_Ruminococcaceae | D0_Unaffected |
| 155 | o_Bacteroidales | f_Prevotellaceae | D0_Unaffected |
| 252 | o_Clostridiales | f_Lachnospiraceae | D0_Unaffected |
| 42 | o_Clostridiales | f_Ruminococcaceae | D0_Unaffected |
| 394 | o_Clostridiales | f_Ruminococcaceae | D0_Unaffected |
| 254 | o_Clostridiales | f_Ruminococcaceae | D0_Unaffected |
| 270 | o_Bacteroidales | f_No Assigned Family | D0_Unaffected |
| 262 | o_RF39 | f_No Assigned Family | D0_Unaffected |
| 426 | o_Clostridiales | f_Lachnospiraceae | D0_Unaffected |
| 162 | o_Bacteroidales | f_No Assigned Family | D0_Unaffected |
| 645 | o_Clostridiales | f_Clostridiaceae | D0_Unaffected |
| 260 | o_Clostridiales | f_No Assigned Family | D0_Unaffected |
| 431 | o_Bacteroidales | f_Prevotellaceae | D0_Unaffected |
| 497 | o_Erysipelotrichales | f_Erysipelotrichaceae | D0_Unaffected |
| 347 | o_Bacteroidales | f_No Assigned Family | D0_Unaffected |
| 334 | o_Coriobacteriales | f_Coriobacteriaceae | D0_Unaffected |
| 1674 | o_Clostridiales | f_Ruminococcaceae | D0_Unaffected |
| 638 | o_Erysipelotrichales | f_Erysipelotrichaceae | D0_Unaffected |
| 306 | o_Clostridiales | f_Ruminococcaceae | D0_Unaffected |
| 655 | o_Erysipelotrichales | f_Erysipelotrichaceae | D0_Unaffected |
| 450 | o_Clostridiales | f_Ruminococcaceae | D0_Unaffected |
| 1607 | o_Clostridiales | f_Lachnospiraceae | D0_Unaffected |
| 244 | o_Clostridiales | f_Lachnospiraceae | D0_Unaffected |
| 1734 | o_Clostridiales | f_No Assigned Family | D0_Unaffected |
| 276 | o_Clostridiales | f_Lachnospiraceae | D0_Unaffected |
| 557 | o_Clostridiales | f_Ruminococcaceae | D0_Unaffected |

In some forms, the microorganism is selected from the group consisting of one or more of the microorganisms provided in List 4 below wherein "p" denotes Phylum, "c" denotes Class; "o" denotes Order, "f" denotes Family, "g" denotes Genus, and "s" denotes Species:

List 4:
_Firmicutes; c_Clostridia; o_Clostridiales; f_Veillonellaceae; g_; s_
p_Firmicutes; c_Clostridia; o_Clostridiales; f_Ruminococcaceae; g_Oscillospira; s_ p_Firmicutes; c_Clostridia; o_Clostridiales; f_Lachnospiraceae; g_Dorea; s_
p_Firmicutes; c_Clostridia; o_Clostridiales; f_Veillonellaceae; g_; s_
p_Firmicutes; c_Clostridia; o_Clostridiales; f_Veillonellaceae; g_Megasphaera; s_
p_Bacteroidetes; c_Bacteroidia; o_Bacteroidales; f_S24-7; g_; s_
p_Firmicutes; c_Clostridia; o_Clostridiales; f_Ruminococcaceae; g_; s_
p_Firmicutes; c_Clostridia; o_Clostridiales; f_Lachnospiraceae; g_; s_
p_Firmicutes; c_Clostridia; o_Clostridiales; f_Lachnospiraceae; g_; s_
p_Actinobacteria; c_Coriobacteriia; o_Coriobacteriales; f_Coriobacteriaceae; g_; s_
p_Bacteroidetes; c_Bacteroidia; o_Bacteroidales; f_; g_; s_
p_Firmicutes; c_Clostridia; o_Clostridiales; f_Ruminococcaceae; g_; s_
p_Bacteroidetes; c_Bacteroidia; o_Bacteroidales; f_; g_; s_
p_Firmicutes; c_Clostridia; o_Clostridiales; f_Veillonellaceae; g_Megasphaera; s_
p_Firmicutes; c_Clostridia; o_Clostridiales; f_Ruminococcaceae; g_; s_

In some forms, the composition comprises one or more microorganisms from one or more of lists 1, 2, 3, and 4. In some forms, the composition comprises at least 2, 3, 4, 5, 6, 7, 8, 9, or more microorganisms. In some forms, the composition comprises one or more microorganisms from a phylum selected from the group consisting of Firmicutes, Bacteroidetes, Actinobacteria, and any combination thereof. In some forms, the composition comprises one or more microorganisms from a class selected from the group consisting of Clostridia, Bacteroidia, Coriobacteriia, and any combination thereof. In some forms, the composition comprises one or more microorganisms from an order selected from the group consisting of Erysipelotrichales, Clostridiales, Bacteroidales, RF39, Coriobacteriales, and any combination thereof. In some forms, the composition comprises one or more microorganisms from a family selected from the group consisting of Intrasporangiaceae, Veillonellaceae, Lachnospiraceae, Ruminococcaceae, Erysipelotrichaceae, Prevotellaceae, Clostridiaceae, Streptococcaceae, Coriobacteriaceae, S24-7, and any combination thereof. In some forms, the composition comprises one or more organisms from a genus selected from the group consisting of *Megasphaera, Oscillospira, Dorea*, and any combination thereof. In some forms, the composition comprises one or more organisms from a species selected from the group consisting of Intrasporangiaceae bacterium JGI 0001002-M5, Rhinovirus B, and any combination thereof. In some forms, the composition comprises at least two or more microorganisms independently and respectively selected from the phylums, classes, orders, families, genuses, and species described above. In some forms, the composition includes, or is administered with a prebiotic. In some forms, the composition is administered with or includes a component selected from the group consisting of a preservative, stabilizer, antibiotic, and any combination thereof.

In some forms, the composition comprises at least 2 log CFU/ml/dose of microorganism when the microorganism is a bacteria, more preferably between 2-9 log CFU/ml/dose, more preferably between 3-8 log CFU/ml/dose, still more preferably between 5-7 log CFU/ml/dose. In some forms, the composition comprises at least 2 $TCID_{50}$/ml/dose when the microorganism is a virus, more preferably between 2-10 $TCID_{50}$/ml/dose, even more preferably between 2-8 $TCID_{50}$/ml/dose, still more preferably between 2-6 $TCID_{50}$/ml/dose, even more preferably between 2-4 $TCID_{50}$/ml/dose.

In another aspect of the present disclosure, a method of reducing the incidence or severity of an infection is provided. The method generally comprises the step of administering a composition as described in this disclosure to an animal in need thereof. In some forms, the infection is caused by or associated with a pathogen of a mammal, preferably a pig. In some forms, the pathogen is known to cause or be associated with respiratory infections. In some forms, the pathogen is a pathogen that produces respiratory infection. In some forms, the pathogen is selected from the group consisting of PRRSV, PCV2, *Mycoplasma hyopneumonia*, swine influenza, and any combination thereof. In some forms, the method results in a decrease or reduction in the incidence or severity of clinical signs caused by the infection by at least 10, 20, 30, 40, 50, 60, 70, 80, 90, and even 100% in comparison to clinical signs in an animal or group of animals that did not receive an administration of the composition. In some forms, the composition is administered a single time. In other forms, the composition is administered multiple times, as described in this disclosure. In some forms, the clinical signs are selected from the group consisting of dyspnea, aural cyanosis, coughing, nasal discharge, open mouth breathing, poor body condition, muscle wasting, pallor or jaundice, lameness, joint effusion, depression, lethargy, and any combination thereof. In some forms, the administration is before the presentation of any clinical signs described herein as a prevention method. In some forms, the administration is after the presentation of any of the clinical signs described herein by the subject receiving the administration or another animal in a group of animals to which the subject receiving the administration belongs to (i.e. another member of the same herd). In some forms, the administration occurs both before and after the presentation of clinical signs as described herein.

In another aspect of the present disclosure, a method of increasing growth rate in an animal is provided. The method generally includes the step of altering the diversity and/or relative amounts of one or more microorganisms in the gastrointestinal microbiome of an animal. In some forms, the altering step includes administering a composition as described in this disclosure. In some forms, the relative amounts of Ruminococcaceae, and Streptococcaceae microorganisms are increased as a result of the administration, with the comparison occurring between the amounts of Ruminococcaceae and Streptococcaceae as a part of the overall microflora in the microbiome prior to administration and the amounts after the administration. In some forms, the relative amounts of Methanobacteriaceae are decreased after the administration of the composition. In some forms, the relative amounts of *E. coli* are increased after the administration of the composition. In some forms, the composition includes at least one microorganism selected from the group consisting of Ruminococcaceae, Streptococcacceae, *E. coli*, and any combination thereof. In some forms, the growth rate is determined by average daily weight gain (ADWG).

In another aspect of the disclosure, fecal microbiota described above is cultured and quantified. Such cultures can then be used in transplant and therapeutic applications.

In another aspect of the disclosure, bacteria identified in the cultures of fecal matter are used as the components of a therapeutic composition. In some forms, the composition will comprise at least 1, 2, 3, 4, 5, 6, 7, 8, 9, 10, 11, 12, 13, 14, 15, 16, 17, 18, 19, 20, 21, 22, 23, 24 or more cultured species of bacteria. In some forms, the composition is formed from the fecal microbiota. In some forms, the composition is formed by combining cultured strains of the bacteria. In some forms, the bacteria are selected from the group consisting of *Bacillus* sp., *Clostridium* sp., *Escherichia* sp., *Staphylococcus* sp., *Shigella* sp., *Enterococcus* sp., *Streptococcus* sp., *Lactobacillus* sp., *Bifidobacterium* sp., *Actinomyces* sp., and any combination thereof. In some forms, the bacteria are selected from the group consisting of *Bacillus amyloliquefaciens, Bacillus licheniformis, Escherichia coli, Bacillus safensis, Staphylococcus carnosus, Shigella sonnei, Enterococcus mundtii, Enterococcus faecium, Streptococcus gallolyticus, Enterococcus faecium, Lactobacillus vaginalis, Bifidobacterium indicum, Bacillus pumilus, Bacillus megaterium, Staphylococcus simulans, Enterococcus hirae, Streptococcus alactolyticus, Lactobacillus mucosae, Actinomyces hyovaginalis, Clostridium perfringens, Bifidobacterium thermophilum*, and any combination thereof.

In another aspect of the disclosure, a composition described above is administered in an amount comprising 1, 2, 3, 4, 5, 6, 7, 8, 9, 10, 11, 12, 13, 14, 15, 16, 17, 18, 19, 20 or more ml, wherein each ml comprises at least $1.00E+02$ of one or more of the bacteria described above. In some forms, each ml comprises at least $1.00E+02$ of each bacteria included in the composition, wherein the bacteria include one or more of the species described above. In some forms, the amount of any one bacteria species in each ml is at least $2.00E+02$, $1.00E+03$, $1.00E+04$, $1.00E+04$, $1.00E+06$, $1.00E+07$, $1.00E+08$, $1.00E+9$, $1.00E+10$, or more. In some forms, the composition is administered 1, 2, 3, 4, 5, 6, 7, 8, 9, 10, 11, 12, 13, 14, 15, 16, 17, 18, 19, 20, or more times. In some forms, the composition is administered 1, 2, 3, 4, 5, 6, 7, 8, 9, 10, or more times a day. In some forms, repeated administrations are provided every 2, 4, 6, 8, 10, 12, 14, 16, 18, 20, 22, 24, 36, 48, 60, 72, 84, 96, 108, or more hours.

In some forms, the therapeutic composition further includes a component selected from the group consisting of a prebiotic, preservative, stabilizer, antibiotic, or any combination thereof.

In some forms, the therapeutic composition reduces the incidence or severity of infections by a pathogen, preferably as described above. In some forms, the pathogen is known to cause at least one clinical sign of respiratory infection, preferably as described above. In some forms, the pathogen is selected from the group consisting of PRRSV, PCV2, *Mycoplasma hyopneumonia*, swine influenza, and any combination thereof. In some forms, the therapeutic composition is administered as described above.

BRIEF DESCRIPTION OF THE DRAWING FIGURES

The drawings described herein are for illustration purposes only and are not intended to limit the scope of the present teachings in any way.

FIG. 1 includes a panel of 3 graphs:

FIG. 1A is a graph comparing morbidity and mortality of pigs with and without fecal microbiota transplantation prior to co-infection with PRRSV and PCV2d. Percent morbidity over time; data is shown as the percent of pigs in each group with veterinary treatment prescribed due to moderate to severe clinical disease. Asterisks demarcate statistically significant differences (*$p<0.05$ and ‡$p<0.1$; Fisher's exact test);

FIG. 1B is a graph comparing survival of pigs with and without fecal microbiota transplantation prior to co-infection with PRRSV and PCV2d. The survival curve shows a significantly higher survival rate in pigs administered the fecal transplant material ($p=0.04$, Mantel-Cox test);

FIG. 1C is a graph comparing weight of pigs with and without fecal microbiota transplantation prior to co-infection with PRRSV and PCV2d. Weight gain is shown as the mean of control and FMT groups considered unaffected (squares) and affected (circles) by PCVAD, as identified by mortality and clinical disease. The surviving pigs in each group are shown at the bottom of the figure over time;

FIG. 2 includes a panel of 2 graphs:

FIG. 2A is a graph illustrating weight gain of individual pigs from the control group after co-infection with PRRSV and PCV2d. Data is shown as individual pig weights over the course of the 42-day post-infection period. Pigs shown in gray are those that died or were humanely euthanized due to severity of disease associated with PCVAD. At the conclusion of the study, 3 pigs had survived in the control group;

FIG. 2B is a graph illustrating weight gain of individual pigs from the FMT group after co-infection with PRRSV and PCV2d. Data is shown as individual pig weights over the course of the 42-day post-infection period. Pigs shown in gray are those that died or were humanely euthanized due to severity of disease associated with PCVAD. At the conclusion of the study, 8 pigs had survived in the FMT group;

FIG. 3 includes a panel of 9 photographs of representative gross and microscopic lesions associated with porcine circovirus associated disease (PCVAD). Images shown are from representative PCVAD-affected pigs with severe clinical disease between 19 and 30 dpi. In FIGS. 3B and 3D, representative images are also shown from minimally-affected pigs for the purpose of comparison;

FIG. 3A is a photograph showing immunohistochemical staining of a tracheobronchial lymph node showing severe lymphoid depletion associated with large amounts of PCV2 antigen;

FIG. 3B is a photograph showing immunohistochemical staining of a tracheobronchial lymph node showing lymphoid follicles with minimal lymphoid depletion and no PCV2 antigen staining;

FIG. 3C is a photograph showing an H&E-stained lung showing severe diffuse interstitial pneumonia affecting greater than 75% of lung;

FIG. 3D is a photograph showing an H&E-stained lung showing mild and multifocal interstitial pneumonia affecting less than 50% of lung;

FIG. 3E is a photograph of a dorsal and ventral gross lung showing severe consolidation, hemorrhage, and pneumonia affecting approximately 95% of lung;

Figure 4B:
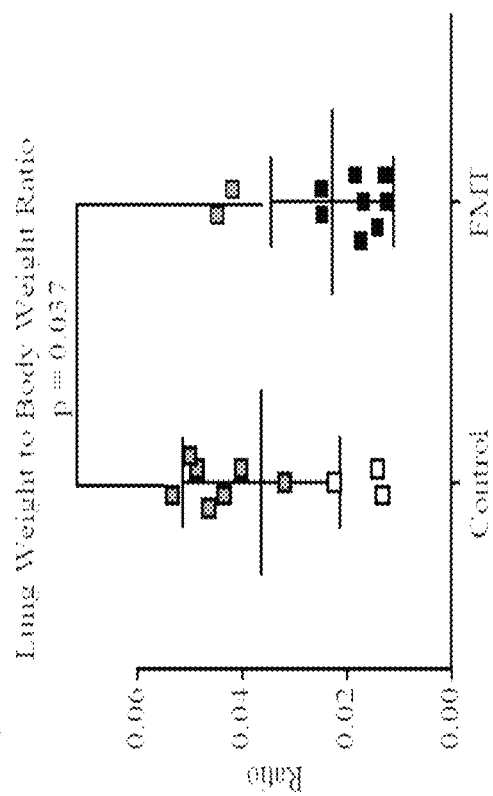
Figure 4A:
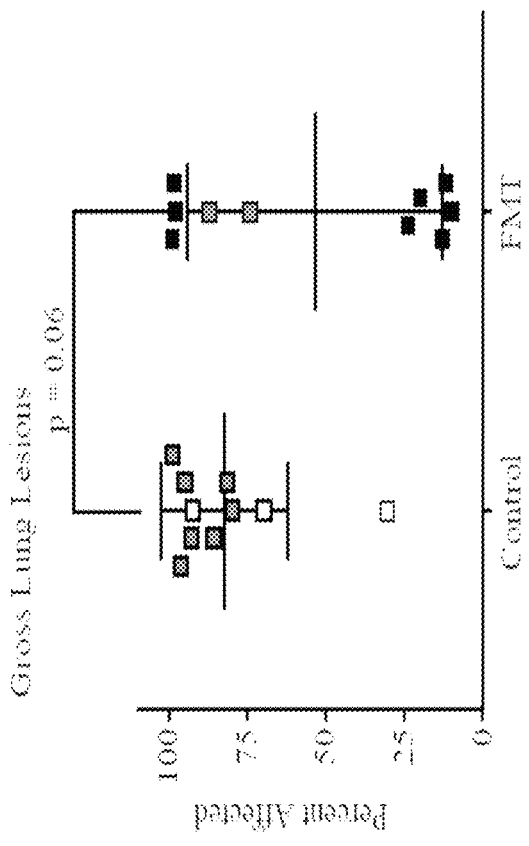
Figure 4D:
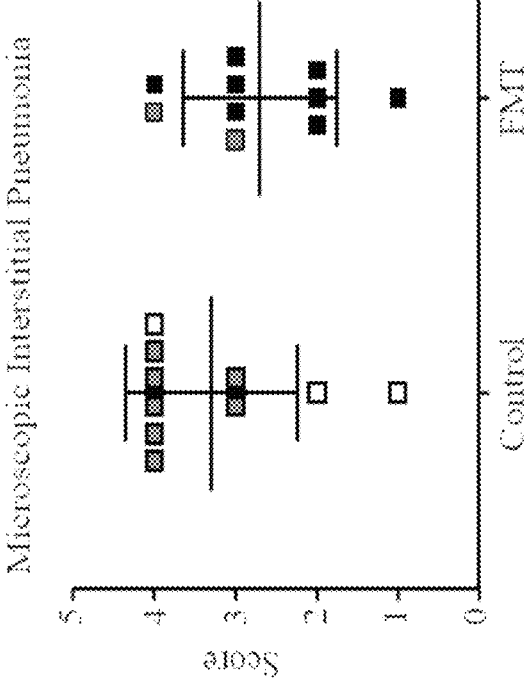
Figure 4C:
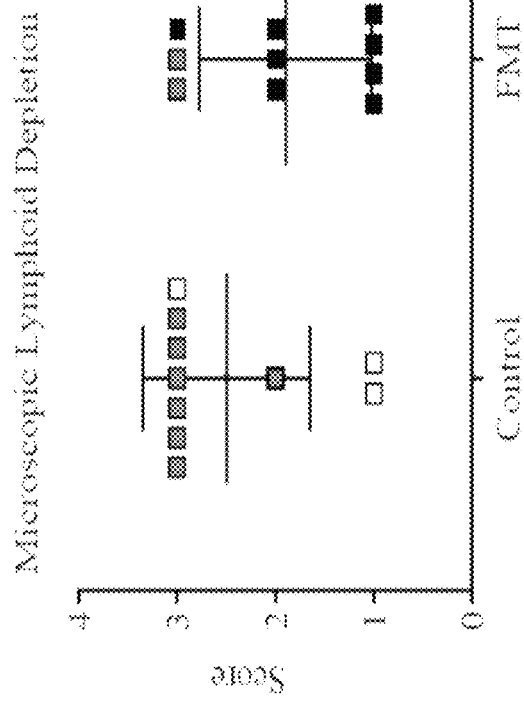
Figure 5B:
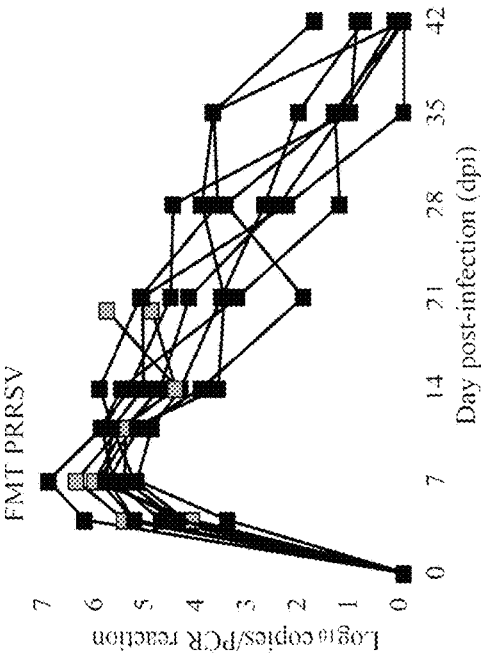
Figure 5D:
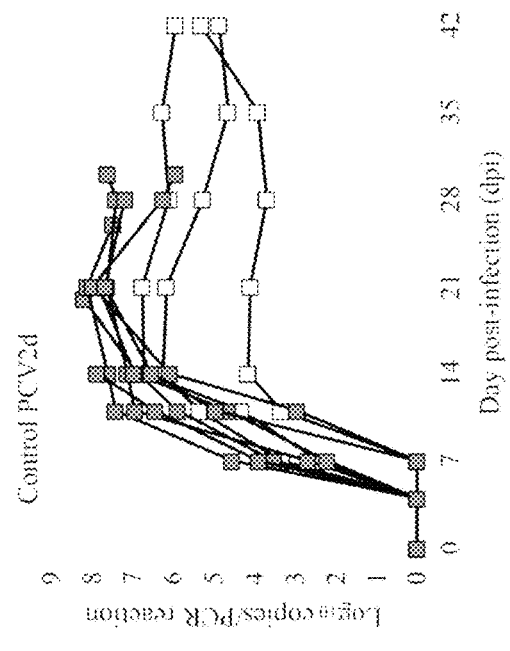
Figure 5A:
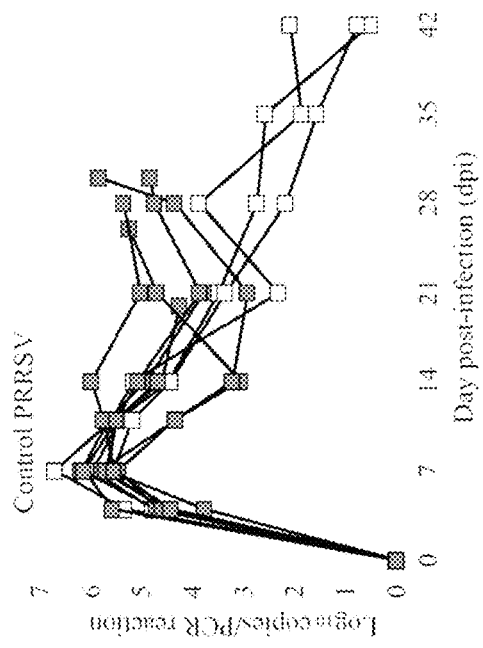
Figure 5C:
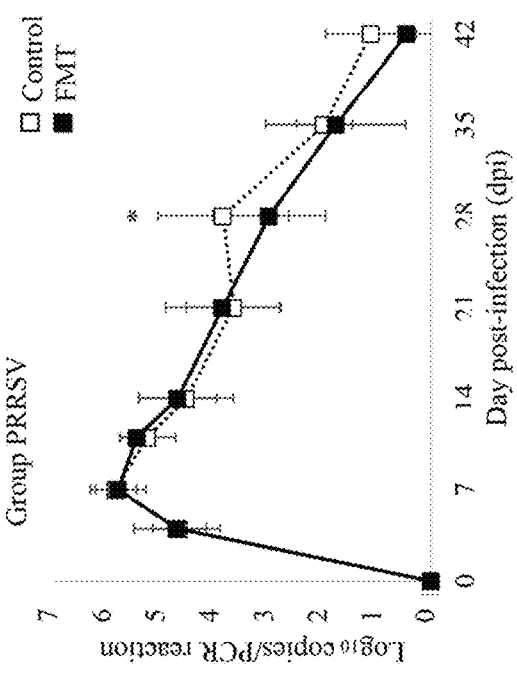
Figure 5F:
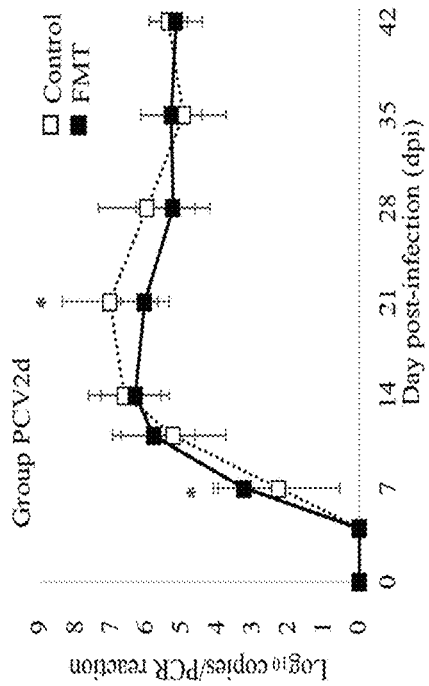
Figure 5H:
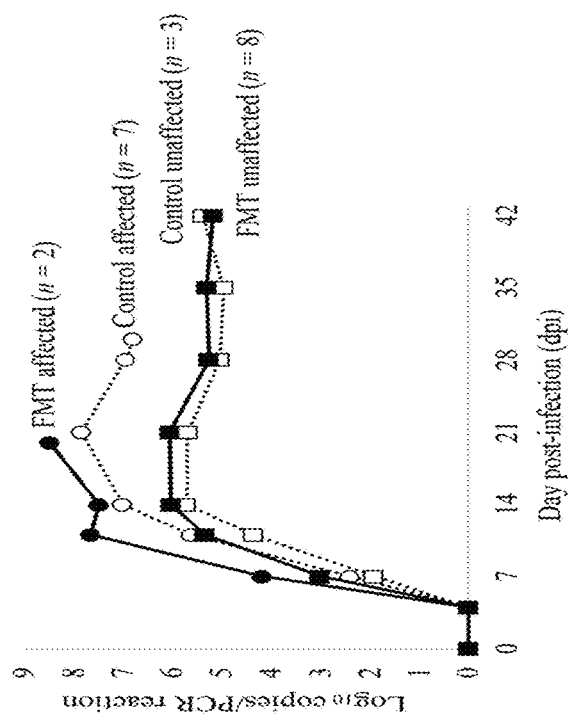
Figure 5E:
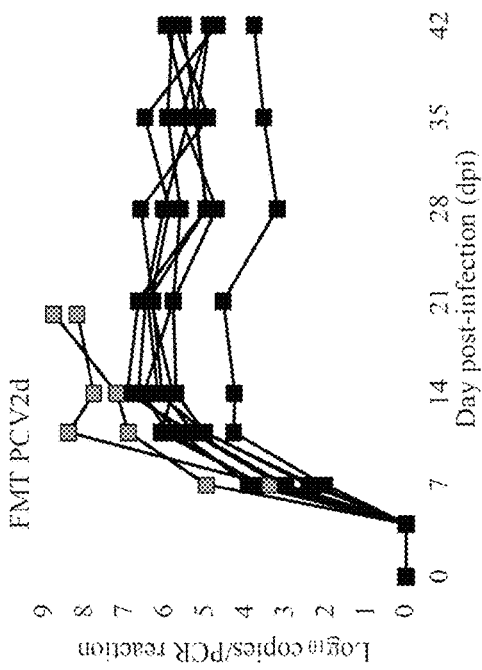
Figure 5G:
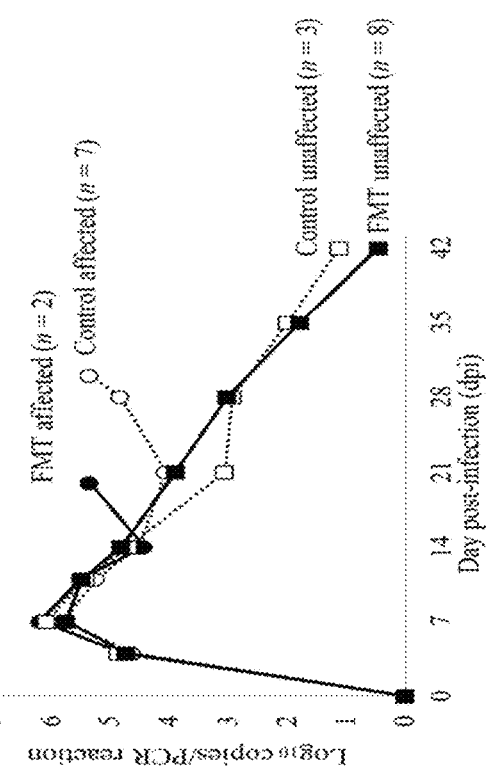
Figure 6A:
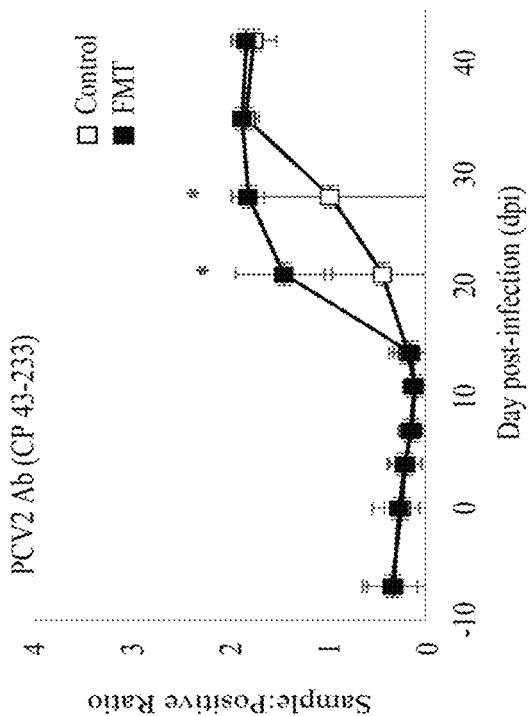
Figure 6B:
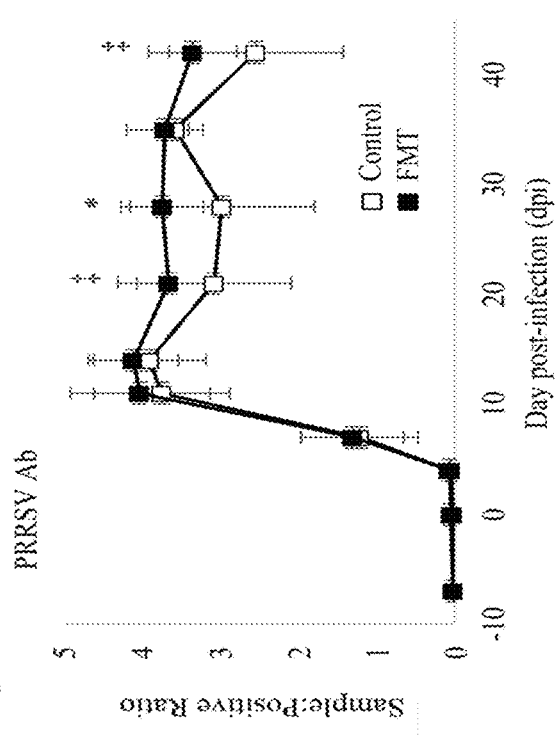
Figure 6C:
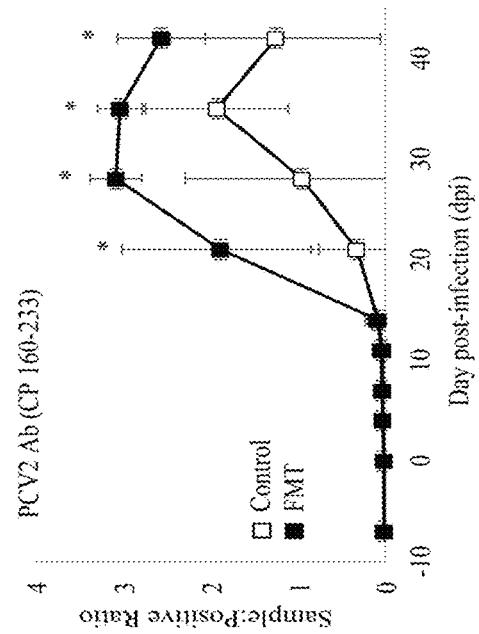
Figure 7A:
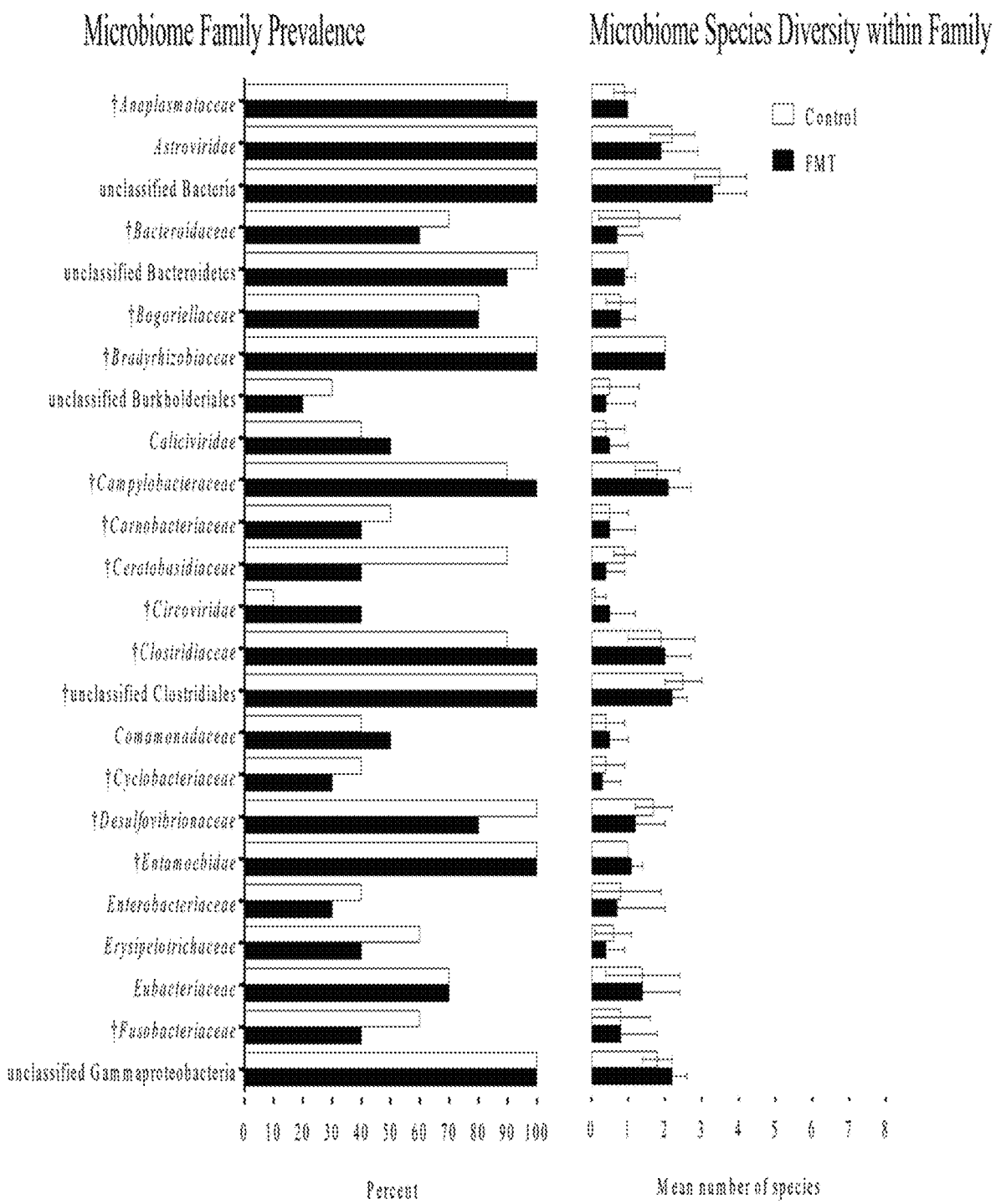
Figure 7B:
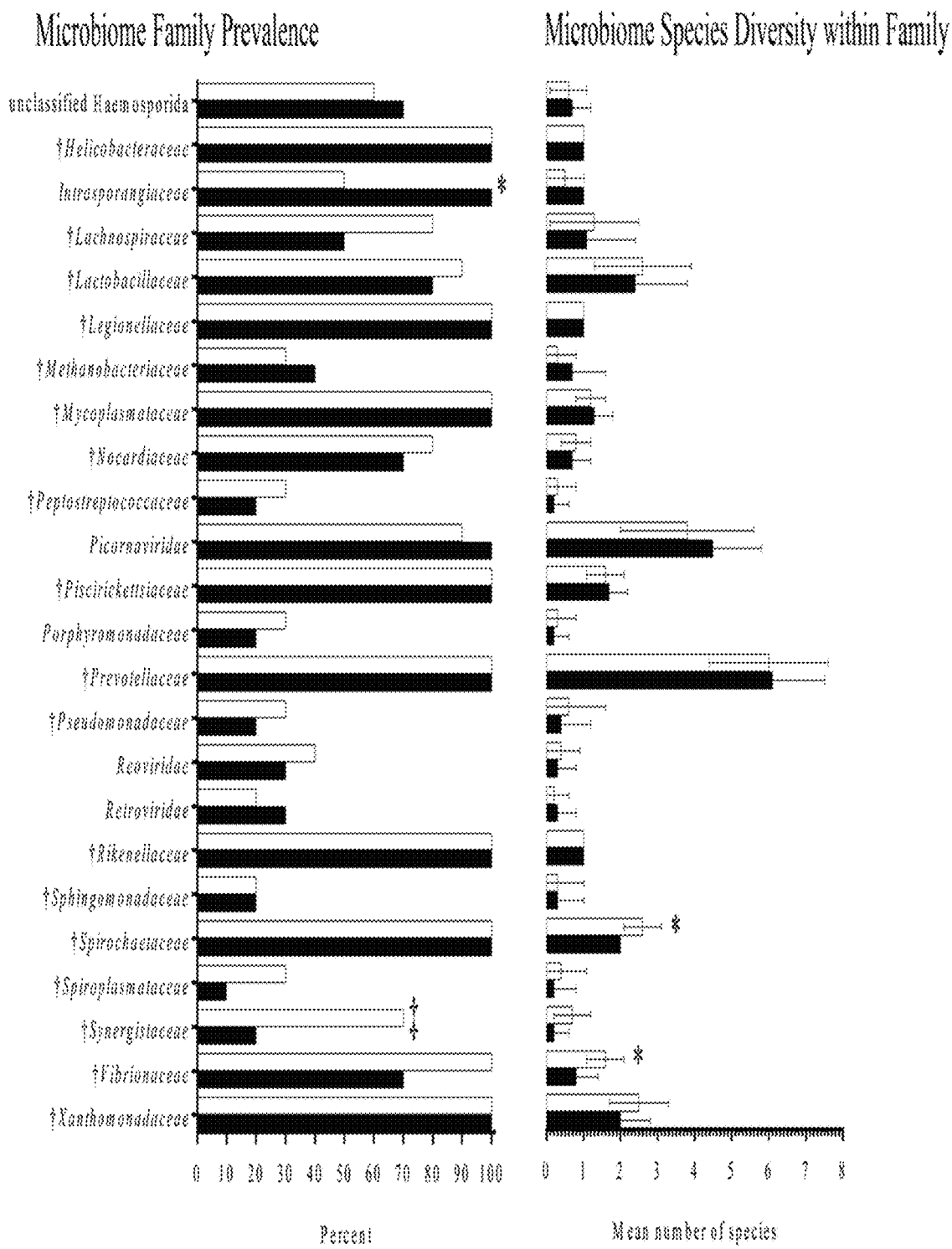
Figure 9:
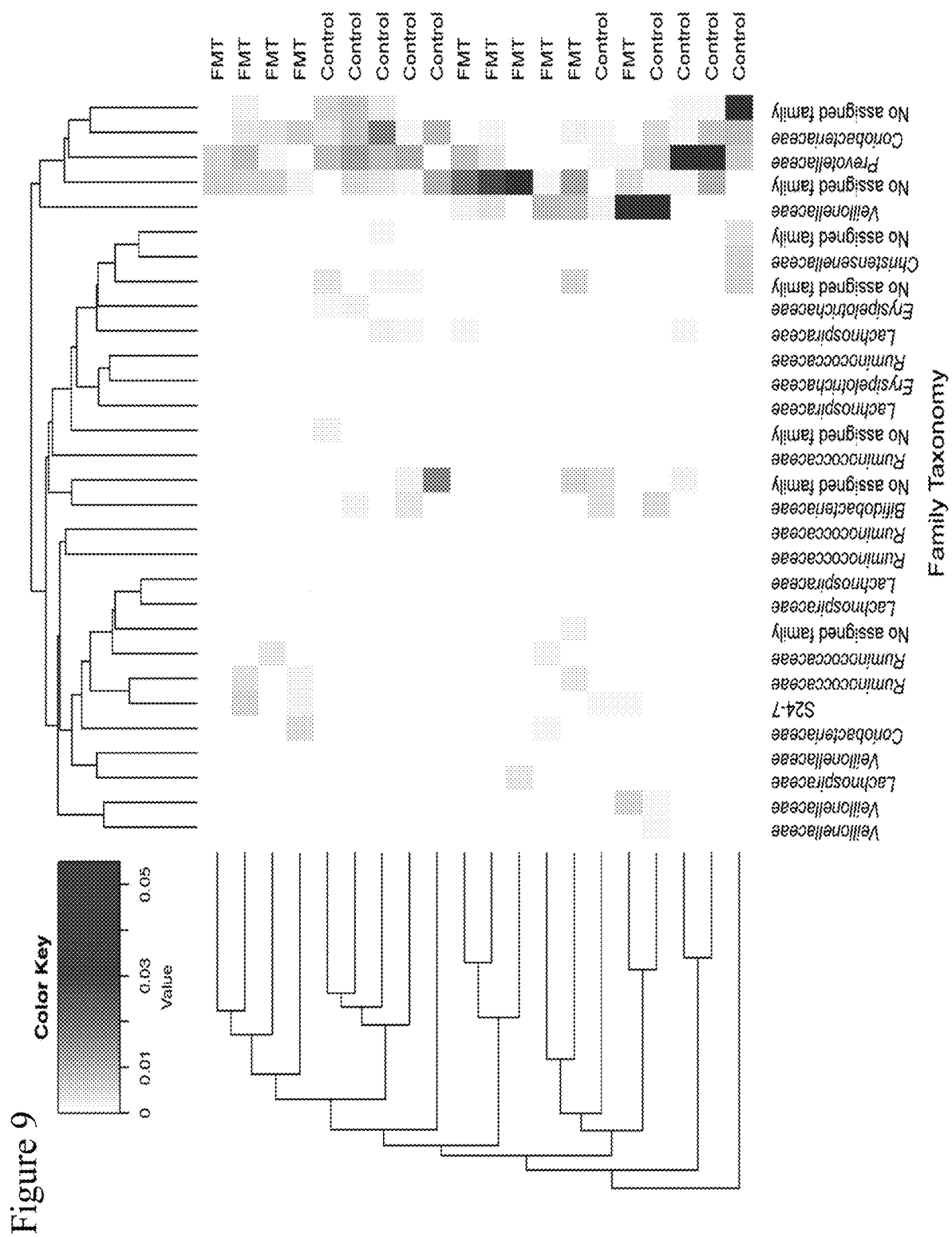
Figure 10A:
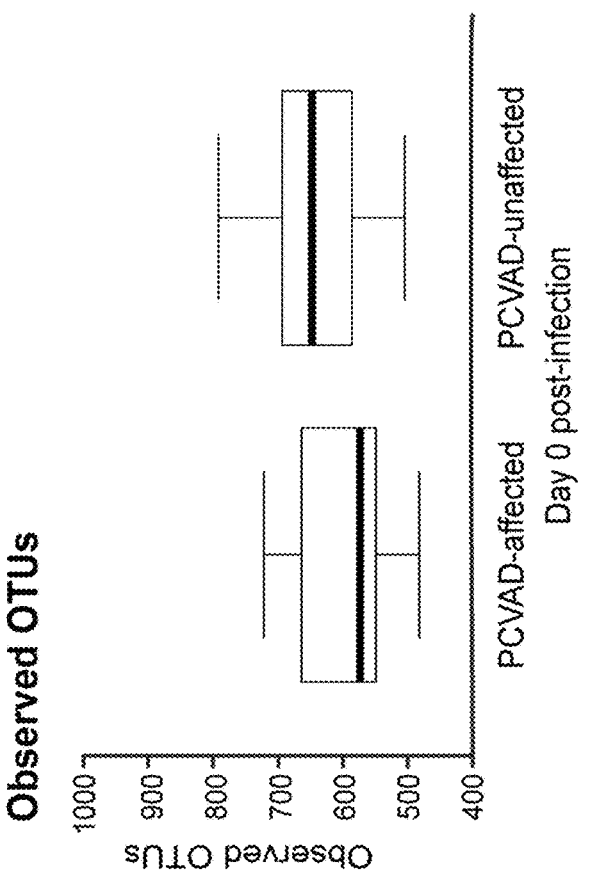
Figure 10B:
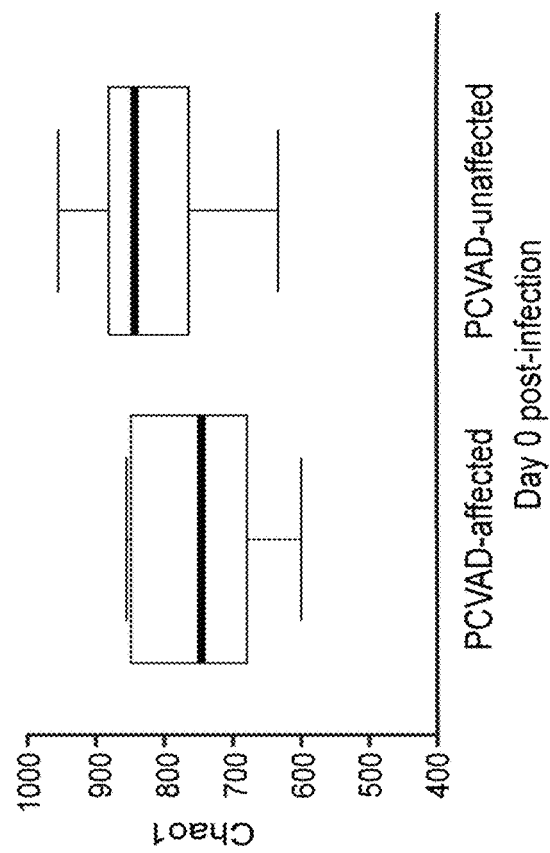
Figure 11:
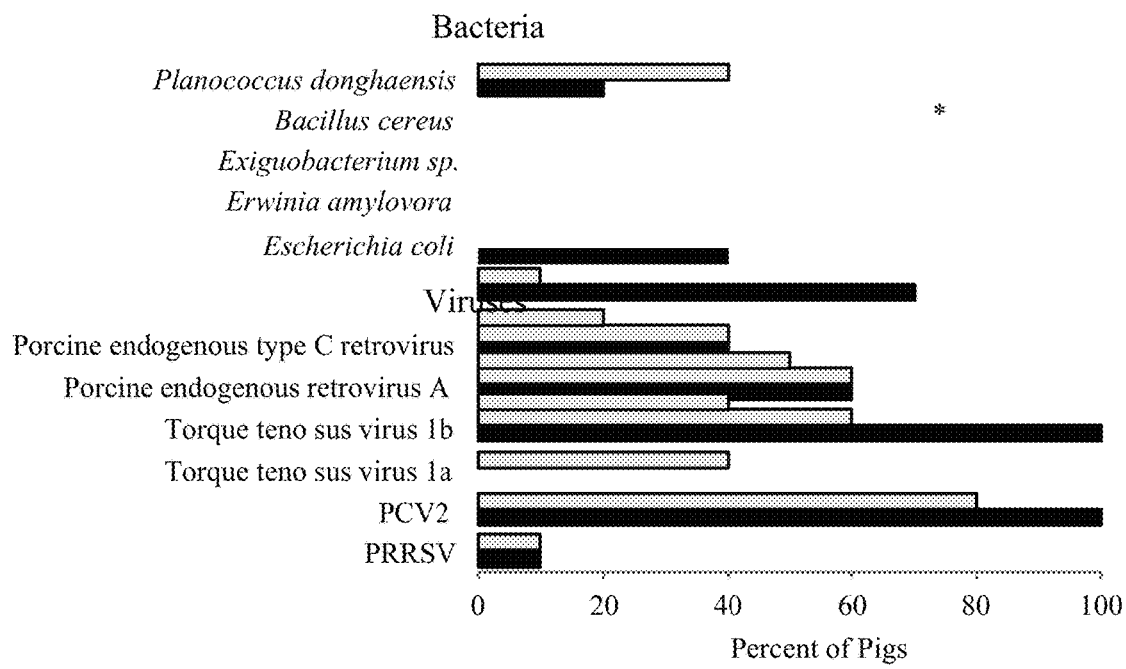
Figure 12:
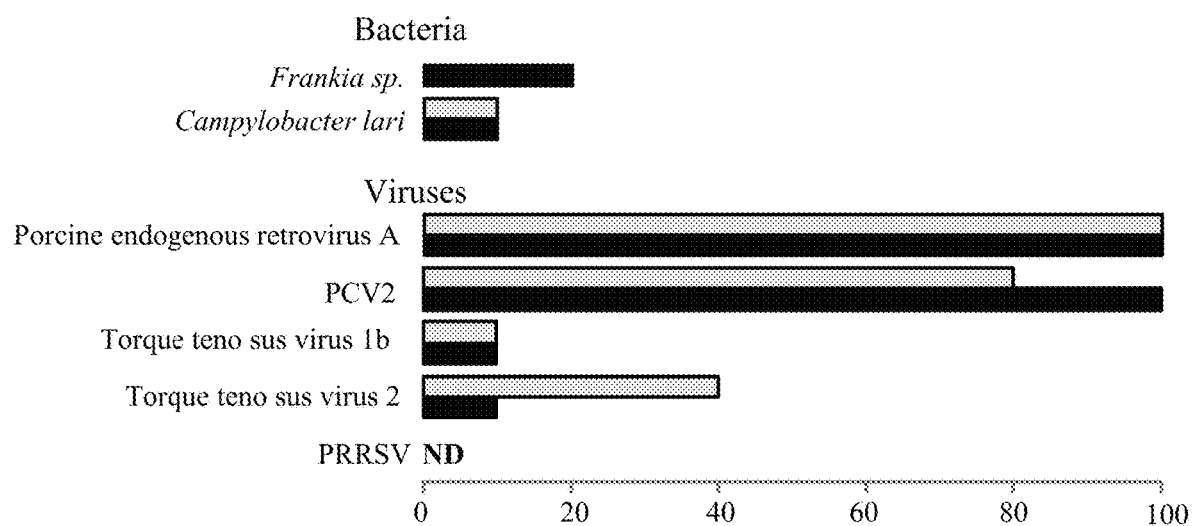
Figure 13:
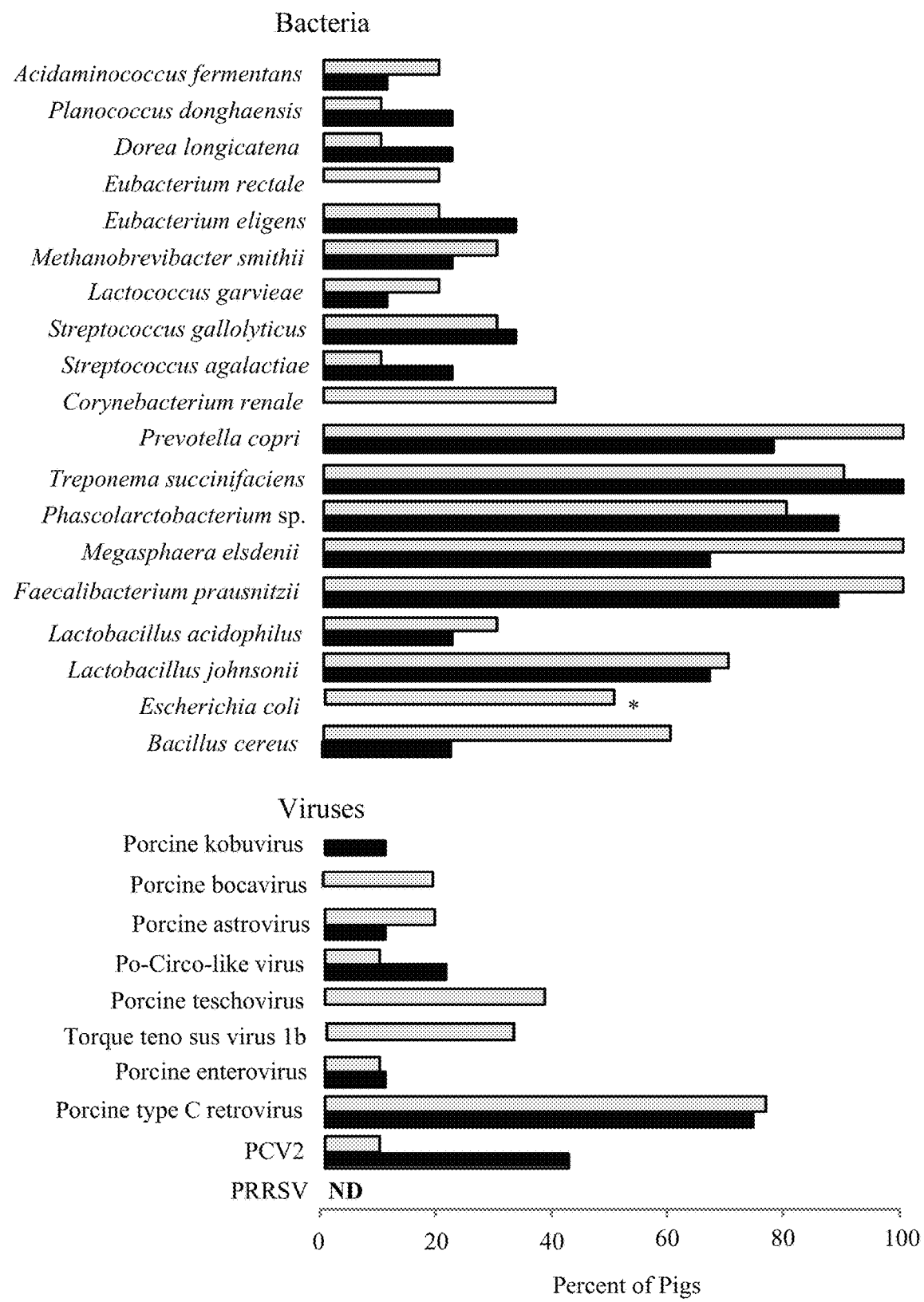
Figure 14:
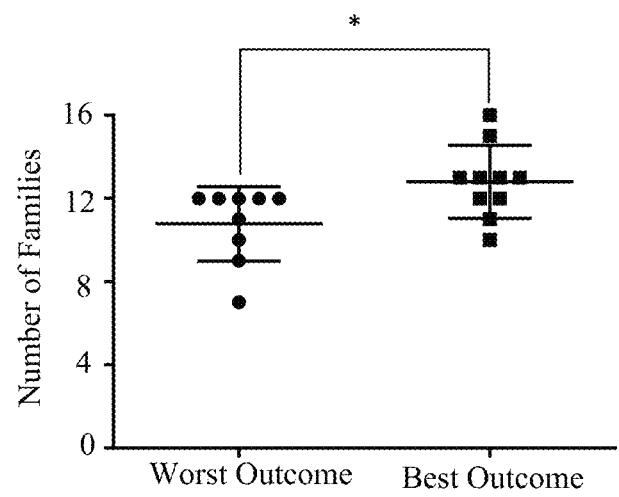
Figure 15:
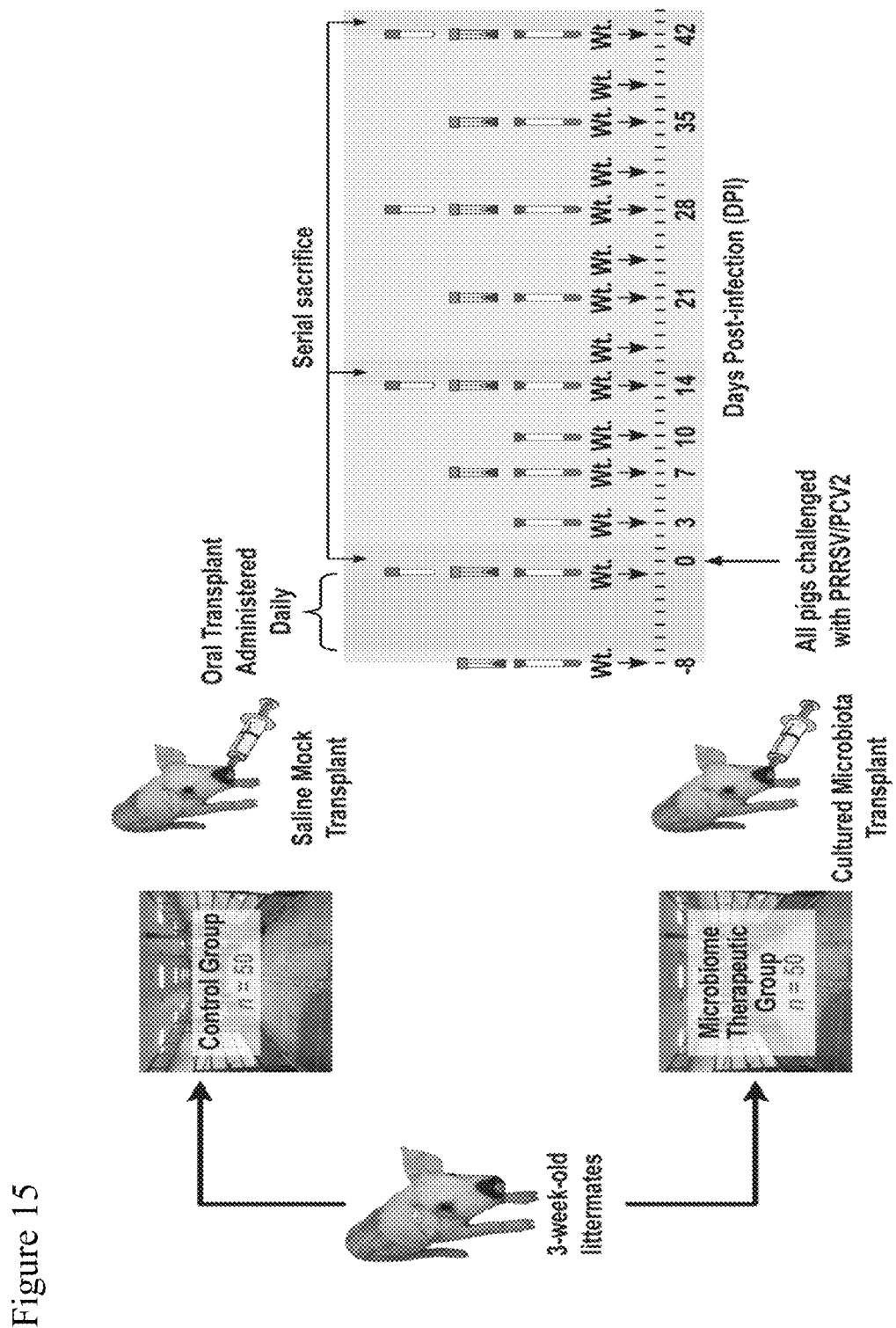
Figure 16:
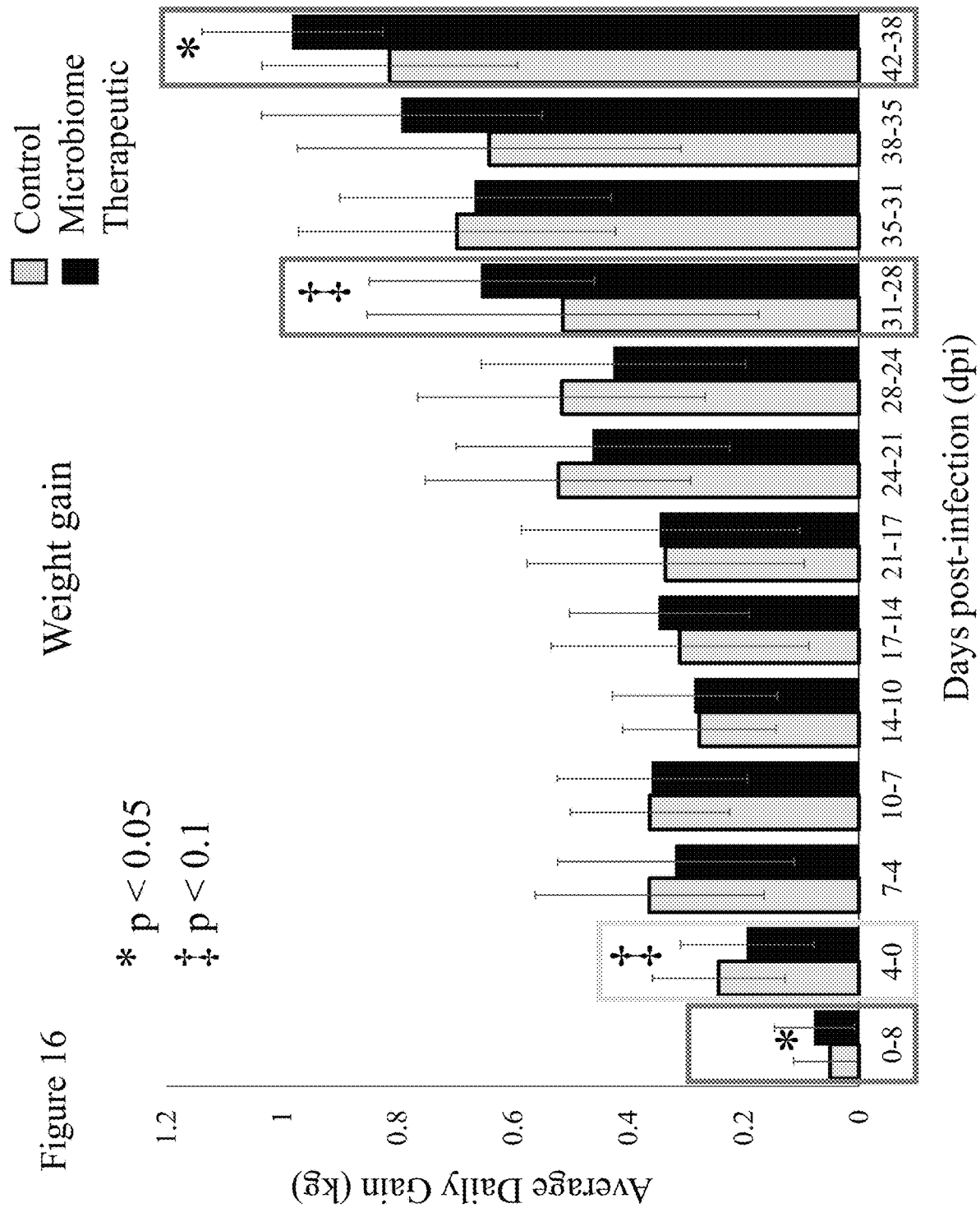
Figure 17:
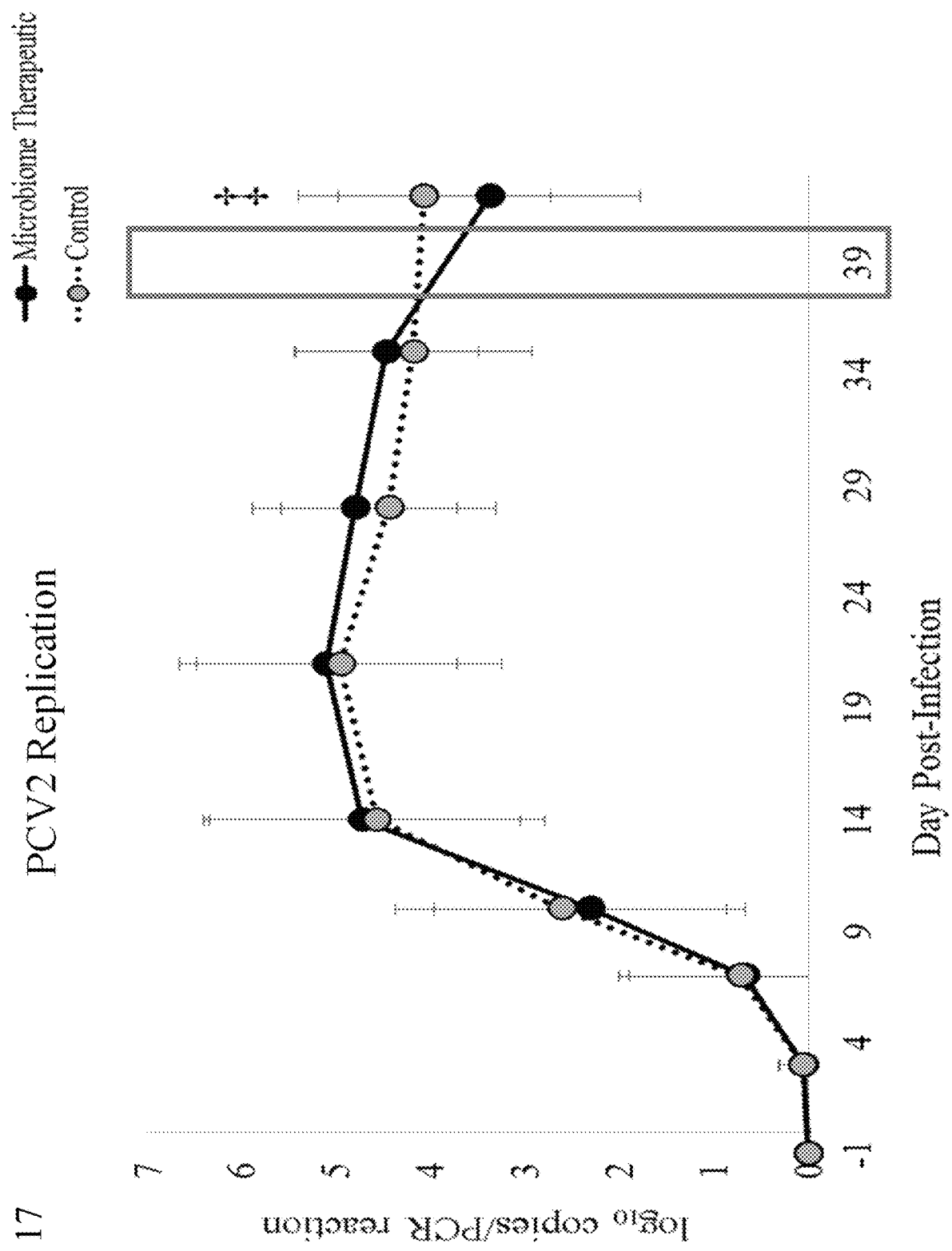
Figure 18:
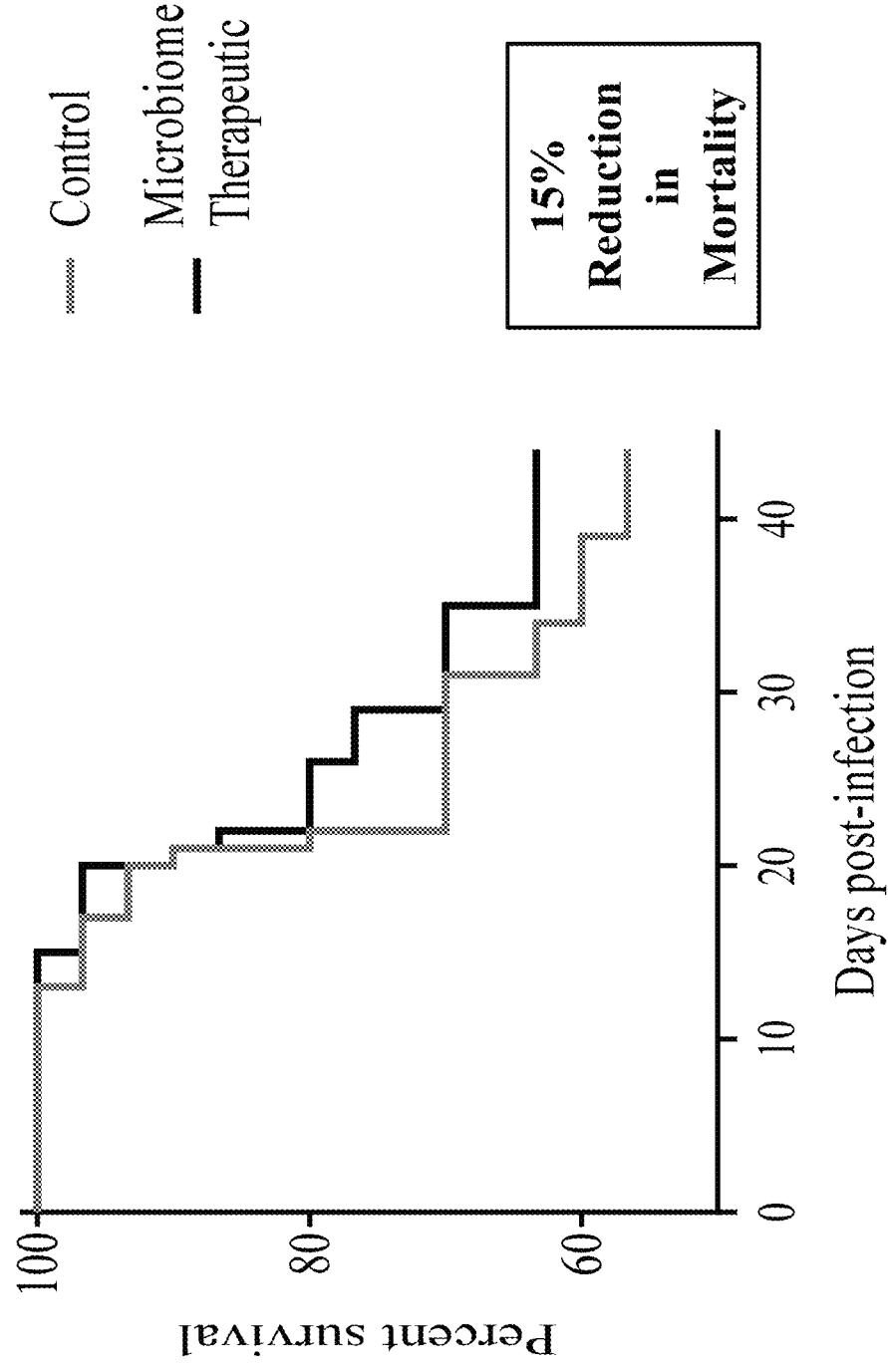
Figure 19:
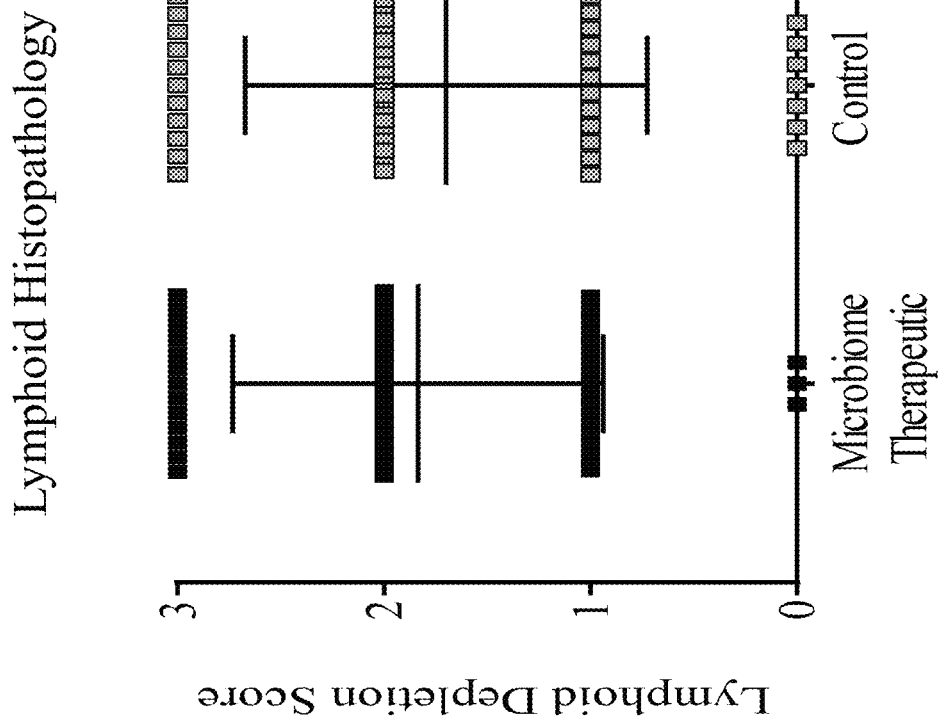
Figure 20:
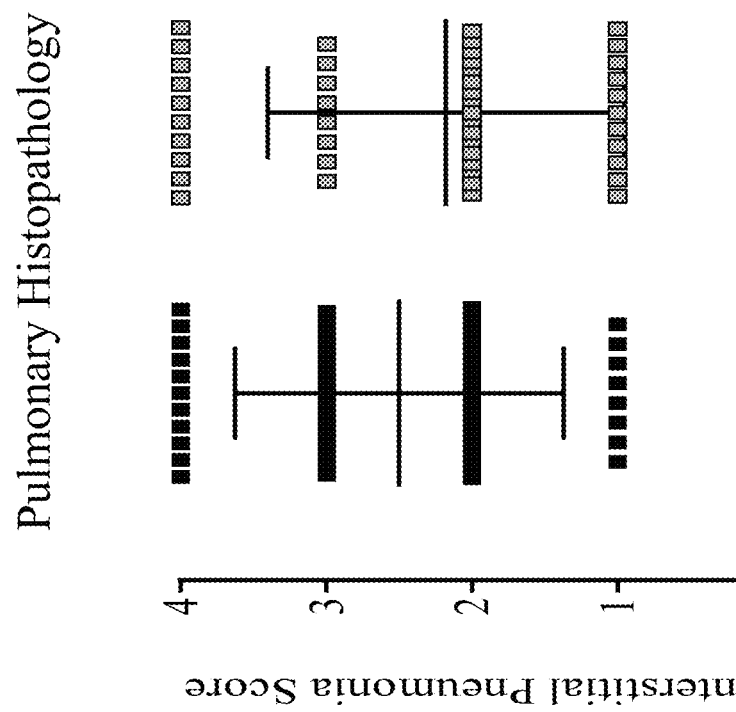
Figure 21:
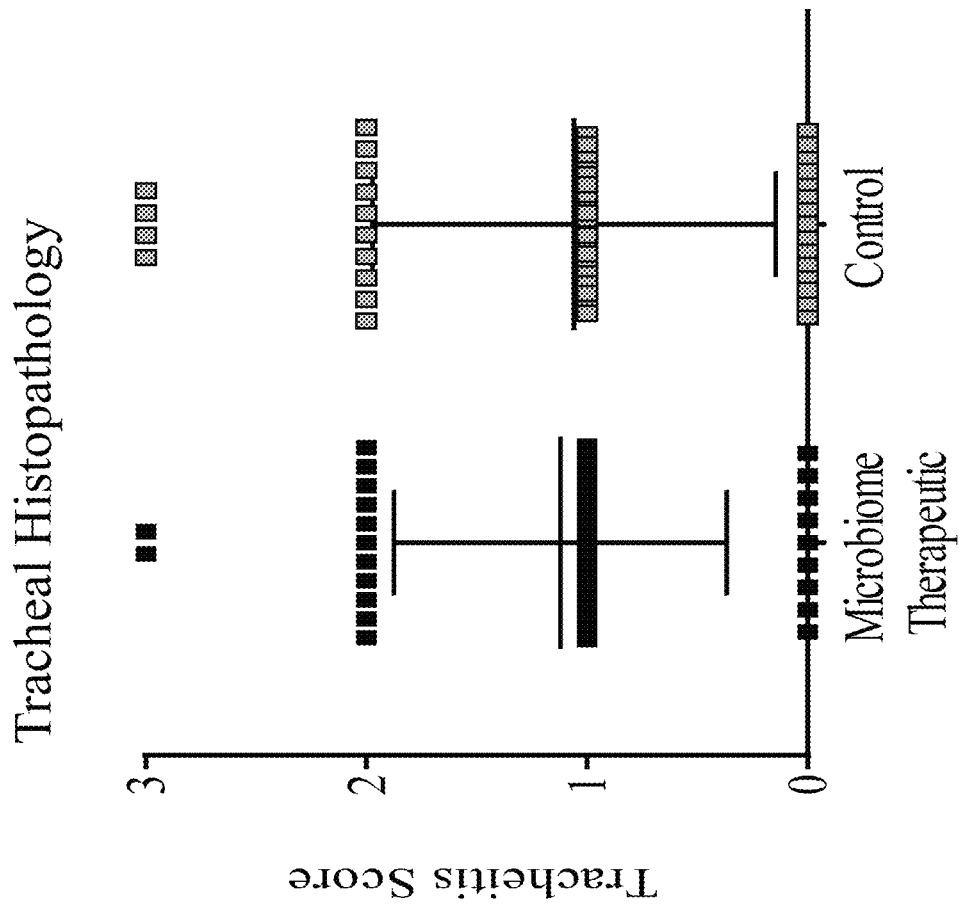

FIG. 4 is a set of 4 graphs illustrating the degree of lung and lymphoid lesions in pigs after co-infection with PRRSV and PCV2d. For A through D, data is shown as individual scores at the time of death with horizontal lines representing the mean±1 standard deviation for each group. Pigs shown in gray are those that died or were humanely euthanized due to severity of disease associated with PCVAD:

FIG. 4A illustrates gross lung affected by pneumonia as measured by the digital photo score. Mean percent of lung affected was lower in FMT (53.6±12.9) when compared to Controls (82.4±6.4; p=0.06, unpaired t-test);

FIG. 4B illustrates lung weight to body weight ratio at the time of necropsy. The control pigs had significantly higher ratios (p=0.037, unpaired t-test), likely the result of increased in cellular infiltrate and fluid in lung tissue at the time of death;

FIG. 4C illustrates lymphoid depletion that was scored from 0-3 with 0=no lymphoid depletion and 3=severe lymphoid depletion. Mean scores were higher in the control group (2.5±0.3) when compared to the FMT group (1.9±0.3), but differences were not statistically significant (p=0.155, Mann Whitney U test);

FIG. 4D illustrates lung lesions that were scored from 0-4 with 0=no lung lesions and 4=severe diffuse interstitial pneumonia with >75% lung lobe involvement. Mean scores were higher in the control group (3.3±0.3) when compared to the FMT group (2.7±0.3), but differences were not statistically significant (p=0.164, Mann Whitney U test);

FIG. 5 is a set of 8 graphs illustrating the time course of PRRSV and PCV2d viremia. Data is shown as the $\log_{10}$ copy number per PCR reaction for individual pigs in both the control and FMT groups;

FIG. 5A illustrates the time course of PRRSV for pigs in the control group. Gray boxes indicate pigs that died or were humanely euthanized during the course of the co-infection trial due to severity of disease;

FIG. 5B illustrates the time course of PRRSV for pigs in the FMT group. Gray boxes indicate pigs that died or were humanely euthanized during the course of the co-infection trial due to severity of disease;

FIG. 5C illustrates and compares the time course of PRRSV for the groups of pigs in 5A and 5B. Data is shown as mean $\log_{10}$ copy number per PCR reaction ±1 standard deviation for each group. Asterisks demarcate statistically significant differences for PRRSV (p=0.02, repeated measures analysis using multiple t-tests) for 7 and 21 dpi, respectively;

FIG. 5D illustrates the time course of PCV2d for pigs in the control group. Gray boxes indicate pigs that died or were humanely euthanized during the course of the co-infection trial due to severity of disease;

FIG. 5E illustrates the time course of PCV2d for pigs in the FMT group. Gray boxes indicate pigs that died or were humanely euthanized during the course of the co-infection trial due to severity of disease;

FIG. 5F illustrates and compares the time course of PCV2d for the groups of pigs in 5D and 5E. Data is shown as mean $\log_{10}$ copy number per PCR reaction ±1 standard deviation for each group. Asterisks demarcate statistically significant differences for PCV2d (p=0.02 and p=0.03 for 7 and 21 dpi, respectively; repeated measures analysis using multiple t-tests);

FIG. 5G illustrates PRRSV in PCVAD affected pigs. Data is shown as PRRSV viremia in PCVAD-affected (circles) and PCVAD-unaffected (squares) pigs within the control and FMT groups, as measured by mortality and clinical disease;

FIG. 5H illustrates PCV2d in PCVAD affected pigs. Data is shown as PCV2 viremia in PCVAD-affected (circles) and PCVAD-unaffected (squares) pigs within the control and FMT groups, as measured by mortality and clinical disease;

FIG. 6 is a set of three graphs that illustrate the detection of antibody in transplanted and control pigs. Data is shown as the mean sample:positive ratio ±1 standard deviation. Differences between the two group are shown as *p<0.03 and ‡p<0.06 (repeated measures analysis using multiple t-tests);

FIG. 6A illustrates the detection of antibody for PRRSV (A);

FIG. 6B illustrates the detection of antibody for PCV2 large epitope;

FIG. 6C illustrates the detection of antibody for PCV2 decoy epitope;

FIG. 7 is a set of two graphs illustrating fecal microbiome composition as detected by the pan-microbial array in FMT and control pigs after 7 days of transplantation;

FIG. 7A illustrates the microbiome family composition as the percent of FMT pigs (n=10) and control pigs (n=10) with each family detected on the pan-microbial array. Families with a total prevalence of less than 40% between the FMT and control groups are not shown. There was a significantly higher prevalence of a species within the family Intrasporangiaceae in the FMT group (*p=0.03; Fisher's exact test). A trend towards a higher percentage of control pigs having species within the family Synergistaceae was also detected (‡p=0.07; Fisher's exact test);

FIG. 7B illustrates the data as the mean number of species detected ±one standard deviation in each family detected in FMT and control pigs. Within the families Spirochaetaceae and Vibrionaceae, there was greater species diversity in the control group compared to the transplanted group (*p=0.01 and p=0.02, respectively; Mann Whitney U test). ‡ Indicates families found in the transplant material;

FIG. 8 is a series of 3 graphs illustrating 16S rDNA fecal microbiome analysis pre and post fecal microbiota transplantation;

FIG. 8A illustrates Chao1 alpha diversity of the control and transplanted groups pre and post-transplantation (data is shown as the range of values with medians, quartiles and outliers);

FIG. 8B provides bar graphs showing the mean relative abundance of bacterial phyla for each group and time;

FIG. 8C provides bar graphs showing the mean relative abundance of bacterial families making up 1% or more of all sequences detected in 1 or more sample subset;

FIG. 9 illustrates differentially abundant operational taxonomic units (OTU) in the control and FMT groups after 7 days of fecal microbiota transplantation. In the FMT group, 73.3% of the differential OTUs belong to the Veillonellaceae, Lachnospiraceae, and Ruminococcaceae families, and 13.3% of the OTUs were not classified at the family level. For the control group, 40% of the differential OTUs belong to Erysipelotrichaceae, Lachnospiraceae and Ruminococcaceae families and 33.3% of the differential OTUs were unclassified. Interestingly, the hierarchical clustering of the differential OTUs show two major clusters for each of the control and FMT groups;

FIG. 10 is a set of two graphs illustrating fecal bacterial diversity in the PCVAD-affected and unaffected pigs at the time of challenge;

FIG. 10A illustrates Chao1 alpha diversity;

FIG. 10B illustrates observed OTUs for the affected and unaffected pigs after transplantation or mock-transplantation (data is shown as the range of values with medians, quartiles and outliers). PCVAD-affected pigs developed disease and were euthanized or died due to severity of clinical signs during the 42-day post-infection trial;

FIG. 11 illustrates the microarray detection of microbes in serum 70 days after co-infection with PCV2 and PRRSV. Percent of best clinical outcome pigs (n=10, open bars) and worst clinical outcome pigs (n=10, black bars) are shown for each microbe detected on the array. Asterisks identify statistically significant differences between groups (p=0.02, Fisher's exact test);

FIG. 12 illustrates the microarray detection of microbes in lungs 70 days after co-infection with PCV2 and PRRSV. Percent of best clinical outcome pigs (n=10, open bars) and worst clinical outcome pigs (n=10, black bars) are shown for each microbe detected on the array. No significant differences were detected between groups. ND=not detected;

FIG. 13 illustrates the microarray detection of microbes in feces 70 days after co-infection with PCV2 and PRRSV. Percent of best clinical outcome pigs (n=10, open bars) and worst clinical outcome pigs (n=9, black bars) are shown for each microbe detected on the array. Asterisks identify statistically significant differences between groups (p=0.03, Fisher's exact test). ND=not detected;

FIG. 14 illustrates the fecal microbiome diversity in pigs with the best and worst clinical outcomes. Data is shown as the total number of microbial families detected by DNA microarray 70 days after co-infection with PRRSV and PCV2. Group means and standard deviations are represented by horizontal lines. The number of microbial families detected in feces were significantly different between the best and worst outcome groups (*p=0.017, Mann-Whitney U-test);

FIG. 15 is schematic representation of the experimental design for Example 5;

FIG. 16 is a graph comparing the average daily weight gain between the control group and the microbiome therapeutic group of Example 5;

FIG. 17 is a graph comparing the PCV2 replication between the control group and the microbiome therapeutic group of Example 5;

FIG. 18 is a graph comparing the mortality rates between the control group and the microbiome therapeutic group of Example 5;

FIG. 19 is a graph comparing the pulmonary histopathology between the control group and the microbiome therapeutic group of Example 5;

FIG. 20 is a graph comparing the lymphoid histopathology between the control group and the microbiome therapeutic group of Example 5; and FIG. 21 is a graph comparing the tracheal histopathology between the control group and the microbiome therapeutic group of Example 5.

DETAILED DESCRIPTION

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and preceded with the word "a" or "an" or "the" or "said" should be understood as not excluding plural elements or steps, unless such exclusion is explicitly recited. The terms "comprising", "including", and "having" are intended to be inclusive and mean that there may be additional elements other than the listed elements.

EXAMPLES

The use of animals and viruses in research was performed in accordance with the Federation of Animal Science Societies (FASS) Guide for the Care and Use of Agricultural Animals in Research and Teaching, the USDA Animal Welfare Act and Animal Welfare Regulations, and approved by the Kansas State University Institutional Animal Care and Use Committees and Institutional Biosafety Committees.

Example 1

Materials and Methods

Animals and housing: Ten pairs of barrow siblings (n=20; 24 days of age upon arrival) were obtained at weaning from a single high health commercial source negative for PRRSV, *Mycoplasma hyopneumoniae* and porcine epidemic diarrhea virus (PEDV). Sibling pairs were from 10 different sows. The piglets were not vaccinated for PCV2 and were utilized without regards to maternal antibody. No prophylactic or therapeutic antibiotics were administered at weaning or within 1 week of arriving at Kansas State. All pigs were housed in two identical environmentally controlled rooms at the Kansas State University Large Animal Research Center and maintained under biosafety level 2 (BSL-2) conditions. Each sibling pair was divided into either the control or fecal microbiota transplant (FMT) group; the two groups were balanced according to arrival weight. Pigs were housed in groups of 10 in a 98.2 sq ft pen with raised slatted flooring. All pigs were given approximately 24 hours to acclimate to their new environment prior to FMT or mock-transplant treatment. Pigs were given access to food and water ad libitum.

Viruses: The PRRS virus used to prepare the inoculum for this study originated from the lymph node of a pig with severe postweaning multisystemic wasting syndrome (PMWS) as previously described. PRRSV (isolate KS62; GenBank accession no. KM035803) was isolated by propagation on MARC-145 cells. PRRSV titration was also performed on MARC-145 cells. Briefly, PRRSV infectivity was titrated through serial 10-fold dilutions of PRRS stock virus in minimal essential medium (MEM; Corning) supplemented with 7% fetal bovine serum (FBS; Sigma-Aldrich), penicillin-streptomycin (Pen Strep; 80 U/mL and 80 µg/mL, respectively; Gibco), 3 µg/mL amphotericin B (Fungizone; Gibco), and 25 mM HEPES (Life Technologies). The dilutions were added in quadruplicate to confluent MARC-145 cells in a 96-well tissue culture plate (BD Falcon). Following a 4-day incubation at 37° C. in 5% CO2, cells were examined for PRRSV-induced cytopathic effects. The median tissue culture infective dose (TCID50/mL) was calculated using the Spearman-Karber method.

The PCV2d virus was a field-derived isolate. Serum containing the field isolate was heat-treated to remove heat-labile pathogens and was subsequently used to infect cesarean-derived, colostrum-deprived (CD/CD) pigs. Lung, spleen and liver samples were collected from the CD/CD pigs at 21 days post-infection (dpi) and tested by qPCR for PCV2d. Cycle threshold (Ct) values of the tissues used to create the inoculum for the current study were 14.9, 14.2 and 14.2 for liver, lung and spleen, respectively, from a single CD/CD pig. A 10% tissue homogenate was created from the described tissues in Eagle's minimum essential medium (EMEM; Sigma-Aldrich) supplemented with 50 μg/mL gentamicin. Following centrifugation at 100×g for 15 min at 4° C., the supernatant was heat-treated at 55° C. for 45 min to inactivate heat-labile pathogens. Analysis of the supernatant using the LLMDA confirmed the inoculum was negative for other common pathogens, such as porcine parvovirus, PRRSV, swine influenza virus, and *Mycoplasma hyopneumoniae*, but remained positive for porcine endogenous retroviruses (data not shown), which are ubiquitous in swine. PCV2d infectivity was titrated on swine testicle (ST) cells. Briefly, serial 10-fold dilutions of PCV2d challenge stock were added in quadruplicate onto rapidly dividing ST cells in a 96-well tissue culture plate (BD Falcon). Dilutions were prepared in Eagle's minimal essential medium (EMEM; Sigma-Aldrich) supplemented with 7% fetal bovine serum (FBS; Sigma-Aldrich) and 50 μg/mL gentamicin (Lonza). Following a 3-day incubation at 37° C. in 5% CO2, cells were fixed and permeabilized with 80% acetone. Cells were then stained with a polyclonal anti-PCV2b primary antibody and a fluorescein (FITC) AffiniPure Goat Anti-Swine IgG secondary antibody (Jackson ImmunoResearch Laboratories, Inc.). Infected cells were visualized using an inverted fluorescent microscope and the 50% tissue culture infective dose (TCID50/mL) was calculated using the method of Spearman and Karber (Finney, 1964).

To prepare the inocula for pigs, the stock viruses were mixed to yield a 2-mL dose consisting of $10^4$ $TCID_{50}$ PCV2d and $10^5$ $TCID_{50}$ PRRSV in MEM. The 2-mL dose was split, with 1 mL being delivered intranasally and 1 mL being delivered intramuscularly.

Fecal microbiota transplant: Two sows from a commercial farrow-to-wean farm in Kansas were selected as donors for the transplant material. This herd was negative for PRRSV and had recently undergone a *Mycoplasma hyopneumoniae* elimination program. The two sows were selected based on several characteristics, including older age (average age 4.8 years), high parity (9 and 12 litters born prior to donation), large litters with a high percentage of born alive piglets (15.1±2.0 total born; 95% born alive), low pre-weaning mortality, no history of fetal mummification, and no antibiotic treatment received within at least the last 15 months prior to donation. Pre-weaning mortality in these two sows was primarily attributed to crushing injuries. Lifetime number of weaned pigs was 101 and 131 for each sow, respectively. For this study, feces were collected during lactation and sows had not yet weaned their respective litters at the time. Feces were initially screened and confirmed as negative for gastrointestinal parasites using a fecal float qualitative exam by the Kansas State Veterinary Diagnostic Laboratory (KSVDL).

To prepare the FMT, fresh feces was collected naturally during defecation or manually from the rectum of the two sows. Feces were processed within approximately 3 hours after collection, during which the fecal microbiota was concentrated and stored using a protocol adapted from the human FMT literature. Specifically, feces were weighed into 50 gram aliquots and mixed in a standard commercial blender (Oster, Sunbeam Products Inc.) with 250 mL of sterile saline (0.9% sodium chloride irrigation USP, Braun Medical) until homogenized. The fecal slurry was then passed progressively through 2.0, 1.0, 0.5, and 0.25 mm stainless steel sieves into a sieve receiver (Fisherbrand™). The filtered liquid was collected, aliquoted into 50 ml tubes, and centrifuged at 6,000×g for 15 minutes. The supernatant was discarded and each bacterial pellet was resuspended in approximately 20 mL of sterile saline. All resuspensions were gently vortexed prior to mixing the concentrated microbiota in a large beaker. Glycerol (molecular biology reagent grade, MP Biomedicals™) was added to create a 10% glycerol suspension and the transplant material was stored at −80° C. until the day of transplantation. On the day of transplantation, the FMT material was thawed for 2 hours on ice and kept cold prior to administration.

The FMT material was submitted to KSVDL for routine bacterial culture, including aerobic culture, anaerobic culture and *Salmonella* enrichment. Species identification was attempted for all bacteria cultured. The FMT material was also fully characterized on the Lawrence Livermore Microbial Detection Array.

Experimental design and sample collection: Approximately 24 hours after arriving at Kansas State University, pigs were administered a fecal microbiota transplant (FMT) or a mock transplant (CONTROL). Mock transplants were made of 10% glycerol in sterile saline. To administer the FMT or mock-transplant, 5 mL doses were delivered through flexible dispensing tips (6.4 mm Flexoject™ Dispensing Tips, Innovet). Solutions were delivered slowly on the tongue or in the cheek pouch, allowing the pig to chew on the tip and naturally consume the material over 30 seconds to 1 minute. Transplants or mock-transplants were administered daily for seven consecutive days prior to co-infection.

At approximately 4.5 weeks of age (32 days), all 20 pigs were infected with PRRSV and PCV2d. Body weights of individual pigs were collected upon arrival (−8) and on −7, 0, 7, 14, 21, 24, 28, 32, 35, and 42 dpi. Blood samples were collected from all pigs on −7, 0, 4, 7, 11, 14, 21, 28, 35, and 42 dpi. Fecal samples were collected from all 20 pigs on −7 and 0 dpi. In addition to these planned sample collection times, blood, feces and weights were collected on the day of death or euthanasia. Pigs were humanely euthanized under the direction of the attending laboratory animal veterinarian if 1) pigs had greater than or equal to 20% weight loss, 2) pigs were moribund or nonresponsive to veterinary treatment, or 3) pigs had severe dyspnea or clinical disease that compromised animal welfare. At 42 dpi, all remaining pigs were humanely euthanized in accordance with the American Veterinary Medical Association Guidelines for the Euthanasia of Animals and complete necropsies were performed.

Clinical and pathologic evaluation: All pigs were assessed daily for the presence of clinical signs associated with PRRSV/PCV2 co-infection, such as dyspnea, tachypnea, ocular discharge or conjunctivitis, coughing or sneezing, nasal discharge, aural cyanosis, open mouth breathing, decreased body condition, muscle wasting, rough hair coat, lethargy, depression, joint effusion, lameness, diarrhea, and pallor or jaundice. Pigs were visually examined by a veterinarian or veterinary assistant on each day of the study period. Under the direction of the attending veterinarian, appropriate treatments were administered to pigs with moderate to severe clinical disease. Examples of clinical presentations where treatment was administered included 1) dyspnea and/or tachypnea, 2) mucoid rhinorrhea, 3) conjunctivitis with swelling, 4) pallor or jaundice with muscle wasting, and 5) lethargy or depression with pyrexia. Clinically affected pigs were prescribed parenteral antibiotics, such as ceftiofur hydrochloride or oxytetracycline. Any pig with overt clinical disease and a rectal temperature of ≥104° F. was administered parenteral flunixin meglumine, a non-steroidal anti-inflammatory drug. Other supportive care, such as oral or subcutaneous fluids, were administered for significantly dehydrated pigs under the direction of the attending veterinarian. Pigs with evidence of conjunctivitis were treated with triple antibiotic ophthalmic ointment (bacitracin-neomycin-polymyxin, Vetropolycin, Dechra). Clinical signs and treatments unrelated to PRRSV or PCVAD (e.g., lacerations, dermatitis, congenital hernias, etc.) were documented and monitored but were not included in the data analysis related to clinical outcome. Treatment days were numerated for individual pigs over time. Treatment days were counted as each day a pig was prescribed a parenteral therapeutic. Mortality rate was calculated from those pigs that died or were euthanized prior to the 42-day termination of the study. Morbidity rate was calculated as the number of pigs demonstrating clinical signs that required parenteral therapy.

At 42 dpi, all surviving pigs were humanely euthanized with intravenous pentobarbital sodium. A board certified veterinary pathologist, blinded to the source of the pigs, performed complete necropsies and histopathology. First, whole body weights were collected post-mortem. Second, lungs and trachea were removed in toto immediately after euthanasia and total lung weights were measured. The trachea was excised immediately distal to the larynx. Lung weight to body weight ratio was calculated as a measure of pulmonary pathology. Dorsal and ventral aspects of the whole lung were photographed (Canon EOS Rebel T6 DSLR) and digital images were evaluated after gross necropsy using a photo scoring system. Gross anatomical photo scores were reported as the percentage of whole lung affected by pneumonia (ranging from 0 to 100%). Scores were combined from 5 sections of the lung as previously described (Halbur et al., 1995), including 1) right dorsal lung—25%, 2) left dorsal lung—25%, 3) right ventral lung—22.5%, 4) left ventral lung—22.5%, and 5) accessory lung lobe—5%. The photos were evaluated by a board certified veterinary pathologist who was blinded to the source of the lung pictures.

Tissues collected for histopathology included lung (1 section from each lobe) and tracheobronchial lymph node. Additional tissues were collected at the pathologist's discretion by evidence of gross lesions. Tissues were fixed in 10% neutral buffered formalin for at least 7 days, routinely processed in an automated tissue processor, embedded in paraffin, and stained with hematoxylin and eosin (H&E stain). Microscopic lung lesions were scored using a 0-4 system. Scores were assigned as follows: 0, no significant lung lesions; 1, mild multifocal interstitial pneumonia with <50% lung lobe involvement; 2, mild to moderate multifocal interstitial pneumonia with 50-75% lung lobe involvement; 3, moderate to severe multifocal interstitial pneumonia with 50-75% lung lobe involvement; 4, severe diffuse interstitial pneumonia with >75% lung lobe involvement. Degree of lymphoid depletion was scored using a 0-3 system. Scores were assigned as follows: 0, no lymphoid depletion; 1, mild or small amount of lymphoid depletion; 2, moderate or intermediate amount of lymphoid depletion; 3, severe or large extent of prominent lymphoid depletion.

PCV2 immunohistochemical staining: PCV2 antigen staining in paraffin-embedded tissue thin sections was performed by personnel in the Kansas State Veterinary Diagnostic Laboratory. Briefly, deparaffinized slide-mounted thin sections were first treated with proteinase K (1.2 mg/ml diluted in Bond Enzyme Diluent with 0.35% ProClin 950) for 10 minutes at room temperature (Bond Enzyme Pretreatment Kit, Leica Biosystems). Rabbit anti-PCV2 antibody (Iowa State University) was diluted at 1:500 in PowerVision IHC/ISH Super Blocking (Leica Biosystems) and applied to the tissue section for 15 minutes at room temperature. Bound antibody was detected by incubation with 25 µg/ml Poly-AP anti-rabbit IgG (Leica Biosystems) in antibody diluent for 25 minutes at room temperature. The complex was visualized using Fast Red chromogen (Bond Polymer Refine Red Detection Kit, Leica Biosystems) and counterstained with hematoxylin.

Measurement of PRRSV and PCV2 viremia: Viral DNA and RNA was extracted simultaneously from 50 µL of serum using Ambion's MagMAX 96 Viral Isolation Kit (Applied Biosystems) in accordance with the manufacturer's instructions. PRRS viral RNA was quantified using EZ-PRRSV MPX 4.0 Real Time RT-PCR Target-Specific Reagents (Tetracore) according to the manufacturer's instructions. For consistency, each plate contained Tetracore Quantification Standards and Control Sets for use with EZ-PRRSV MPX 4.0 RT-PCR Reagents. All PCR reactions were carried out on a CFX96 Touch Real-Time PCR Detection System (Bio-Rad) in a 96-well format using the recommended cycling parameters. The PCR assay results were reported as log 10 PRRSV RNA starting quantity (copy number) per 50 µL reaction volume.

PCV2d DNA was quantified using SsoAdvanced Universal SYBR green supermix (Bio-Rad). Briefly, forward and reverse PCR primers were 5'-AATGCAGAGGCGTGAT-TGGA-3' (SEQ ID NO. 1) and 5'-CCAGTATGTGGTTTCCGGGT-3' (SEQ ID NO. 2), respectively, and were used at a final concentration of 300 µM. Standard curves and positive and negative controls were included on each plate. Plasmid DNA was used for the PCV2 standard curve and positive control template. DNA inserted into the plasmid was obtained from a field strain of PCV2 (PCV2b 321/393). The PCV2 PCR was carried out on a CFX96 Touch Real-Time PCR Detection System using the following settings: activation at 98° C. for 2 minutes, followed by 40 cycles of denaturing at 98° C. for 5 seconds and annealing/extension at 60° C. for 10 seconds. The PCR assay results were reported as log 10 PCV2 DNA starting quantity (copy number) per 50 µL reaction volume.

Microsphere immunoassay for detection of PRRSV and PCV2 antibodies: PRRSV nucleocapsid protein and PCV2b capsid protein fragments (43-233 and 160-233) (sequence positions correspond to Genbank accession #HQ713495) were cloned into the pHUE expression vector. For protein expression, bacteria were grown in Luria-Bertani (LB) broth plus ampicillin (0.01 mg/ml) and incubated at 37° C. with shaking. Once the OD600 reached 0.4-0.6, protein expression was induced by adding 1 ml of 0.1M isopropyl β-D-1-thiogalactopyranoside (IPTG) to the culture and bacteria were harvested 4 hours later. Bacteria were pelleted by centrifugation at 4,000×g for 10 min. Soluble proteins were purified using the USB PrepEase Histidine-tagged Protein Purification Kit (Affymetrix) under non-denaturing conditions, according to the manufacturer's directions. Purity was assessed by SDS-PAGE and total protein measured using the Bio-Rad Protein Assay.

Proteins were coupled to carboxylated Luminex MagPlex® polystyrene microspheres according to the manufacturer's directions. For the assay, approximately 2500 antigen-coated beads, suspended in 50 µL PBS with 0.05% Tween-20 and 4% goat serum (PBST-GS), were placed in each well of a 96-well polystyrene round bottom plate (Costar). Sera were diluted 1:400 in PBST-GS and 50 µL was added to each well. The plate was sealed and incubated for 30 min at room temperature with gentle shaking. After the incubation, the plate was placed on a magnet and beads were washed three times with 190 µL of PBST-GS. For the detection of IgG, 50 µL of biotin-SP-conjugated affinity purified goat anti-swine secondary antibody (IgG, Jackson ImmunoResearch) was diluted to 2 µg/mL in PBST-GS and 100 µl was added to each well. The plate was incubated at room temperature for 30 min and washed three times followed by the addition of 50 µL of streptavidin-conjugated phycoerythrin (2 ug/ml in PBST-GS; SAPE). After 30 min, the plate was washed and microspheres resuspended in 100 µL of PBST-GS. Microspheres were analyzed using a MAG-PIX instrument (Luminex) and Luminex® xPONENT 4.2 software. A minimum of 50 microspheres was used for the calculation of mean fluorescence intensity (MFI). The sample to positive (S/P) ratio was calculated as the MFI of sample minus MFI of negative control divided by MFI of standard positive control minus MFI of negative control.

Microarray analysis of FMT and fecal samples: The Lawrence Livermore Microbial Detection Array (LLMDA) was used to analyze microbiome composition and diversity of the transplant material and fecal samples. This array detects annotated sequences of microbes associated with infection of vertebrates within GenBank®, the National Institute of Health genetic sequence database. The version 7 of the LLMDA in the 4plex 180K probe format was used in this study. This version of the array targets 4,377 viruses, 5,457 bacteria, 327 archaea, 319 fungi, and 132 protozoa. The LLMDA oligonucleotide probes vary between 50 and 65 nucleotides in length and have roughly equivalent affinities for their complementary target DNA molecules. Probes were designed to detect all sequenced microbial families with a large number of probes per sequence (average of 30 probes) to improve sensitivity in the evaluation of microbial nucleic acids in a variety of samples. The high-density oligo LLMDA microarray and statistical analysis method have been extensively tested in numerous studies for viral and bacterial detection in pure or complex environmental and clinical samples.

The PowerViral™ Environmental RNA/DNA Isolation Kit (MO BIO, San Diego, Calif.) was used to extract DNA and RNA from the fecal samples. For each sample, approximately 250 mg of feces was added to 600 µl of PV1/β-mercaptoethanol in a glass beat tube included in the kit. Samples were homogenized and lysed by vortexing tubes for 10 minutes at maximum speed. Samples were further processed using the PowerViral™ Kit protocol. All samples were eluted into 100 µl of RNase-Free water. The purified nucleic acids were quantified using the Thermo Scientific™ Nanodrop™ spectrophotometer. For each sample, 10 µl of the extracted DNA and RNA was amplified using the random amplification procedure. The amplified cDNA and DNA was purified with the Qiaquick PCR purification columns (Qiagen) and quantified using the Nanodrop™ spectrophotometer.

Approximately 1 µg of amplified cDNA and DNA were fluorescently labeled using a one-coloring labeling kit (Roche NimbleGen, Madison, Wis.). Briefly, the samples were labeled using nick translation with Cy3-labeled random nonamer primers (TriLink Biotechnologies, San Diego, Calif.) and Klenow DNA polymerase at 37° C. for 2 hr. The labeled DNA was precipitated in isopropanol, centrifuged for 10 min, and the pellet was washed and dried. The pellet was then reconstituted in 50 µl of RNase-Free water and quantified using the Nanodrop™ spectrophotometer.

The Agilent Technologies Oligo aCGH/ChIP-on-Chip Hybridization kit (Santa Clara, Calif.) was used to hybridize samples to the arrays. For each sample, 10 µg of fluorescently labeled DNA was mixed with blocking agent, hybridization buffer and nuclease free water. The samples were then denatured at 95° C. for 3 min, and incubated at 65° C. for 3 min. Each sample was then immediately loaded onto the array and hybridized for approximately 40 hr at 65° C. in a microarray rotator oven (Agilent Technologies Inc., Santa Clara, Calif.) set to a speed of 20. Microarrays were then washed using the standard manufacturer's protocol with Oligo aCGH/ChIP-on-chip Wash Buffer 1 for 5 min at room temperature and Oligo aCGH/ChIP-on-chip Wash Buffer 2 for 1 min at 37° C. (Agilent Technologies Inc., Santa Clara, Calif.). Using the SureScan Microarray Scanner (Agilent Technologies Inc., Santa Clara, Calif.), all arrays were scanned to a resolution of 3 µm.

Microarray data was generated from the microbe sequences using the CLiMax method developed at Lawrence Livermore National Laboratory, at a detection threshold of ≥99%. The log likelihood for each of the positive targets is estimated from the BLAST similarity scores of the array feature and target sequences, together with the feature sequence complexity and other covariates derived from BLAST results.

Diversity of the fecal samples was measured by calculating the number of families and species detected in each sample. The mean number of families and species in the control and transplant groups as well as the affected and unaffected groups were compared prior to (−7 dpi) and after (0 dpi) FMT. Microbiome composition was compared between these groups at the level of phylum, family and species.

16S rDNA analysis of fecal samples: Pig fecal samples were collected in cryovials and stored at −80° C. until shipment to the University of Nebraska-Lincoln for DNA extraction and bacterial community analysis. DNA was extracted using the manufacturer's protocol for Mag-Bind® Soil DNA 96 Kit (Omega Bio-tek, Inc.) with the following modifications: precipitation of nucleic acids was done by using sodium acetate, isopropanol and ethyl alcohol. 0.1× volumes of 10 mM sodium acetate was added to each sample tube, which were vortexed and later incubated on ice for 5 min. Subsequently, 1 ml of ice-cold isopropanol was added and samples were incubated at −80° C. overnight to precipitate the DNA. The following day, samples were centrifuged at 4° C. for 15 min at 16,000×g. The supernatants of the resulting samples were discarded and the nucleic acid pellet was washed with 0.5 ml of ice-cold 70% ethyl alcohol. The samples were centrifuged for 2 min at 13,000×g, the residual supernatant was discarded, and the nucleic acid pellet was air dried for 3 min. The nucleic acid pellet was dissolved in a 0.45 ml of Tris (10 mM, pH 8) and incubated for 1 hr at 4° C. For further purification of dissolved nucleic acids, the KingFisher (ThermoFisher Scientific) robot was used with reagents from the Mag-Bind® Soil DNA 96 Kit. The resulting DNA was used for the tag-sequencing of the V4 region of 16S rDNA using the universal bacterial primers. A 20 µL PCR reaction contained 1×Terra™ PCR Direct Polymerase Mix, 0.5 µL Terra polymerase, 20 mM of each primer, and 20-50 ng of DNA. The cycling conditions for PCR were the same as previously described (Paz et al., 2016). The PCR product size was confirmed by agarose gel electrophoresis. Normalization of the amplified PCR products were performed with Just-a-Plate™ 96 PCR Purification & Normalization kit (Charm Biotech, CA, USA) according to the manufacturer's protocol. Following normalization, 10 µL from each sample were pooled and concentrated using Nucleospin® Gel & PCR Cleanup kit (MACHEREY-NAGEL Gmbh & Co. KG, Duren, Germany) and was eluted using 20 µL of elution buffer. This pooled and purified sample was analyzed in a Agilent 2100 bioanalyzer (Agilent Scientific Instruments, CA, USA) using Agilent High Sensitivity DNA Kit (Agilent Technologies, Inc. Waldbronn, Germany) to ensure the quality and quantity of the targeted V4 region of 16S rDNA. The concentration of the DNA library was determined using the DeNovix QFX Fluorometer (DeNovix Inc. DE, USA) and using DeNovix dsDNA Fluorescence Quantification Assay (DeNovix Inc. DE, USA). The resulting 16S rDNA libraries were sequenced using the Illumina MiSeq platform utilizing the 2×250 paired end sequencing strategy using a MiSeq Reagent Kit V3 (Illumina Inc. CA, USA).

Data processing was performed on a custom pipeline utilizing several publicly available software tools. The paired-end reads were assembled into contigs after quality filtering using MOTHUR v.1.38.1 (Schloss et al., 2009). Operational taxonomic units (OTUs) were generated from the quality filtered sequences using the UPARSE pipeline (USEARCH v7.0.1090) at a threshold of 97% identity. Chimeric sequences were removed using the ChimeraSlayer gold.fa as the reference database using UCHIME (Edgar et al., 2011). OTUs were aligned against the v128 (SILVA) database and mismatched sequences were discarded. A phylogenetic tree was generated using high quality aligned sequences within MOTHUR v.1.38.1 using the Clearcut algorithm. Taxonomies to the identified OTUs were assigned using QIIME v.1.9.1 pipeline (Caporaso et al., 2010) with the Greengenes reference database (gg_13_5_otus). OTUs representing Archaea and Cyanobacteria were removed as Cyanobacterial reads may be a result of contamination of plant chloroplast and the archaea sequences may be biased as the primers used are not designed to universally amplify all archaea. Alpha diversity matrices (Chao1 and Observed OTUs) were calculated using the QIIME v.1.9.1 pipeline. The rarefaction of the OTU table was performed using QIIME v.1.9.1 with the lowest number of reads. For the experiment, 27035 was used as the lowest depth. The difference in bacterial communities (beta-diversity) among transplanted and control pigs was determined using the QIIME v.1.9.1 pipeline using distance matrices (weighted UniFrac, unweighted UniFrac and Bray Curtis) from the rarefied-OTU table.

Statistical analysis: For 16s rDNA sequencing, a three-way ANOVA (considering the effect of Treatment, Day and Animal) was performed on the Chao1 and Observed OTUs to estimate bacterial richness among the transplanted and control pigs with open source statistical software R (RCoreTeam, 2013). The overall bacterial community differences among treatments were determined by applying the permutational multivariate analysis of variance PERMANOVA on the weighted UniFrac distance matrix. Principal coordinate analysis (PCoA) was used on all distance matrices to generate plots which displayed global treatment effects. The PERMANOVA analysis was performed using R (RCoreTeam, 2015) (adonis function vegan package) in which treatment was considered as a fixed effect and animal (pig) as a random effect with the pig as the experimental unit. A core microbiome was determined for each treatment group by only selecting the OTUs present in 80% of the animals in each group (8/10). The core OTUs were used to identify differential OTUs between treatments using the linear discriminant analysis (LDA) effect size with LefSe. LefSe analysis was performed using default settings and differential OTUs from all pairwise comparisons to generate heatmaps in R (RCoreTeam, 2015).

All remaining statistical analyses were performed using GraphPad Prism 7.01 software (La Jolla, Calif.). Mean viremia, antibody levels, and weight measurements were compared between groups using repeated measures analysis with multiple unpaired t-tests. Survival curves were compared using the Mantel-Cox test and daily morbidity rates were compared using the Fisher's exact test. Microscopic lung and lymph node lesion scores were compared between groups using the Mann-Whitney U test. Gross photo scores and lung weight to body weight ratios were compared using the unpaired t-test. Microbiome diversity and number of species within family were compared between groups using the Mann-Whitney U test. Proportions of each group with individual species and families detected were compared using Fisher's exact test.

Results

Characterization of fecal transplant material: Several methods, including aerobic culture, anaerobic culture, microarray, and fecal float, were used to characterize the fecal microbiota transplant material. Fecal floatation for parasites confirmed feces were negative for parasites, including *Ascaris suum*, through standard diagnostic testing at KSVDL. Aerobic and anaerobic culture identified several culturable bacteria (Table 1) known to inhabit the gastrointestinal tract, including non-hemolytic *Escherichia coli, Bacillus altitudinis, Streptococcus alactolyticus, Enterococcus hirae*, non-hemolytic *Staphylococcus* sp., *Bacteroides vulgatus*, and *Clostridium perfringens*. Several additional anaerobic bacteria were cultured but unable to be identified at the genus or species level; these bacteria included gram negative coccobacilli, gram positive long rods, and large gram positive boxy rods. *Salmonella* enrichment culture was negative.

TABLE 1

| Bacteria detected in the fecal microbiota transplant by standard culture techniques |
|---|
| Aerobic culture |
| *Escherichia coli* (non-hemolytic) |
| *Bacillus altitudinis* |
| *Streptococcus alactolyticus* |
| *Enterococcus hirae* |
| *Staphylococcus* sp. (non-hemolytic) |
| Anaerobic culture |
| *Bacterioides vulgatus* |
| *Clostridium perfringens* (2 different colony types) |
| Gram negative unable to ID (gram negative coccobacilli) |
| Gram positive unable to ID (gram positive long rods) |
| Gram positive unable to ID (large gram positive boxy rods) |
| *Salmonella* enrichment |
| Negative |

The pan-microbial array detected the most diversity and absolute number of organisms, with 12 phyla, 33 microbial families and 49 microbial species detected (Table 2). Microbes were very diverse and from the phyla Actinobacteria, Amoebozoa, Bacteroidetes, Basidiomycota, Euryarchaeota, Firmicutes, Fusobacteria, Proteobacteria, Spirochaetes, Synergistetes, and Tenericutes. Additionally, a single virus was detected. The majority of species detected fell within the Proteobacteria phylum (16/49; 32.7%) with the second highest number of species falling with the Firmicutes phylum (9/49; 18.4%) and the third highest number of species falling within the Tenericutes phylum (6/49; 12.2%). Using the above methods, known swine pathogens were not detected.

TABLE 2

Microorganisms detected in the fecal microbiota transplant material by the pan-microbial detection array*

| Phylum‡ | Family | Genus Species |
|---|---|---|
| Actinobacteria | Bogoriellaceae | *Georgenia* sp. |
|  | Nocardiaceae | *Rhodococcus rhodnii* |
| Amoebozoa | Entamoebidae | *Entamoeba nuttalli* |
| Bacteroidetes | Bacteroidaceae | *Bacteroides graminisolvens*, *Bacteroidetes* bacterium |
|  | Cyclobacteriaceae | *Algoriphagus marincola* |
|  | Prevotellaceae | *Prevotella* sp. |
|  | Rikenellaceae | *Rikenella microfusus* |
| Basidiomycota | Ceratobasidiaceae | *Rhizoctonia solani* |
| Euryarchaeota | Methanobacteriaceae | *Methanobrevibacter oralis*, *Methanobrevibacter smithii* |
| Firmicutes | Carnobacteriaceae | *Alkalibacterium* sp. |
|  | Clostridiaceae | *Candidatus Clostridium anorexicamassiliense*, Clostridiaceae bacterium, *Clostridium* sp. |
|  | Clostridiales | Clostridiales bacterium |
|  | Lachnospiraceae | Lachnospiraceae bacterium |
|  | Lactobacillaceae | *Lactobacillus amylovorus* |
|  | Peptostreptococcaceae | *Clostridium bifermentans*, *Clostridium mangenotii* |
| Fusobacteria | Fusobacteriaceae | *Psychrilyobacter atlanticus* |
| Proteobacteria | Anaplasmataceae | *Candidatus Xenolissoclinum pacificiensis* |
|  | Bradyrhizobiaceae | *Bosea* sp., *Bradyrhizobium* sp. |
|  | Campylobacteraceae | *Campylobacter* sp., *Sulfurospirillum arcachonense* |
|  | Desulfovibrionaceae | *Desulfovibrio alkalitolerans* |
|  | Helicobacteraceae | *Helicobacter pametensis* |
|  | Legionellaceae | *Legionella lansingensis* |
|  | Piscirickettsiaceae | *Thiomicrospira kuenenii*, *Thiomicrospira* sp. |
|  | Pseudomonadaceae | *Pseudomonas* sp., *Rhizobacter* sp. |
|  | Sphingomonadaceae | *Sphingomonas* sp. |
|  | Vibrionaceae | *Candidatus Photodesmus katoptron* |
|  | Xanthomonadaceae | *Ignatzschineria larvae*, Xanthomonadaceae bacterium |
| Spirochaetes | Spirochaetaceae | *Borrelia parkeri*, *Spirochaeta* sp., *Treponema pedis*, *Treponema* sp. |
| Synergistetes | Synergistaceae | *Aminiphilus circumscriptus* |
| Tenericutes | Acholeplasmataceae | *Acholeplasma equifetale*, *Acholeplasma granularum* |
|  | Mycoplasmataceae | *Mycoplasma conjunctivae*, *Mycoplasma fermentans*, *Mycoplasma iowae* |
|  | Spiroplasmataceae | *Spiroplasma apis* |
| Virus | Circoviridae | Fur seal faeces associated circular DNA virus |

*Only those microbes identified at the phylum, family and genus level are included
‡Organized alphabetically by phylum; order listed when family unidentifiable FMT had no effect on pigs prior to co-infection: Upon arrival to Kansas State University, mean weight of the control group was 7.05±1.46 kg and mean weight of the FMT group was 7.07±1.39 kg (p=0.99, unpaired t-test using repeated measures; Table 3). No significant difference in weight gain was noted during the transplantation or mock-transplantation time period, suggesting no detrimental effect of FMT on weight gain in unchallenged conditions; mean weights for control pigs and FMT pigs on 0 dpi were 7.6±1.7 kg and 7.3±1.4 kg, respectively (p=0.85, unpaired t-test using repeated measures). FMT and control pigs appeared clinically within normal limits.

TABLE 3

Effect of FMT on weight gain prior to co-infection*

| Weight on arrival (−8 dpi) | | Weight after 7 days of FMT (0 dpi) | |
|---|---|---|---|
| Control | FMT | Control | FMT |
| 4.73 | 5.41 | 5.09 | 5.32 |
| 5.05 | 5.59 | 5.23 | 5.77 |
| 5.82 | 5.82 | 5.86 | 6.05 |
| 6.77 | 5.91 | 7.50 | 6.23 |
| 7.27 | 6.14 | 7.91 | 6.64 |
| 7.36 | 8.23 | 8.23 | 8.27 |
| 7.64 | 8.23 | 8.41 | 8.45 |
| 8.27 | 8.32 | 8.59 | 8.45 |
| 8.73 | 8.45 | 9.59 | 8.68 |
| 8.91 | 8.64 | 9.64 | 8.95 |
| Mean: 7.05 | Mean: 7.07 | Mean: 7.60 | Mean: 7.28 |
| SD: 1.46 | SD: 1.39 | SD: 1.67 | SD: 1.40 |
| p = 0.99 | | p = 0.85 | |

*Data is shown in kg. Statistics performed by unpaired t-tests using repeated measures analysis.

Figure 1A:
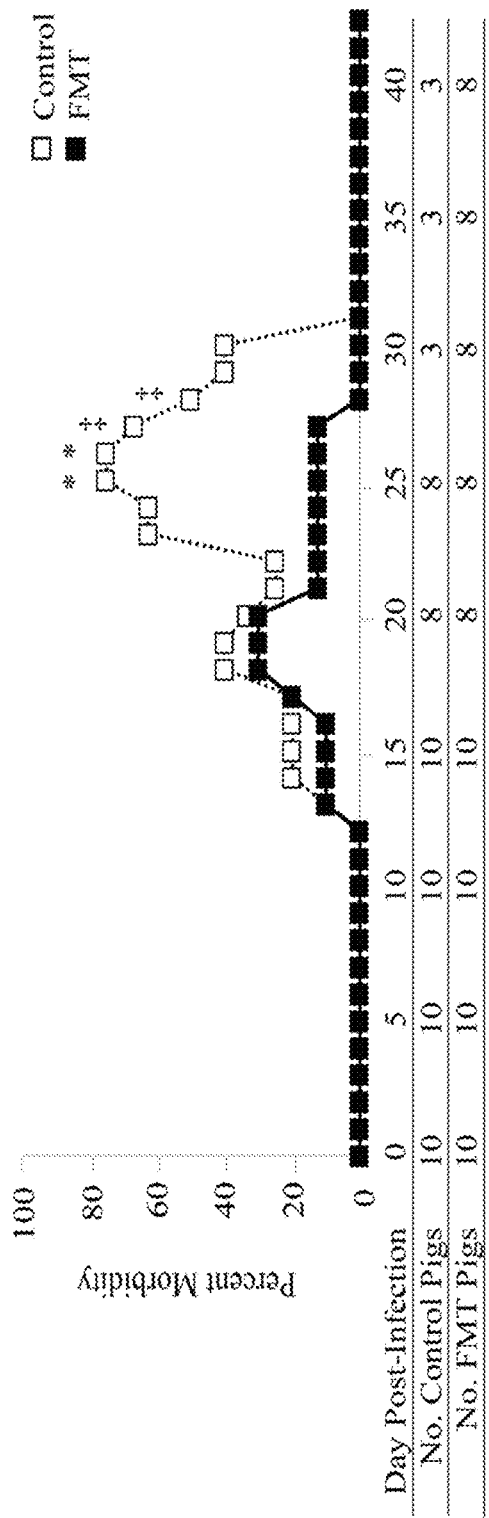
Figure 1B:
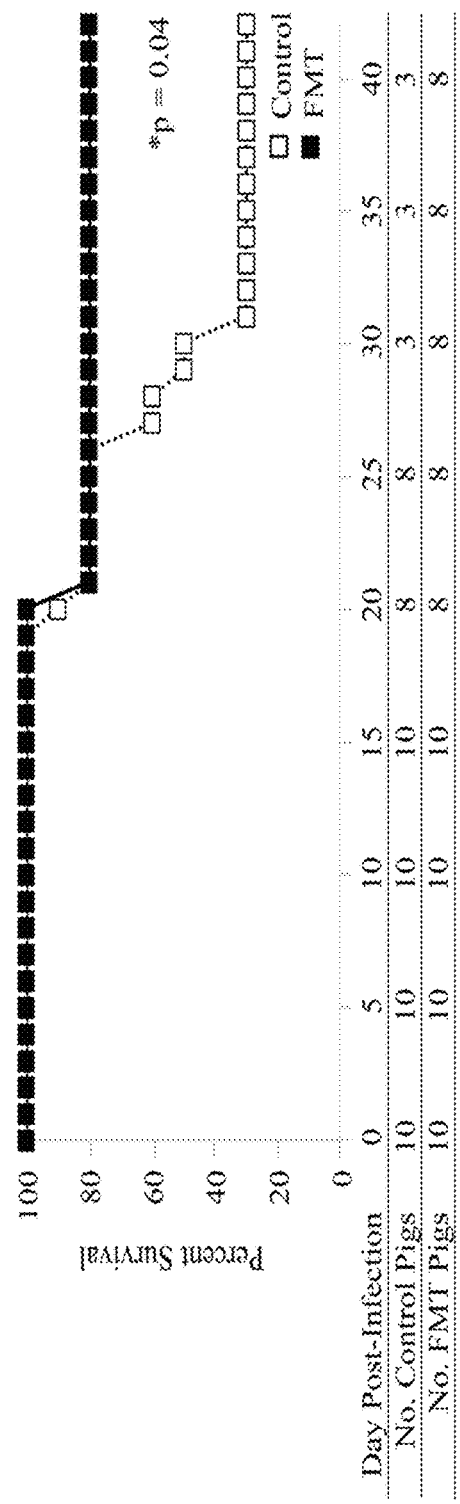

FMT reduced the number of PCVAD-affected pigs: Morbidity and mortality of the FMT and control groups are shown in FIG. 1. Morbidity rates of the control and FMT groups were comparable in the first 22 days after co-infection (FIG. 1A). In this figure, the percent morbidity over time data is shown as the percent of pigs in each group with veterinary treatment prescribed due to moderate to severe clinical disease. Asterisks demarcate statistically significant differences (*p<0.05 and <0.1; Fisher's exact test). During this time, 4 control pigs and 3 FMT pigs showed clinical signs, including dyspnea, open-mouth breathing, coughing, tachypnea, mucoid rhinorrhea, conjunctivitis, reduced body condition, lethargy/weakness and pyrexia. Starting on 23 dpi, the morbidity rates of the control and FMT groups diverged, with 5 control pigs (⅝; 62.5%) and only 1 FMT pig (⅛; 12.5%) exhibiting clinical signs sufficient to require veterinary intervention, including depression, dyspnea, tachypnea, coughing, open-mouth breathing, rough hair coat, mucoid oculonasal discharge, pyrexia, emesis and diarrhea, muscle wasting and loss of condition, ataxia, hypoxia and cyanosis. On days 25 and 26 after co-infection, morbidity rates were significantly different (p=0.04; Fisher's exact test), with 75% and 12.5% of control and FMT pigs receiving treatment, respectively. A trend towards significantly higher morbidity was also seen on 27 dpi (p=0.09; Fisher's exact test) and 28 dpi (p=0.05; Fisher's exact test). By 28 dpi, clinical disease had completely resolved in the remaining 8 FMT pigs while 50% of control pigs (3/6) remained on treatment. Clinical disease in affected FMT and control pigs (n=9) was consistent with PCVAD. Unaffected pigs (n=11) had mild to a complete lack of clinical signs. With regards to resulting mortality, initial death rates were similar between the two groups, with 20% mortality at 21 dpi. However, by the end of the study, the mortality in the control group was 70% compared to 20% for the FMT pigs (see FIG. 1B). Mortality between 19 and 30 dpi was due to pigs that died or were euthanized due to severity of clinical disease. Overall, the mortality rate of the control group (7/10, 70%) was significantly higher than that of the FMT group (2/10, 20%; p=0.0447, Mantel-Cox test). When taken together, pigs which received the FMT treatment showed a reduction in PCVAD.

Figure 1C:
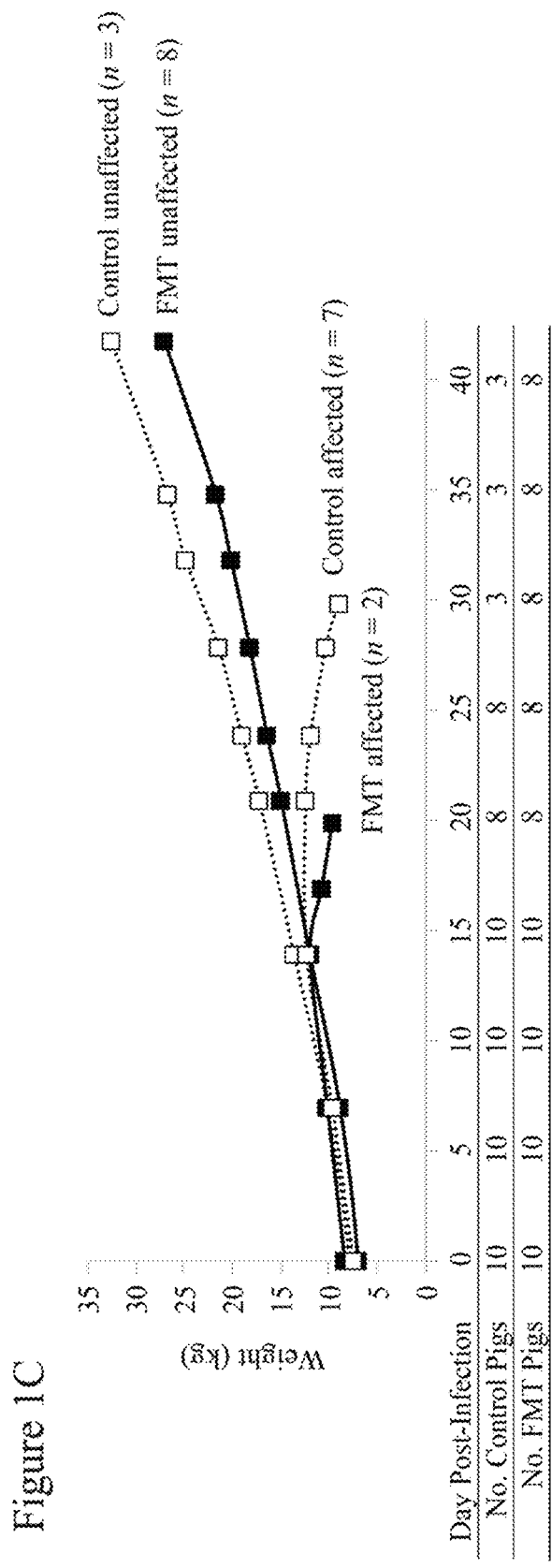

The clinically affected pigs showed a decrease in weight gain beginning at approximately 17 dpi (FIG. 1C). Overall, no significant differences were detected between the two groups in regards to absolute weights during the biweekly or weekly weight measurements throughout the study (p>0.05, repeated measures analysis with multiple t-tests). The one exception was the final weights on 42 dpi, where the 3 remaining control pigs had a mean weight significantly higher than that of the 8 remaining FMT pigs (p=0.04, repeated measures analysis). However, this comparison was significantly impacted by the high mortality rate in the control pigs; as such, the increase in weight in the remaining control pigs was likely the result of decreased competition for feed. Evaluating the weight gain of individual pigs (FIG. 2), it is clear that the weight gain of the control pigs was impacted to a greater extent than the FMT pigs throughout the trial. During peak clinical disease between 17 and 30 dpi, 7 control pigs lost body weight whereas only 2 FMT pigs lost body weight (p=0.07, Fisher's exact test). Control pigs were 9.3 times more likely to lose weight during this period (95% CI: 1 to 56.5). Overall, FMT improved the uniformity of weight gain in the post-infection period and reduced the number of pigs which lost weight associated with PCVAD.

Complete necropsies were performed on each pig by a board-certified pathologist within 24 hours post-death or euthanasia. Representative gross and microscopic lesions seen in pigs with PCVAD are shown in FIG. 3. Images of minimally-affected pigs are included for comparison. Examples of gross lesions included interstitial pneumonia with consolidation and hemorrhage, splenic infarcts, mucohemorrhagic rhinitis, lymphadenopathy with congestion and edema, pericardial effusion, mucohemorrhagic exudate in trachea, serous atrophy of fat, enteritis and intestinal ulceration, infarction of extremities, and tonsillar congestion. On gross examination of lung tissue, pneumonia was overall more severe in the control group, with 70% of the control pigs having severe interstitial pneumonia with marked edema, coupled with enlarged lymph nodes, characteristic of PCVAD. In addition, a few of the affected pigs in the control group had bronchopneumonia and fibrinous pleuritis. Interestingly, these pigs also had severe suppurative rhinitis (FIG. 3H). Rhinitis, bronchopneumonia and pleuritis are suggestive of a secondary bacterial infection, likely due to immunosuppression associated with both PRRSV and PCV2 infections. In contrast, only 30% of the FMT group had severe interstitial pneumonia and enlargement of the lymph nodes on gross examination, characteristic of PCVAD.

Figure 3G:
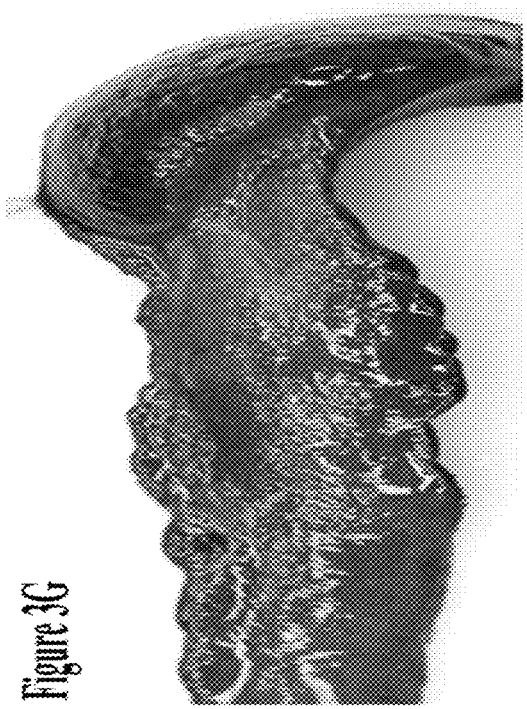
FIG. 3G is a photograph of a spleen showing large infarct along border.
Figure 3I:
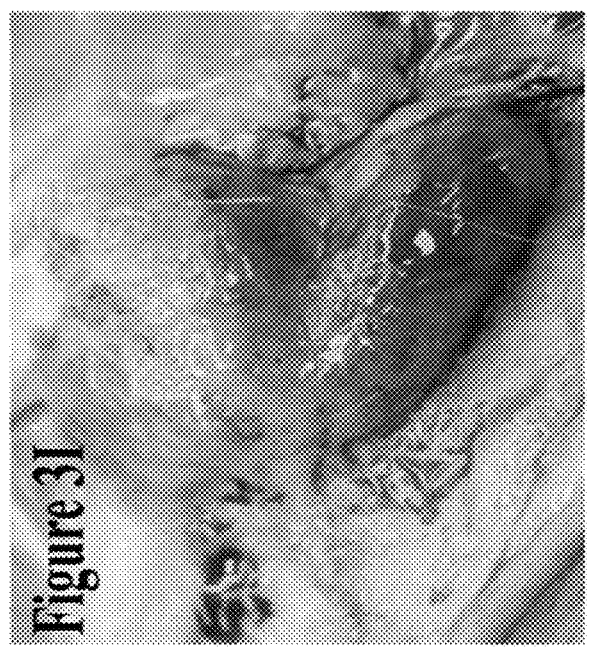
FIG. 3I is a photograph showing severe hemorrhagic lymphadenopathy of inguinal lymph nodes.
Figure 3F:
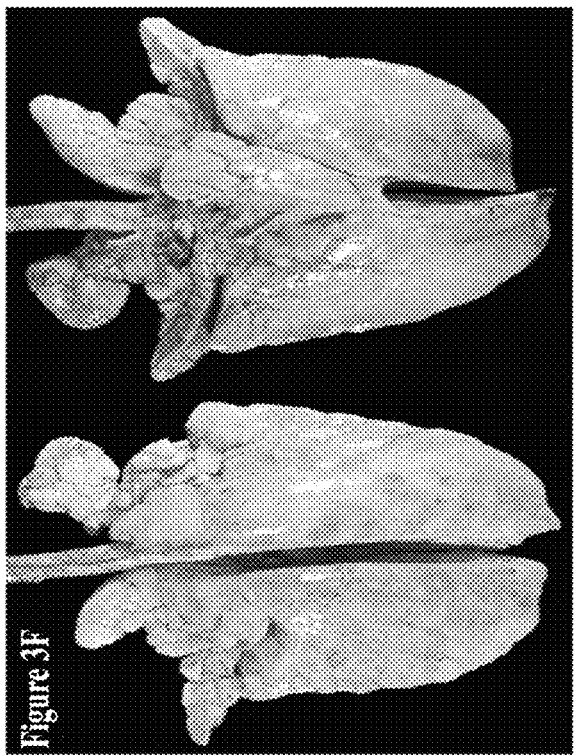
FIG. 3F is a photograph of a dorsal and ventral gross lung showing minimal consolidation, hemorrhage, and pneumonia affecting approximately 12% of lung.
Figure 3H:
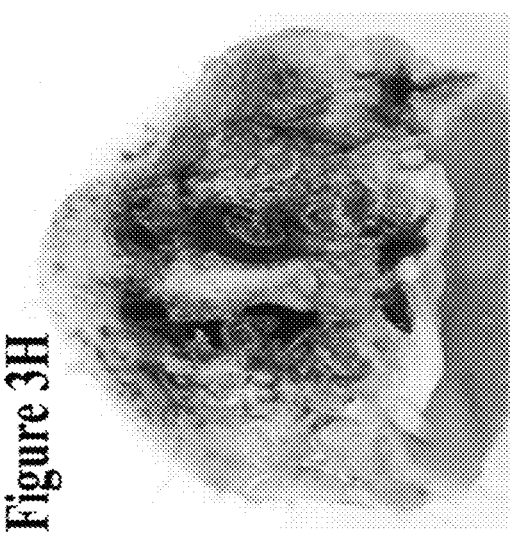
FIG. 3H is a photograph of nasal turbinates showing severe mucohemorrhagic rhinitis.

Gross lung tissue images were captured during necropsy and subsequently scored for severity of lesions (FIGS. 3E, 3F and 4A). Control pigs had a range of 30.5 to 99.0% of lung affected, with a mean of 82.4±20.3%. FMT pigs had a range of 10.0 to 99.0% of lung affected, with a mean of 53.6±40.6%. These differences had a trend towards significance (p=0.06, unpaired t-test). A lung weight to body weight ratio was calculated for each pig and are depicted in FIG. 4B. Control pigs had significantly higher ratios when compared to FMT pigs (p=0.04, unpaired t-test), indicative of increased cellular infiltrate and edema characteristic of interstitial pneumonia.

Lesions were also assessed through histopathology. Microscopic lesions in the lungs included lymphoplasmacytic and histiocytic interstitial pneumonia, suppurative bronchopneumonia, and interlobular septal edema and hemorrhage. Lymphoid depletion with histiocytic replacement was seen in the tracheobronchial lymph nodes. Lymphoid depletion was scored in all 20 pigs, with 7/10 control and 3/10 FMT pigs having severe lymphoid depletion (FIGS. 3A and 4C). Although lymphoid depletion scores were generally higher in control pigs, this difference was not statistically significant (p=0.155, Mann-Whitney U test). Severe lymphoid depletion was associated with large amounts of PCV2 antigen (FIG. 3A). Degree of interstitial pneumonia was also scored in all 20 pigs, with 6/10 control and 2/10 FMT pigs having severe diffuse interstitial pneumonia with >75% lung lobe involvement (FIGS. 3C and 4D). Control pigs again tended to have higher overall severity of microscopic lung lesions; however, this difference was not statistically significant (p=0.164, Mann-Whitney U test).

Taken together, control pigs had increased severity of gross and microscopic lesions associated with PCVAD when compared to pigs that received the transplant material, indicating that FMT provided partial protection from both respiratory and lymphoid disease. This difference was seen due to an increased number of PCVAD-affected pigs in the control group.

FMT reduced PRRSV and PCV2 virus replication and increased antibody production: PRRSV and PCV2 viremia curves are shown for both individual pigs as well as group means (FIG. 5). PRRSV viremia followed the typical time course, peaking at 7 dpi prior to a gradual decline over the next 5 weeks. Interestingly, most of the PCVAD-affected pigs had PRRS viremia rebound, a phenomenon initially described in 2010 and later by our group. For example, one control pig had peak PRRSV replication at 7 dpi (5.8 log 10 copy number per PCR reaction), a gradual decline of PRRSV replication until a low at 21 dpi (2.9 log 10 copy number per PCR reaction), and a second peak of PRRSV replication at 30 dpi (5.9 log 10 copy number per PCR reaction). When comparing mean PRRSV replication between groups, the only significant difference was seen at 28 dpi where the control group had significantly higher viremia; a mean of 3.9 and 3.0 log 10 copy number per PCR reaction was seen for control and FMT groups, respectively (p=0.02, repeated measures analysis).

PCV2 viremia also followed the typical time course, peaking later in the co-infection period between 14 and 21 dpi, followed by a plateau through the conclusion of the study. Interestingly, all nine pigs that died had significantly higher levels of PCV2 replication when compared to pigs that survived the course of the study (FIGS. 5D, 5E and 5H). Specifically, surviving pigs maintained <7 log 10 copies/PCR reaction in the serum at all measurements whereas pigs that died had >7 log 10 copies/PCR reaction detected during the study. When comparing the two groups' mean PCV2 replication, significant differences were seen on 7 and 21 dpi, where the FMT group had a more rapid increase in PCV2 replication on 7 dpi and a more rapid decline in PCV2 replication on 21 dpi (p=0.02 and 0.03, respectively; repeated measures analysis). Overall, PCVAD-affected pigs had high levels of PCV2 and PRRSV in serum at the time of death or euthanasia, confirming the role of viral load in the course of clinical disease (FIGS. 5G and 5H). In general, virus replication during peak clinical disease was reduced in the FMT group, demonstrating a protective effect of FMT on viral load.

Antibodies were measured against PRRSV N protein, PCV2 whole capsid protein (CP 43-233), and PCV2 decoy epitope (CP 160-233) (sequence positions taken from Genbank accession #HQ713495). PRRSV antibodies were detected similarly in both groups initially on 7 dpi and peaking between 11 and 14 dpi (FIG. 6A). PRRSV antibodies were detected at a greater level in FMT pigs on 21, 28 and 42 dpi (p=0.06, p=0.02, and p=0.05, respectively; repeated measures analysis). When comparing PCV2 antibody levels, a similar trend was noted with FMT pigs having higher antibody levels. FMT pigs had higher CP 43-233 antibodies at 21 and 28 dpi whereas the FMT pigs maintained higher CP 160-233 antibodies from 21 dpi until the conclusion of the study. Taken together, FMT promoted the production of higher and more sustained levels of antibodies directed at both PRRSV and PCV2.

FMT shifted microbiome composition: Fecal microbiomes of the transplanted and control groups were analyzed both before and after FMT or mock-transplantation by a pan-microbial array (LLMDA) and 16S rDNA sequencing. First, microbiome composition and diversity was measured by the LLMDA. Diversity was calculated as the mean number of species and families in each group; after transplantation, the mean number of species was 62.3±2.7 and 59.9±4.2 for the control and FMT groups, respectively. With regards to family diversity, the mean number of families on 0 dpi in the control group was 35.3±2.7 while the transplant group had 33.8±2.6. Interestingly, no significant differences in species or family diversity were detected in the FMT group compared to the controls after transplantation using the pan-microbial array. Microbiome diversity was also similar in the two groups upon arrival (data not shown).

Microbiome composition was also assessed by the LLMDA through the presence of individual phyla, families and species in the two groups. After 7 days of transplantation, there were 64 total families and 166 total species detected in both the control and transplanted groups. Several differences were detected between the transplant and control groups after transplantation that were not detected upon arrival (FIG. 7A). Specifically, the family Synergistaceae was detected at a decreased prevalence rate in the transplanted group after FMT compared to the controls (20 and 70%, respectively; p=0.07; Fisher's exact test) and a bacterium in the Intrasporangiaceae family was detected in a higher proportion of the transplant pigs when compared to the control pigs (100 and 50%, respectively; p=0.03; Fisher's exact test). Even though members of the Intrasporangiaceae family have been discovered in environmental samples and sequenced, there is a lack of research exploring the effects of these organisms on the vertebrate gut microbiome.

Finally, species diversity within each family was assessed for differences associated with transplantation (FIG. 7B). Most families had similar species diversity between the control and transplanted groups. However, within the families Spirochaetaceae and Vibrionaceae, there was greater species diversity in the control group compared to the transplanted group. The mean number of species within the family Spirochaetaceae was 2.6 species in the control group, while in the transplant group it was 2.0 species (p=0.01; Mann Whitney U test). The mean number of species within the family Vibrionaceae was 1.6 species in controls, while in the transplant group it was 0.8 species (p=0.02; Mann Whitney U test). Overall, the LLMDA failed to detect a global increase in microbiome diversity after 7 days of transplantation; however, several shifts in microbiome composition were detected, primarily based on a reduction in bacteria generally considered pathogenic.

A secondary analysis was performed to assess microbiome diversity between PCVAD-affected and unaffected pigs using the LLMDA. Affected and unaffected pigs had similar mean numbers of families and species when compared on days −7 and 0 post-infection. However, there was a significant increase detected in the number of families in the unaffected pigs between −7 and 0 dpi, with the mean number of families detected increasing from 28.9 to 33.7 during the transplantation period (p=0.03; Mann-Whitney U test). Although an increase in family diversity was also seen in the affected pigs between −7 and 0 dpi, this difference was not statistically significant (p=0.20; Mann-Whitney U test). Species diversity also increased in both affected and unaffected pigs during the transplantation period, albeit at a similar rate (p=0.07 and p=0.09 for unaffected and affected pigs, respectively; Mann-Whitney U test). Taking the results together from the LLMDA, there is some evidence suggesting that pigs unaffected by PCVAD after challenge had a greater increase in microbiome diversity during the transplantation period.

Fecal bacterial communities of the control and transplanted groups were also analyzed using 16S rDNA sequencing both prior to and immediately following transplantation (FIGS. 8 and 9). A total of 2,446,796 quality-filtered 16S rDNA sequences of the V4 region were generated with an average read depth of 61,169 reads per sample. To determine if sampling depth was adequate for gut microbiota analysis, Good's coverages were calculated, which displayed that 99.4-99.8% of the bacterial community in the gut was represented in the dataset.

The chao I alpha diversity metric for richness was similar in the transplant and control animals at 7 days post transplantation (p≥0.82; FIG. 8A). The phylum level distribution of the major taxa in both control and transplanted pigs included Bacteroidetes, Firmicutes, and Proteobacteria. Interestingly, the phylum Actinobacteria was almost half in the transplanted group compared to the control group (1.7% vs 3.3%, respectively; FIG. 8B). The family level analysis of the transplanted and control animals revealed Prevotellaceae, Paraprevotellaceae, Bacteroidales S24-7, Lactobacillaceae, Christensenellaceae, Lachnospiraceae, Ruminococcaceae, and Veillonellaceae to be the predominant families (FIG. 8C). Phyla composition was not significantly different across the transplant and control animals. Substantial inter-animal variation in the rumen microbiome composition has been reported. Bacterial communities did not cluster by treatment group, suggesting no global shifts in the bacterial populations as a result of the fecal microbiota transplantation. However, there was a significant day effect displayed during transplantation (p<0.001). PERMANOVA analysis supported this observation of no overall bacterial community composition differences across the two treatment groups (p=0.77).

To reduce animal-animal variation, a core measurable microbiome (CMM) was defined for the control and transplanted groups. For the transplant group, the CMM was composed of 306 OTUs (23.5% of total OTUs), which represented 81.1% of the rarefied quality-filtered reads. For the control group, the CMM was composed of 316 OTUs (25.3% of total OTUs), which represented 83.2% of the rarefied quality-filtered reads.

To further investigate potential bacterial community differences across the transplanted and control groups, differentially abundant OTUs across the CMM were identified using the LefSe algorithm. A total of 30 significant, differentially abundant OTUs with LDA scores ≥2 were identified across comparisons of the two groups (FIG. 9). The differential OTUs associated with the transplant group belong to the bacterial families Veillonellaceae, Lachnospiraceae, and Ruminococcaceae. The members of the Lachnospiraceae family are fermentative, anaerobic, and chemoorganotrophic and have the ability to hydrolyze different substrates including xylanase, α- and β-glucosidase, pectin methylesterase, acetyl-β-glucosaminidase, α-L-arabinofuranosidase, α- and β-galactosidase, pectate lyase, β-xylosidase, or α-amylase. The organisms of Ruminococcaceae family are common gut microbes of animals and humans, which help the host to break down complex carbohydrates. Overall, FMT increased the relative abundance of several bacterial families beneficial for nutrient digestion and metabolism; these shifts may have resulted in an increased ability to harvest energy from the diet.

Additionally, the 16S rDNA bacterial community composition was analyzed based on the prevalence of disease in the PCVAD-affected (n=9) and unaffected (n=11) pigs. A two-way ANOVA was performed on the Chao1 and observed OTUs to determine the effect of subsequent disease phenotype on pre-challenge bacterial diversity. Both measures of bacterial diversity were lower in the affected group on 0 dpi (FIG. 10), suggesting that reduced microbial diversity was associated with subsequent development of disease; however, these differences were not statistically significant (p≥0.14 and p≥0.24, respectively). We also performed beta-diversity analysis to determine the effect of the disease phenotype on global microbial community diversity using PERMANOVA analysis. This analysis demonstrated no differences in community composition based on disease phenotype (p≥0.46), but detected a significant effect of day (p<0.001) on the bacterial community composition.

Discussion

Although FMT has been accepted for centuries as a treatment for various gastrointestinal diseases, it has only been very recently that FMT has been recognized as an alternative therapeutic for diseases outside of the gastrointestinal tract, such as respiratory or neurologic diseases. Moreover, using FMT as a prophylactic tool prior to the development of disease has been even less explored. The current study describes FMT efficacy when used as a prophylactic tool to prevent PCVAD in pigs infected with two important swine pathogens. Additionally, the study was conducted in a manner in line with current swine industry standards, where pigs are typically handled at 3 weeks of age after weaning and without broad-spectrum antibiotic therapy.

To identify beneficial characteristics of the FMT material, 2 diagnostic tests were used for characterization: 1) a pan-microbial array and 2) bacterial culture. Comparing these results in Tables 1 and 2 reveals several discrepancies between the two different detection methods. Interestingly, several bacteria cultured through standard methods, such as Escherichia coli and Streptococcus sp., are not detected on the pan-microbial array. Culture methods may promote growth of certain well-characterized bacterial species, even if the genome is present at a rate lower than that detectable by the microarray. On the other hand, the microarray detected tens of organisms not detected by bacterial culture, such as protozoan and fungal species, which may be playing important roles. Previous studies have reported similar results. For example, Sung et al. (2018) reported bacterial species detected in bronchoalveolar lavage fluid by both conventional culture techniques as well as next generation sequencing (NGS). Similar to the current study, they detected some species only by culture and other species only by sequencing, with increased diversity detected in the genome-based technique. Interestingly, the genera Staphylococcus and Escherichia were only detected by culture and not by NGS (Sung et al., 2018), a result similar to our findings on the transplant material (Tables 1 and 2). With advantages and limitations to each diagnostic test, using culture and DNA-based techniques in combination can serve to provide a more comprehensive characterization of complex microbial communities.

Biphasic clinical disease after co-infection with PRRSV and PCV2 has been described previously. Clinical disease associated with PRRS is typically seen in the first 21 dpi, during peak PRRSV replication. In contrast, clinical disease associated with PCVAD is typically seen after 21 dpi and is associated with the peak and plateau in PCV2 replication. Although respiratory signs are common in both phases, clinical disease associated with PCVAD is typically more severe and associated with significant weight loss and muscle wasting. Compared to previous studies where PCV2b was used, the current study used PCV2d, which has been recently reported as the most common circulating PCV2 genotype in U.S. swine. This use of PCV2d appeared to increase morbidity and mortality rates of co-infected pigs. The principal effect of FMT in the co-infection model was to decrease the number of PCVAD-affected pigs, as demonstrated by a significant reduction in morbidity and mortality. For example, FIG. 1B shows an approximate 70% reduction in mortality of transplanted pigs. Additionally, parenteral antimicrobial treatments prescribed for clinical disease were reduced by 60% in the FMT group (FIG. 1A). With increasing pressure to eliminate antimicrobial usage in food animal production, a 60% decrease in prescribed antimicrobials is a significant effect, important to both human and animal health. Although FMT did not appear to significantly impact clinical disease in the first half of the co-infection period, typically associated with PRRS, there was a significant impact of FMT on both PRRSV replication and PRRSV antibody production. Further research is warranted to understand if FMT improves response to PRRS in a PRRSV-only infection model.

The mechanisms by which FMT is effective are poorly understood but thought to be associated with increasing microbial diversity and restoring normal microbial communities which provide both local and systemic benefits to the host. How FMT protected nursery pigs from developing PCVAD in this study is unknown, but may be due to several possible mechanisms. First, FMT may have improved nutrient digestion and feed efficiency during peak clinical disease, increasing the uniformity of weight gain and improving growth of transplanted pigs. Specifically, FMT increased the relative abundance of several bacterial families associated with metabolism, including Veillonellaceae, Lachnospiraceae, and Ruminococcaceae, which may have played a beneficial role in the second half of the co-infection period in regards to nutrient absorption. Two of these families, Lachnospiraceae and Ruminococcaceae, have previously been associated with fatness traits in pigs and our previous work detected a positive association between Ruminococcaceae species and growth after co-infection. In humans, increased weight gain and obesity has been reported in association with FMT therapy from overweight donors. Additionally, certain microbiome bacteria have been associated with preventing cachexia in mice after respiratory infection through an insulin-like growth factor 1 signaling pathway in skeletal muscle. Through these potential direct or indirect mechanisms, FMT may play a role in maintaining weight gain of co-infected growing pigs.

As a second possible mechanism, FMT may modulate the systemic immune response, increasing the function of immune cells or stimulating cytokine production. For example, microbiome modulation in weaned pigs has been shown to increase the nonspecific expression of antiviral cytokines, such as IFN-$\gamma$ and TNF-$\alpha$. In a mouse model, individuals with healthy and diverse gut microbiomes had enhanced alveolar macrophage phagocytosis and increased pulmonary TNF-$\alpha$ after *Streptococcus pneumoniae* infection when compared to individuals with depleted gut microbiomes. In the current study, evidence for an enhanced immune response to both PRRSV and PCV2 was demonstrated by a reduction in pulmonary pathology as well as a more robust and prolonged antibody response to both viruses detected in the serum of transplanted pigs. As a third possible mechanism, FMT may provide antigens similar to PRRSV or PCV2 immunogenic proteins, allowing an early or anamnestic antibody response during co-infection. Finally, FMT may enhance gastrointestinal health and the physical barrier of normal flora in the intestine, reducing the likelihood of bacterial translocation and septicemia during immunosuppressive viral infections, such as PRRSV and PCV2. Supporting this possible mechanism in the current study was the documented reduction of two bacterial families thought to be primary pathogens, including Spirocheataceae and Vibrionaceae, in transplanted pigs. This suggests that FMT may reduce the prevalence of enteric pathogens by increasing the relative abundance of beneficial microbes.

Consistent with our previous studies, there was evidence in the current study suggesting an association between increased microbiome diversity and improved clinical outcome. However, there was perhaps a surprising lack of significant global increases of microbiome diversity in pigs receiving the transplant. This lack of detectable changes in the microbiome diversity of transplanted pigs may be due to two possibilities. First, it is possible that FMT increased microbiome diversity in the proximal intestine, such as the duodenum or jejunum, and was not reflected in the analysis of the fecal samples. Perhaps an assessment of the intestinal microbiome would have revealed a significant increase in diversity of transplanted pigs. Second, it is possible that FMT did not result in colonization of a significant number of microbes and instead, provided benefits to the transplanted pigs primarily through immunostimulation and antigenic exposure. In humans, where FMT is most commonly used to treat recurrent *Clostridium difficile* infections, patients have almost always been treated with several standard doses of antibiotics, making an increase in microbiome diversity more likely with FMT therapy. Even in these human patients, however, Staley et al. (2016) reported that successful resolution of *C. difficile* infections through FMT treatment did not require complete microbiota engraftment. Similarly to the current study, it does not appear that complete microbiota engraftment occurred in transplanted pigs; nonetheless, significant beneficial effects occurred due to transplantation.

Compared to humans receiving FMT, an important concept to discuss for the current study is that pigs were not treated with antimicrobials and thus had normal microbiomes for their age at the time of transplantation. Pigs were weaned when 3 weeks old and allowed normal contact with sows and a commercial environment after birth. The rationale behind this experimental design was to model commercial conditions and to evaluate FMT as a preventative tool that may be applied to swine production in the field. However, this could be considered a limitation of the study, due to our inability to control the microbiota present at the time of transplantation, such as would be the case had microbiota-depleted or germ-free pigs been utilized.

In previous publications by our group evaluating the pathogenesis of PCVAD, antibodies directed at the PCV2b capsid protein 160-233 were associated with the development of clinical disease or PCVAD. Trible et al. (2012) reported these residues as containing a non-protective decoy epitope, with PCVAD pigs having more antibodies directed at this portion of the capsid protein. Perhaps a surprising finding was that the FMT pigs in the current study had higher levels of antibodies directed at the decoy epitope and overall less clinical disease. However, this may be explained by the use of PCV2d in the current study.

Decades of research into control of respiratory disease associated with PRRS have failed to produce a broadly protective vaccine or programs capable of long-term virus elimination from farms. Due to the significant economic and animal welfare impacts that respiratory disease continues to have on the swine industry, it is necessary to consider alternative strategies, such as FMT, for the control of respiratory disease in swine production. Very recently, microbiome therapeutics have been developed for the prevention and/or treatment of diseases in the respiratory tract of children. For example, in May 2017, a microbiome therapeutic utilizing a mixture of 4 gut bacteria, including *Faecalibacterium, Lachnospira, Veillonella,* and *Rothia* (FLVR), was announced for preventing childhood asthma and potentially other childhood allergic diseases. Interestingly, two of those bacterial families were differentially expressed in FMT pigs post-transplantation. Utilizing beneficial gut microbes for the prevention and treatment of respiratory disease is an emerging and exciting area of study. As respiratory infections are a major cause of morbidity and mortality in swine and other livestock, FMT or other microbiome therapeutics provide a promising approach for control of these complex, often polymicrobial, and economically devastating diseases.

Example 2

Materials and Methods

Animals and housing: The study was conducted as part of a project to evaluate the role of host genetics in determining the outcome following co-infection with PRRSV and PCV2.

Four week-old barrows (n=95; average age 26.8±2.0 days) were obtained from a single commercial source herd negative for PRRSV. The sow herd had no history of clinical disease associated with PCV2 or PRRSV. Relevant health history included a recent introduction of porcine epidemic diarrhea virus (PEDV) prior to farrowing. All piglets were confirmed to be negative for PRRS viremia using qPCR prior to challenge. While pigs were derived from a sow herd previously vaccinated with a PCV2 capsid subunit vaccine, the piglets were not vaccinated for PCV2 and were utilized in the study without regards to the presence of maternal antibody. All pigs were housed in one environmentally controlled room at the Kansas State University Large Animal Research Center, and maintained under BSL-2 conditions. The room was chemically disinfected, cleaned with a high heat pressure washer and gas decontaminated with vaporized hydrogen peroxide prior to use. The room was empty for approximately 9 weeks prior to the start of the study. Pigs were housed in 10 pens, each 144 sq ft with 9-10 pigs per pen. Pigs were given access to food and water ad libitum.

Challenge inoculum: The PRRSV and PCV2b isolates used to prepare the inoculum were originally derived from the lymph node of a pig with severe PMWS, as described previously (Trible et al., 2012). PRRSV (isolate KS62, GenBank Accession #KM035803) was isolated by propagation on MARC-145 cells. Since wild-type PCV2b (Genbank Accession #JQ692110) does not propagate to high levels in cell culture, we took advantage of the heat stability of PCV2 to make a virus preparation from a lymph node suspension enriched for PCV2. The suspension was heat-treated at 55° C. for 30 minutes to remove PRRSV, bacteria and other heat-labile agents. The treated homogenate was recombined with the isolated PRRSV to infect cesarean-derived, colostrum-deprived (CD/CD) pigs. A combination lung/lymph node homogenate was prepared from the CD/CD pigs and PRRSV and PCV2 were isolated from the homogenate by the methods described above. Analysis of the heat-treated preparation for common agents showed that the preparation was negative for most heat stable agents, such as parvovirus, but still positive for torque teno sus viruses (TTSuV) and porcine endogenous retroviruses (PERVs) on DNA microarray. Both TTSuV and PERV are ubiquitous to swine.

PRRSV was titered on MARC-145 cells. Briefly, virus was serially diluted 1:10 in MEM (Corning) supplemented with 7% FBS (Sigma-Aldrich), penicillin-streptomycin (Pen Strep; 80 Units/ml and 80 µg/ml, respectively; Gibco), 3 µg/ml Fungizone (Gibco), and 25 mM HEPES (Life Technologies). The dilutions were then added in quadruplicate to confluent MARC-145 cells in a 96 well tissue culture plate (BD Falcon). Following a 4 day incubation at 37° C. in 5% CO2, wells were examined for PRRSV induced cytopathic effects, and the 50% tissue culture infectious dose ($TCID_{50}$/ml) was calculated using the method of Reed and Muench.

The quantity of PCV2 was determined by titration on swine testicle (ST) cells. Briefly, serial 10-fold dilutions of the PCV2 challenge stock were plated in quadruplicate to rapidly dividing ST cells in a 96 well tissue culture plate (BD Falcon). Dilutions were prepared in EMEM (Sigma-Aldrich) supplemented with 7% FBS (Sigma-Aldrich) and 50 µg/ml of gentamycin (Lonza). Following a three day incubation at 37° C. in 5% CO2, cells were fixed and permeabilized with 80% acetone and then stained with fluorescein isothiocyanate (FITC)-labeled porcine anti-PCV (Veterinary Medical Research and Development, Inc.). Infected cells were visualized using an inverted fluorescent microscope and the $TCID_{50}$/ml was calculated using the method of Reed and Muench.

Animal model and experimental design: A total of 95 pigs were randomly allocated into 10 identical pens using a random number assignment protocol and housed in groups of 9-10 pigs per pen. After acclimating for two weeks, all pigs were challenged with a combination of PRRSV and PCV2b. The challenge viruses were recombined to yield a 2 mL dose consisting of $10^{3.6}$ $TCID_{50}$ PCV2 and $10^5$ $TCID_{50}$ PRRSV in MEM. The 2 mL dose was split with 1 mL administered intranasally and the remaining 1 mL administered intramuscularly. Individual body weights were collected on −14, −7, 0, 7, 14, 21, 28, 35, 42, 49, 56, 63, and 70 days post-infection (dpi). Blood samples were collected from all pigs on 0, 4, 7, 11, 14, 21, 28, 35, 42, 56 and 70 dpi. At 63 dpi, 20 pigs were selected from the surviving 78 pigs and categorized as having the best or worst clinical outcomes. The 10 best clinical outcome pigs were selected due to having the highest average daily gain (ADG) from 0-63 dpi and due to a complete lack of overt clinical disease during the post-challenge period. The 10 worst clinical outcome pigs were selected due to having the lowest ADG from 0-63 dpi and due to having at least 10 days of moderate to severe clinical disease during the post-challenge period. All 20 pigs were humanely euthanized on 70 dpi and complete necropsies were performed.

Clinical Disease and pathology: Pigs were evaluated daily for the presence of clinical signs, including dyspnea, aural cyanosis, coughing, nasal discharge, open mouth breathing, poor body condition, muscle wasting, pallor or jaundice, lameness, joint effusion, depression and lethargy. Each pig was visually examined by a veterinarian or veterinary assistant each day during the study period. The majority of clinical signs were documented as either present or absent during daily evaluations. Five of the clinical signs, including dyspnea, lethargy, decreased body condition, diarrhea, and lameness, were scored based on severity. Appropriate treatments were initiated for pigs that presented with moderate to severe clinical disease. Examples of clinical presentations (or clinical signs) where treatment was administered included: 1) difficult respiration, 2) mucoid nasal discharge, 3) lameness with associated joint effusion, 4) pallor or jaundice associated with muscle wasting, and 5) lethargy or depression with a rectal temperature ≥104° F. For clinically affected pigs, antibiotic therapy was administered, including ceftiofur hydrochloride for respiratory or systemic disease and oxytetracycline for infectious arthritis. All pigs with overt clinical disease and rectal temperatures ≥104° F. were administered flunixin meglumine, a nonsteroidal anti-inflammatory drug (NSAID). Pigs with intractable fevers of greater than 4 days duration were given a 2 day wash-out period and then administered oral meloxicam. Clinical signs and systemic treatments unrelated to PRRSV/PCV2 co-infection (e.g. lacerations, dermatitis, hoof wounds, congenital hernias) were documented but were not considered as clinical disease in selecting the best and worst outcome groups. Animals were humanely euthanized with pentobarbital sodium. Complete necropsies and histopathology were performed by a board certified pathologist who was blinded as to the source of the pigs. Tissues were collected from each pig including lung (1 section from each lobe) and tracheobronchial lymph node. Tissues were allowed to fix in 10% neutral buffered formalin for at least 7 days, routinely processed in an automated tissue processor, embedded in paraffin, and stained with hematoxylin and eosin (H&E stain). Microscopic lung lesions were estimated using a 0 to 4 scoring system as previously described. Degree of lymphoid depletion was estimated using the following scoring system: 0, no lymphoid depletion; 1, mild or small amount of lymphoid depletion; 2, moderate or intermediate extent of lymphoid depletion; 3, severe or large extent of lymphoid depletion. Pigs that died or were humanely euthanized due to pathology unrelated to PCV2/PRRSV co-infection (e.g. gastric torsion, non-infectious lameness, etc.) were excluded from the study. Average daily gain (ADG) was calculated as the change in weight divided by the number of days and was reported in kg.

Measurement of PRRSV and PCV2 viremia: Viral DNA and RNA were extracted simultaneously from 50 µL of serum using Ambion's MagMAX 96 Viral Isolation Kit (Applied Biosystems) in accordance to the manufacturer's instructions. PRRS viral RNA was quantified using EZ-PRRSV MPX 4.0 Real Time RT-PCR Target-Specific Reagents (Tetracore) according to the manufacturer's instructions. For consistency, each plate contained Tetracore Quantification Standards and Control Sets for use with EZ-PRRSV MPX 4.0 RT-PCR Reagents. All PCR reactions were carried out on a CFX96 Touch Real-Time PCR Detection System (Bio-Rad) in a 96-well format using the recommended cycling parameters. PCV2 DNA was quantified using SsoAdvanced Universal SYBR Green Supermix (Bio-Rad). Forward and reverse PCR primers were 5'-AATGCAGAGGCGTGATTGGA-3' (SEQ ID NO. 1) and 5'-CCAGTATGTGGTTTCCGGGT-3' (SEQ ID NO. 2), respectively. Primers were used at a final concentration of 300 µM. Nuclease free water was used to bring the mastermix volume to 18 µL per reaction. The addition of 2 µL of template nucleic acid brought the final reaction volume for each sample to 20 µL. Standard curves and positive and negative controls were included on each plate. Plasmid DNA was used for the PCV2 standard curve and positive control template. DNA inserted into the plasmid was obtained from a field strain of PCV2 (PCV2b 321/393). Plasmid DNA was isolated using the PureYield Plasmid Miniprep System (Promega) according to the manufacturer's instructions. The DNA for the standard curve was quantified using a NanoDrop 8000 Spectrophotometer. The standard curve was produced by diluting the purified plasmid DNA 1:1000 in nuclease free water followed by five serial 1:10 dilutions in nuclease free water. The final standard curve contained 6 points ranging from 107 to 102 logs of template DNA which produced threshold crossing values between 15 and 33 cycles. Standard curves were run in duplicate with nuclease free water as a negative control. The PCV2 PCR was carried out on a CFX96 Touch Real-Time PCR Detection System using the following settings: activation at 98° C. for 2 minutes, followed by 40 cycles of denaturing at 98° C. for 5 seconds and annealing/extension at 60° C. for 10 seconds. The melting curve was performed between 65-95° C. using 0.5° C. increments. The PCR assay results were reported as log 10 PRRSV RNA starting quantity (copy number) per 50 µL reaction volume or log 10 PCV2 DNA starting quantity per 20 µL reaction volume.

DNA microarray analysis: LLMDA developed at the Lawrence Livermore National Laboratory was designed to detect all sequenced microbes. The LLMDA is not commercially available at the time of this study, but available for research collaborations. The version 5 of the LLMDA in the 12plex 135K format was used to analyze the microbiome in pig samples. This version of the array targets all vertebrate infecting pathogens including 1856 viruses, 1398 bacteria, 125 archaea, 48 fungi, and 94 protozoa. The LLMDA oligonucleotide probes are around 60 nucleotides in length and were designed to detect all sequenced microbial families with a large number of probes per sequence (average of 30 probes) to improve sensitivity in the evaluation of microbial nucleic acids in a variety of samples. The high-density oligo LLMDA microarray and statistical analysis method have been extensively tested in numerous studies for viral and bacterial detection in pure or complex environmental and clinical samples.

Each 1 mL sample for extraction consisted of 250 µL sample and 750 µL of Trizol LS reagent (Life Technologies). The purpose of adding Trizol was to inactivate all viruses and bacteria in tissue, fecal and serum samples so they could be shipped to Lawrence Livermore National Laboratory for molecular analysis. Nucleic acid purification could also be performed using commercially available kits, but only the Trizol method was used in this study. Each sample was brought to room temperature, 200 µL of chloroform was added, and the tube was shaken vigorously for 15 seconds. Samples were incubated at room temperature for 15 min and then centrifuged at 12,000×g for 15 min at 4° C. The upper aqueous layer was removed by pipetting and placed in a new tube for RNA extraction. The lower phases were saved for DNA extraction. For RNA extraction, 10 µg of glycogen was added to the aqueous phase along with 500 µL of 100% isopropanol. Following 10 min incubation, samples were centrifuged for 10 minutes at 12,000×g and 4° C. The supernatant was removed and the RNA pellet was washed with 1 mL of 75% ethanol. The sample was vortexed and centrifuged at 7500×g for 5 minutes at 4° C. Following centrifugation, the supernatant was removed and the RNA was air dried for 10 min. RNA pellets were re-suspended in DEPC water and RNA concentration was determined by the Qubit fluorometer (Life Technologies).

For DNA isolation, 300 µL of 100% ethanol was added to the interphase/organic phase, the tube was inverted several times, and incubated for 3 min at room temperature. Samples were centrifuged at 2000×g for 5 min at 4° C. and the supernatant was discarded. The DNA pellet was washed with 1 mL sodium citrate/ethanol solution (0.1M sodium citrate in 10% ethanol, pH 8.5), incubated for 30 min at room temperature, centrifuged at 2000×g for 5 min at 4° C., and the supernatant was removed. The sodium citrate/ethanol wash procedure was repeated once more. Following the wash procedures, 2 mL of 75% ethanol was added to the pellet and incubated at room temperature for 20 min and centrifuged at 2000×g for 5 min at 4° C. The supernatant was removed and the samples were air dried for 10 min. DNA pellets were resuspended in 8 mM NaOH solution and the DNA concentration was determined by the Qubit fluorometer.

For each lung sample, 10 µL (approximately 7.0-12.0 µg) of extracted RNA was used as input to generate double stranded cDNA following the standard Roche NimbleGen protocols using the Invitrogen Double-Stranded cDNA Synthesis Kit. Next, the cDNA was treated with RNase A and precipitated. After cDNA generation, 500 ng each of cDNA and DNA was mixed and labeled as detailed below.

Since less extracted nucleic acid was obtained from the fecal and serum samples, a random amplification was performed on these samples as described previously. For each amplification reaction, 54, each of extracted DNA and RNA was input into the reaction. The amplified DNA was purified using the Qiaquick PCR purification columns (Qiagen) and the yield was determined by the Qubit fluorometer.

Approximately 400-500 ng of amplified cDNA and DNA were mixed together and labeled using a one-color labeling kit (One-Color Labeling kit, Roche NimbleGen) following the standard manufacturer's protocols. Following the labeling reaction, a hybridization reaction was prepared with 10 µg of each labeled DNA and Roche NimbleGen hybridization reagents following the standard manufacturer's protocols. The MDAv5 12×135K microarray (Roche NimbleGen) was utilized for this work and samples were loaded onto the array and allowed to hybridize for 65 hr at 42° C. in a Roche NimbleGen Hybridization System set to mix mode B. After hybridization, the microarrays were washed following standard manufacturer protocols with Roche NimbleGen wash buffers. Each array was washed for 2 minutes and 15 seconds in Wash 1 at 42° C. followed by 1 min in Wash 2 at room temperature and 15 seconds in Wash 3 at room temperature. After washing, the microarrays were exposed to a stream of nitrogen gas to remove any particulates from the array surface. Microarrays were scanned on a microarray scanner (MS200 microarray scanner, Roche NimbleGen) at a resolution of 2 µM. Microarray data were analyzed using the composite likelihood maximization method (CLiMax) developed at Lawrence Livermore National Laboratory (Gardner et al., 2010). The log likelihood for each of the possible targets is estimated from the BLAST similarity scores of the array feature and target sequences, together with the feature sequence complexity and other covariates derived from the BLAST results (Gardner et al., 2010). Microarray probes with fluorescent signals that were equal to or greater than the 99% threshold of random control signals were included for CLiMax analysis. A minimum of 8 probes or at least 20% of overall probes designed against a target sequence was used as the threshold for positive detection of a target sequence.

Statistical analyses: All statistical analyses were performed using GraphPad Prism 6.00 software. Average daily gain, viremia, and area under the curve were analyzed and compared between groups using the unpaired t-test. Weekly weights were compared between groups using repeated measures analysis. Microbial families detected in feces as well as lung and lymphoid lesion scores were compared between groups using the Mann-Whitney U test. Correlation analyses were performed using Spearman rank correlation coefficients. Proportions of individual microbe species detected in each group were compared using Fisher's exact test, and the expected false discovery rate (FDR) was calculated using the Benjamini-Hochberg method to correct for multiple testing.

Results

Selection of pigs with the best and worst outcome: Clinical disease and weight gain were used as the criteria for the selection of the two groups of pigs used in the study. The time course of clinical disease after co-infection of the 95 pigs with PRRSV and PCV2 was determined. The pattern of clinical signs over time reflected the acute disease associated with PRRS followed by the later onset of PCVAD. Throughout the study period, 33 pigs (33/95; 35%) exhibited clinical signs severe enough to receive at least one day of systemic veterinary treatment. Supportive therapy was administered in the form of antibiotics and/or NSAIDS to reduce secondary bacterial infections, inflammation, and pyrexia. Seventeen of the 33 treated pigs (51.5%) died or were euthanized prior to the end of the 70 day study. Euthanasia was performed as a result of being moribund or nonresponsive to treatment. Of the 16 remaining treated pigs, 10 pigs were selected based on having the lowest ADG. The clinical signs in the 10 worst outcome pigs are summarized in Table 4. Overall, the clinical outcomes were representative of the disease syndromes associated with PRRSV and PCV2 co-infection.

TABLE 4

Summary of clinical signs in 10 pigs with the worst clinical outcome

| | Pigs Affected (%) | Duration Range (d) | Duration Mean ± SD (d) |
|---|---|---|---|
| Treatment for Clinical Signs | 100 | 10-29 | 17.5 ± 7.3 |
| Dyspnea | 100 | 3-17 | 8.9 ± 3.7 |
| Rhinorrhea | 100 | 1-15 | 5.4 ± 5.1 |
| Lethargy | 90 | 0-22 | 6.3 ± 7.8 |
| Decreased Body Condition | 80 | 0-37 | 10.8 ± 14.0 |
| Pyrexia | 80 | 0-23 | 8.3 ± 8.0 |
| Coughing | 80 | 0-11 | 2.5 ± 3.3 |
| Diarrhea | 60 | 0-14 | 2.4 ± 4.3 |
| Pallor or Jaundice | 50 | 0-5 | 1.3 ± 1.8 |
| Muscle Wasting | 30 | 0-4 | 0.9 ± 1.5 |
| Open Mouth Breathing | 30 | 0-1 | 0.3 ± 0.5 |
| Lameness | 20 | 0-22 | 2.3 ± 6.9 |
| Joint Effusion | 20 | 0-7 | 1.1 ± 2.4 |
| Aural Cyanosis | 10 | 0-2 | 0.2 ± 0.6 |

Clinical disease progression in the 10 worst outcome pigs and on the whole, mirrored the clinical disease that appeared in the entire population. Two clinical disease phases are evident post-infection. First, peaking between 10-20 dpi were clinical signs consistent with acute PRRSV infection, such as respiratory distress and aural cyanosis. Second, peaking between 32-42 dpi were clinical signs consistent with PCVAD, such as pallor or jaundice and decreased body condition. All pigs in the worst clinical outcome group showed signs of dyspnea and rhinorrhea. The majority of the worst outcome pigs showed signs of lethargy or depression, decreased body condition, pyrexia, coughing, and diarrhea. All 10 pigs received between 2-4 doses of ceftiofur and 4 pigs received between 2-6 doses of oxytetracycline. The best clinical outcome pigs did not receive antibiotics or NSAIDs during the pre and post-infection period and showed no evidence of clinical disease.

The ADG values for the 10 best and 10 worst clinical outcome pigs over the 70 day post-infection period are shown in Table 5.

TABLE 5

Average daily gain between 0-70 dpi

| Worst Performing | | Best Performing | |
|---|---|---|---|
| Pig | ADG (kg) | Pig | ADG (kg) |
| 12 | 0.149 | 30 | 0.779 |
| 50 | 0.280 | 55 | 0.797 |
| 3 | 0.492 | 43 | 0.805 |
| 47 | 0.493 | 98 | 0.808 |
| 61 | 0.495 | 29 | 0.827 |
| 16 | 0.506 | 15 | 0.831 |
| 1 | 0.537 | 62 | 0.848 |
| 28 | 0.542 | 6 | 0.883 |
| 24 | 0.555 | 63 | 0.889 |
| 88 | 0.698 | 54 | 0.903 |
| *Mean | 0.475 | *Mean | 0.837 |
| SD | 0.153 | SD | 0.042 |

*Significant difference between means, p < 0.0001, unpaired t-test

The mean ADG for the 10 worst clinical outcome group was 0.475±0.15 kg compared to 0.837±0.04 kg for the 10 best clinical outcome pigs. The difference between the means was highly significant (p<0.0001, unpaired t-test).

At the conclusion of the 70-day study period, necropsies were performed and tissues were collected from all 20 pigs.

All 10 of the worst outcome pigs had lesions consistent with PRRS, PCVAD, or virus associated immunosuppression, such as chronic polyserositis. Specifically, gross lesions in the worst outcome group included moderate to diffuse fibrous adhesions between the lungs and thoracic cavity and/or the pericardium (6 pigs), moderate interstitial pneumonia (4 pigs), multifocal fibrous adhesions in the abdomen (4 pigs), and granulomatous nephritis (1 pig). In the best clinical outcome pigs, 8 of the 10 pigs showed no significant gross lesions. In the remaining two pigs, both had multifocal fibrous adhesions in the abdomen, one had a splenic infarction, and one had diffuse fibrous adhesions on the pericardium. As summarized in Table 6, microscopic lesions were assessed in all 20 pigs through the evaluation of lung and lymph node tissues. The severity of interstitial pneumonia was significantly greater in worst performing pigs (p=0.027, Mann-Whitney U test). A similar trend occurred for worst outcome pigs in the severity of lymphoid depletion; however, this difference was not significantly different (p=0.166, Mann-Whitney U test). Overall, lesions in best performing pigs were considered mild and did not fall into the moderate or severe scoring categories (Table 6).

TABLE 6

Microscopic lung and lymph node lesions in pigs with the best and worst clinical outcome on 70 dpi with PRRSV and PCV2

| Score | No. (%) of pigs | |
|---|---|---|
| | Worst Performing | Best Performing |
| Microscopic lung lesion score[a] | | |
| 0 | 1 (10) | 3 (30) |
| 1 | 3 (30) | 6 (60) |
| 2 | 2 (20) | 1 (10) |
| 3 | 1 (10) | 0 (0) |
| 4 | 3 (30) | 0 (0) |
| Lymphoid depletion score[b] | | |
| 0 | 2 (20) | 3 (30) |
| 1 | 4 (40) | 7 (70) |
| 2 | 3 (30) | 0 (0) |
| 3 | 1 (10) | 0 (0) |

[a]Determined by evaluation of lung sections stained with hematoxylin and eosin. Scores were assigned as follows: 0, no significant lesions; 1, mild multifocal interstitial pneumonia with <50% lung lobe involvement; 2, mild to moderate multifocal interstitial pneumonia with 50 to 75% lung lobe involvement; 3, moderate to severe multifocal interstitial pneumonia with 50 to 75% lung lobe involvement; 4, severe diffuse interstitial pneumonia with >75% lung lobe involvement. Best clinical outcome pigs had significantly lower scores compared to worst clinical outcome pigs (p = 0.027, Mann-Whitney U test).
[b]Determined by evaluation of lymph node sections stained with hematoxylin and eosin. Score were assigned as follows: 0, no lymphoid depletion; 1, mild or small amount of lymphoid depletion; 2, moderate or intermediate amount of lymphoid depletion; 3, severe or large extent of lymphoid depletion. Scores were not significantly different between the two groups (p = 0.166, Mann-Whitney U test).

By the end of the study, the mean weights for the best and worst outcome groups were 72.3±3.8 kg and 43.0±11.3 kg, respectively. The 29 kg difference was statistically significant (p<0.0001, unpaired t-test). Even though the best and worst performing pigs were selected at the end of the study, the mean weights of the two groups diverged quickly after challenge and were significantly different starting at 1 week post-infection. As shown by the standard deviation bars, the mean weights in the best clinical outcome group were more uniform throughout the study period compared to the worst clinical outcome group. A regression line was fit to the mean weights for both groups over time. The greatest deviation from the estimated line appeared at between weeks 4 and 5 for the worst outcome group, which correlated with peak PCVAD.

PRRSV and PCV2 viremia: PRRSV infection in the best outcome pigs followed the typical course, peaking at between 7 and 11 dpi then followed by a decay to less than 1 log 10 copies/PCR reaction after 21 dpi. The worst clinical outcome pigs had a slight delay in viremia, peaking at around 14 dpi, but with prolonged and increased viremia throughout the remainder of the study. A significant difference between the two groups was shown on 28 dpi, when mean PRRSV viremia was 2.46 and 0.86 log 10 copies/PCR reaction for the worst and best outcome groups, respectively (p=0.015, unpaired t-test). After the initial decay, rebound peaks were observed in several pigs, a phenomenon initially described in 2010. Another way to present infection is through the calculation of virus load or the area under the viremia curve. The total viral load for each of the 20 pigs was quantified as the area under the curve (AUC) from 0 to 70 dpi (data not shown). The range for the best and worst outcome groups was 88.0-151.7 and 95.5-245.9, respectively. The means for the best and worst outcome groups were significantly different (116.2 and 153.5, respectively; p=0.04, unpaired t-test), further demonstrating that PRRS virus replication was higher in the worst outcome group.

Unlike PRRSV, PCV2 viremia shows a delay in peak replication, but is maintained at fairly high levels in the blood for an extended period of time (>3 log 10 copies/PCR reaction between 14-70 dpi for the worst clinical outcome group). Both groups showed a peak in PCV2 viremia between about 21 and 42 dpi. Even though not significantly different, the worst clinical outcome group maintained a higher peak virus level. A significant increase in PCV2 viremia for the worst outcome group was only observed on 14 dpi when mean virus levels were 3.44 and 1.74 log 10 copies/PCR reaction for the worst and best outcome groups, respectively (p=0.03, unpaired t-test). Comparing the virus loads or AUC for the two groups showed a significant increase in total PCV2 replication in the worst outcome group; means were 210.9 and 260.7 for the best and worst outcome groups, respectively (p=0.02, unpaired t-test). The range AUC values for the best and worst outcome groups were 154.8-305.5 and 187.9-350.1, respectively. Together, these data show that the amount of virus is increased in the worst outcome pigs.

DNA microarray results for serum: DNA microarray results for microbial species detected in serum, feces and lung are presented in FIGS. 11 through 14. The results for each bacterium or virus were ranked according the highest log likelihood score and the first species in each microbial family with the greatest percentage of target-specific probes is shown.

A total of 12 bacterial species were detected in serum by the microarray. Those bacteria that were only found at a low prevalence (10% or less of pigs) included Campylobacter lari, Staphylococcus haemolyticus, Frankia sp., Enterobacter sp., Enterobacter asburiae, Heliobacterium modesticaldum, and Cronobacter turicensis. The remaining bacteria are listed in FIG. 11. The results for bacteria identified Bacillus cereus as being detected at a significantly higher rate in the worst outcome pigs (7 of 10 pigs) compared to only one positive pig for the best outcome group (p=0.02, Fisher's exact test; B-H FDR=0.36). Some strains of Bacillus cereus are considered nonpathogenic but others have been implicated in cases of human foodborne illness. For viruses, all pigs showed the presence of torque teno sus virus (TTSuV) and porcine endogenous retrovirus (PERV), which are ubiquitous and were also present in the virus inoculum used for challenge.

In general, the PCR results for PRRSV and PCV2 were similar to the microarray. For example, at 70 dpi, mean PCV2 viremia was 2.3 and 3.3 log 10 copies/PCR reaction for the best clinical outcome and worst clinical outcome groups, respectively (p=0.14, unpaired t-test). The microarray detected PCV2 in the serum of 8 best outcome pigs and all 10 worst outcome pigs. The two best clinical outcome pigs negative for PCV2 on the microarray had 0 and 1.8 log 10 copies/PCR reaction, which are levels under the threshold of detection by microarray.

With regards to PRRSV, by 70 dpi, the majority of pigs showed undetectable levels of PRRSV in the blood. PRRSV was detected by microarray in only one best outcome pig and one worst outcome pig. The corresponding PCR values for those two pigs were 2.4 and 2.0 log 10 copies/PCR reaction, respectively, which is near the threshold for detection of PRRSV by microarray. The values for all other pigs were lower.

DNA microarray results for lung: Viral and bacterial species detected by microarray in lung samples are shown in FIG. 12. Only 6 species were detected with no significant differences between the two groups. The microarray detected PCV2 in all worst outcome pigs and in 8 of the best outcome pigs. By 70 dpi, PRRSV was undetectable in the lungs of all pigs. Porcine endogenous retrovirus A was detected in all pigs and torque teno sus virus was detected in 5 best outcome and 2 worst outcome pigs. Bacterial species were rare; 3 of the worst outcome pigs and 1 of the best outcome pigs had bacteria detected in lung samples.

DNA microarray results for feces: A total of 28 bacterial species were detected by the array. Those bacteria that were only found at a low prevalence (10% or less of pigs) included *Mannheimia haemolytica, Dechlorosoma suillum, Campylobacter lari, Erwinia amylovora, Brevibacillus brevis, Enterococcus faecalis, Dorea formicigenerans, Solibacillus silvestris* and *Bacteroides fragilis*. The remaining bacteria are listed in FIG. 13. Several bacteria, such as *Prevotella copri, Treponema succinifaciens, Phascolarctobacterium* sp., *Megasphaera elsdenii, Faecalibacterium prausnitzii*, and *Lactobacillus johnsonii*, were present at a relatively high prevalence; i.e. >50% of pigs. The most interesting finding was the presence of *Escherichia coli* in 5 best outcome pigs but not detected in any member of the worst outcome group (p=0.03, Fisher's exact test; B-H FDR=0.98). Although some strains of *E. coli* are enteropathogenic and cause diarrhea in piglets, there were no toxin genes detected. In serum, *Bacillus cereus* was detected at a relatively high prevalence in the worst outcome pigs (see FIG. 11); however, in the feces, the higher prevalence was in the best performing group.

Viral species detected in the feces of both groups are also shown in FIG. 13. Although these pigs were from a herd with a recent PED outbreak, PEDV was not detected by microarray in any of the pigs in the two groups. PCV2 was detected in the feces, with a higher prevalence in the worst outcome group. PRRSV was not detected. Several of the ubiquitous viruses were detected, including torque teno sus virus 1b and porcine type C retrovirus. A variety of other viruses were detected at different frequencies, including porcine kobuvirus, porcine bocavirus, porcine astrovirus, po-circo-like virus, porcine teschovirus and porcine enterovirus.

Microbiome diversity was calculated by quantifying the number of microbial families detected in each fecal sample under the defined threshold. The results are presented in FIG. 14. The range of microbial families detected for the best outcome and worst outcome groups were 10-16 and 7-12, respectively. The best clinical outcome group had significantly greater family diversity than the worst clinical outcome group (p=0.017, Mann-Whitney U-test).

Discussion

Co-infections involving PCV2 and PRRSV contribute to PCVAD, associated with significant losses through increased mortality and poor growth performance. In acute outbreaks of PCVAD in the field, the prevalence of clinically ill pigs is typically only 2-25%. In a previous study by us, co-infection with PRRSV and PCV2 resulted in 12-26% of pigs showing clinical signs of PCVAD. Thus, the majority of pigs are able to support virus replication without overt clinical disease. Understanding the factors that influence how a pig responds to virus challenge, through subclinical or clinical infections, was a primary goal of this study. Specifically, we sought to compare microbiome and pathogen load between those pigs which were classified as having the best or worst clinical outcome following co-infection with PRRSV and PCV2 in a controlled experimental trial.

The best and worst clinical outcome groups were selected based on ADG and clinical disease several weeks after virus challenge. As such, it is interesting to note that there were significant differences between the mean weights of the two groups as early as one week after challenge. However, differences between the growth rates of the two groups become most prominent during peak PCVAD. Between 28-35 dpi, mean weight gain for the worst performing group was 0.36 kg compared to 6.91 kg for the best performing group. This highlights how the development of clinical disease significantly impacts growth. Further, it is clear that some pigs can thrive while maintaining subclinical infections, even during peak virus replication and clinical disease.

When comparing PRRSV and PCV2 viremia between the two groups, it is noteworthy that primary differences were detected outside of either peak in virus replication. For example, a significant difference was found in PRRSV viremia at 28 dpi, when virus load typically decays. A significant difference was noted for PCV2 at 14 dpi, a time point prior to peak virus replication. This demonstrates that replication patterns may have a more rapid incline (PCV2) or a more gradual decline (PRRSV) in poor performing pigs. However, comparing the total virus loads allowed us to demonstrate that overall, virus replication was higher in the worst outcome group throughout the entire course of the study. This emphasizes the underlying importance of viral pathogen load in the determination of outcome after challenge.

LLMDA technology utilized in this study provides the opportunity to test for the presence of over 8000 microbes including viruses, bacteria, fungi, protozoa and archaea species. In our previous work, we confirmed the applicability of the microarray in detecting known and unknown pathogens in various diagnostic samples from pigs. In the current example, we applied the microarray to serum, lung, and fecal samples to investigate differences between groups of pigs with either the best or worst clinical outcome after co-infection. Because all pigs were co-infected, we were unable to compare results with non-challenged controls; thus, differences in microbial presence due to exposure to PRRSV and PCV2 are unknown. Overall, the DNA microarray detected the microbial signatures of 18 species in serum, 6 species in lung and 37 species in feces.

In serum, the array detected *Bacillus cereus* in a significantly greater proportion of worst outcome pigs compared to best outcome pigs. *B. cereus* can be used as a probiotic in feed (phylum Firmicutes) and this finding may represent a generalized increase in gastrointestinal permeability of poor performing pigs, allowing bacterial microbes to invade the bloodstream. Our previous microarray work also reported evidence of bacteremia, where approximately one third of pigs tested (6/18; 33%) had bacterial signatures detected in the serum.

Although pulmonary tissues were long thought of as sterile, the lung microbiome is now a well-recognized factor impacting human health and disease of the respiratory tract. In infectious diseases such as HIV and non-infectious diseases such as chronic obstructive pulmonary disease, lung microbiome profiles have been associated with treatment success or clinical outcome. The lung is a primary site for both PRRSV and PCV2 replication, and modulation of the host immune response to primary and secondary pathogens in the lung is known to increase viral pathogenesis. However, studies to investigate how the lung microbiome impacts these viral infections in swine are lacking. In the current study, very few microbes, including only two bacterial species, were detected by microarray in lung. No significant difference was detected that could help explain clinical outcome. Similarly, Schachtschneider et al. (2013) found that the microbiome present in lower respiratory tract samples from swine did not affect outcome after challenge with *Mycoplasma hyopneumoniae*, another common respiratory pathogen. The lack of pathogenic and non-pathogenic microbes detected in the lungs from our study may be due to several factors. First, the DNA microarray is less sensitive than PCR and may not detect microbes that are present in low numbers. Therefore, the microarray may not be the best tool for interrogating the porcine lung microbiome, where non-pathogenic microbes are likely present in limited quantities. Second, the timing of collection may have impacted microbe detection. At 70 days post-infection, all 20 pigs had cleared PRRSV and although many pigs still had PCV2 detected, all pigs had resolved overt clinical disease. Therefore, finding clinically relevant secondary bacterial populations in the lung would have been less likely at this time point.

Although much is still unknown, significant advances have been made in understanding the impact of the gastrointestinal microbiome on systemic and respiratory diseases in humans. Investigating the effects of the microbiome on food animal diseases is relatively new and previous studies have primarily focused on bacterial pathogens. For example, a recent study examined the fecal microbiome differences between those pigs which did and did not develop mucohemorrhagic diarrhea after inoculation with *Brachyspira hampsonii*. Pigs which developed mucohemorrhagic diarrhea were associated with lower bacterial counts in the feces and a decreased Bacteroidetes:Firmicutes ratio. Schachtschneider et al. (2013) evaluated the effects of orally administering the gastrointestinal microbiota from a healthy adult boar to nursery pigs prior to challenge with *Mycoplasma hyopneumoniae*. Oral microbial inoculation increased fecal microbiome diversity, resulted in earlier seroconversion, decreased gross lung lesions and significantly reduced coughing levels after challenge. However, there was no significant difference in weight gain between the two groups. Bearson et al. (2013) investigated the differences in fecal microbiome between those pigs which were classified as high or low *Salmonella*-shedders after experimental challenge with *Salmonella enterica* serovar *Typhimurium*. Low *Salmonella*-shedders had significantly lower levels of diarrhea, increased presence of Ruminococcaceae bacteria in the feces prior to inoculation, and increased *Prevotella* species 2 days after inoculation.

An overall trend described above and continued in our study is the association between increased fecal microbe diversity and density with improved outcome. In the current study, the total number of microbial families detected in feces was significantly higher in the best clinical outcome group. Although the worst outcome pigs had not received antibiotics for an average of 25 days prior to sample collection, reduced family diversity in the feces from this group may have been due to antibiotic treatment for clinical signs during the study period. Therefore, linear regression analysis was performed on the number of antibiotic doses received and the number of microbial families detected in feces for each of the worst outcome pigs; no significant association was detected ($p=0.81$, Spearman rank correlation; data not shown). Although there does not appear to be a significant correlation between antibiotic doses received and fecal microbial diversity, the overall effect of antibiotic administration cannot be eliminated. However, it could be expected that parenteral antibiotic therapy would affect serum and lung samples in a similar manner to feces, and reductions were not uniformly observed across all samples collected from worst outcome pigs.

Consistent with previous reports, the majority of bacterial species detected in feces by the microarray fall within the Firmicutes phylum (18/28 species). Although the ratio of Bacteroidetes:Firmicutes has been linked with both weight gain and clinical outcome, no significant ratio difference was detected between the two clinical outcome groups in this study. However, these ratios are typically calculated by quantifying relative abundance, an analysis we are unable to perform using the DNA microarray. All pigs except one had *Lactobacillus* sp. and *Faecalibacterium prausnitzii* detected in the feces. *F. prausnitzii* is a common anaerobic bacterium, considered anti-inflammatory and makes up approximately 5% of all bacteria found in human feces. In contrast, *Bacteroides* sp. was only detected in one pig, whereas it is the most prevalent bacterial genus detected in human feces. This is consistent with a previous report showing *Bacteroides* sp. are detected at a higher rate in humans than in swine. *Prevotella* sp., the most abundant bacterial genus reported in swine feces, was detected at a higher rate in best clinical outcome pigs (10/10; 100%) compared to worst clinical outcome pigs (7/9; 78%); however, this difference was not statistically significant ($p=0.21$; Fisher's exact test).

Overall, members of the Proteobacteria phylum, including *Escherichia coli*, *Erwinia amylovora*, *Campylobacter lari*, *Dechlorosoma suillum*, and *Mannheimia haemolytica*, were only detected in the best clinical outcome group feces. Specifically, *E. coli* was detected at a significantly higher rate in best outcome pigs. It should be considered that members of this phylum potentially contribute to improved clinical outcome and weight gain after co-infection. Other studies have found similar associations. For example, a significant increase in the proportion of Proteobacteria was detected in the pre-inoculation feces of pigs that remained nonclinical after *B. hampsonii* challenge. In another study, pigs administered a medicated diet known to improve feed efficiency had significant increases in bacterial species, primarily *E. coli*, of the Proteobacteria phylum compared to non-medicated pigs. *E. coli* has also been associated with excessive weight gain in pregnant women, increased body weight and fat deposition in rats, and prevention of cachexia in mice after infection with respiratory and gastrointestinal pathogens. Although this may be an undesirable outcome in studies of obesity, increased weight gain associated with *E. coli* colonization could be extremely valuable within a production system. Whether members of this bacterial phylum truly play a protective role in host response and increasing growth performance remains to be investigated.

The relationship between PCV2 and PRRSV is complex and co-infection with both viruses has been shown to increase pathogenicity compared to either virus infection alone. In the current study, the presence of high serum titers of both PRRSV and PCV2 were associated with poor clinical outcome. Although both viruses contribute to modulation of the host immune response and increase susceptibility to primary and secondary pathogens, this study highlights how host response to primary virus challenge is a major determinant of clinical outcome. In addition, this study provides valuable insight into how microbiome may contribute to outcome following systemic viral infection.

Example 3

Materials and Methods

This study was conducted as part of a project to evaluate the role of host genetics in determining the outcome following co-infection with PRRSV and PCV2; a subset of pigs from this project were included in the current study. Three week old barrows (n=50; average age 23.5±2.6 days) were obtained at weaning from a high health commercial herd negative for PRRSV. While the pigs were derived from a sow herd previously vaccinated with a PCV2 capsid subunit vaccine, the piglets were not vaccinated for PCV2 and were utilized without regards to maternal antibody. All pigs were housed in a single environmentally controlled room at the Kansas State University Large Animal Research Center under BSL-2 conditions. The piglets were randomly distributed and housed in groups of 8-10 pigs per 13.4 m² pen. All pigs were given a period of approximately 4 weeks to acclimate to their new environment prior to co-infection. Pigs were given access to food and water ad libitum.

Viruses: The PRRSV and PCV2b viral isolates used to prepare the inoculum for this study were originally derived from the lymph node of a pig with severe postweaning multisystemic wasting syndrome (PMWS) as previously described. PRRSV (isolate KS62; GenBank accession no. KM035803) was isolated by propagation on MARC-145 cells. Since wild-type PCV2b (GenBank accession no. JQ692110) does not propagate to high levels in cell culture, we took advantage of the heat stability of the virus to prepare a lymph node suspension enriched for PCV2 as previously described. The isolated PRRSV was recombined with the heat-treated PCV2 homogenate to co-infect cesarean-derived, colostrum-deprived (CD/CD) pigs. A combination lung/lymph node homogenate was prepared from the CD/CD pigs, and PRRSV and PCV2 were isolated from the homogenate by the methods described. Analysis of the inoculum yielded negative results for most heat-stable agents, but was positive for two viruses ubiquitous to swine, including Torque teno sus virus (TTSuV) and porcine endogenous retrovirus (PERVs).

PCV2b was titrated on swine testicle (ST) cells. Briefly, serial 10-fold dilutions of PCV2 challenge stock were plated in quadruplicate onto rapidly dividing ST cells in a 96-well tissue culture plate (BD Falcon). Dilutions were prepared in Eagle's minimal essential medium (EMEM; Sigma-Aldrich) supplemented with 7% fetal bovine serum (FBS; Sigma-Aldrich) and 50 µg/mL of gentamicin (Lonza). Following a 3-day incubation at 37° C. in 5% CO2, cells were fixed and permeabilized with 80% acetone. Cells were then stained with fluorescein isothiocyanate (FITC)-labeled porcine anti-PCV (Veterinary Medical Research and Development, Inc.). Infected cells were visualized using an inverted fluorescent microscope and the 50% tissue culture infectious dose ($TCID_{50}$/mL) was calculated using the method of Reed and Muench.

MARC-145 cells were used for the titration of PRRSV. Briefly, virus was serially diluted 1:10 in minimal essential medium (MEM; Corning) supplemented with 7% FBS (Sigma-Aldrich), penicillin-streptomycin (Pen Strep; 80 Units/mL and 80 µg/mL, respectively; Gibco), 3 µg/mL amphotericin B (Fungizone; Gibco), and 25 mM HEPES (Life Technologies). The dilutions were then added in quadruplicate to confluent MARC-145 cells in a 96-well tissue culture plate (BD Falcon). Following a 4-day incubation at 37° C. in 5% CO2, cells were examined for PRRSV-induced cytopathic effects. The $TCID_{50}$/mL was calculated using the method of Reed and Muench.

Experimental design and sample collection: At approximately 8 weeks of age (average age 54.5±2.6 days), all 50 pigs were infected with PRRSV and PCV2b. The viruses were recombined to yield a 2-mL dose consisting of $10^{3.6}$ $TCID_{50}$ PCV2b and $10^5$ $TCID_{50}$ PRRSV in MEM. The 2-mL dose was split, with 1 mL being delivered intranasally and 1 mL being delivered intramuscularly. Body weights of individual pigs were collected upon arrival and on 0, 7, 14, 21, 28, 35, and 42 days post-infection (dpi). Blood samples were collected from all pigs on 0, 4, 7, 11, 14, 21, 28, 35, and 42 dpi. Fecal samples were collected from all 50 pigs during the week prior to co-infection. At 35 dpi, 20 pigs were selected to represent high growth rate pigs (n=10) and low growth rate pigs (n=10). To select these two groups, the average daily gain (ADG) was calculated between 0 and 35 dpi as the change in weight over the change in time and reported in kg. Pigs in the high growth rate group had the highest ADG and pigs in the low growth rate group had the lowest ADG. The two groups were balanced according to initial weight on 0 dpi. Any pig that had overt clinical disease requiring veterinary medical treatment (as described below) was excluded from selection. At 42 dpi, all 20 pigs were humanely euthanized in accordance with the American Veterinary Medical Association Guidelines for the Euthanasia of Animals and complete necropsies were performed.

Clinical and pathologic evaluation: All pigs were assessed daily for the presence of clinical signs associated with PRRSV/PCV2 co-infection, such as dyspnea, coughing, nasal discharge, aural cyanosis, open mouth breathing, decreased body condition, muscle wasting, lethargy, depression, joint effusion, lameness, and pallor or jaundice. Pigs were visually examined by a veterinarian or veterinary assistant on each day of the study period. Under the direction of a veterinarian, appropriate treatments were administered to pigs with moderate to severe clinical disease. Examples of clinical presentations where treatment was administered included 1) dyspnea, 2) mucoid rhinorrhea, 3) lameness with joint effusion, 4) pallor or jaundice with muscle wasting, and 5) lethargy or depression with pyrexia. Clinically affected pigs were administered parenteral antibiotics, such as ceftiofur hydrochloride, oxytetracycline, or enrofloxacin. Any pig with overt clinical disease and a rectal temperature of ≥104° F. was administered parenteral flunixin meglumine, a nonsteroidal anti-inflammatory drug. For those pigs with pyrexia lasting longer than 4 days, a 2 day wash-out period was prescribed prior to the administration of oral meloxicam. Any pig with documented clinical disease requiring veterinary medical treatment was excluded from the high and low growth rate groups for this study.

At 42 dpi, all pigs were humanely euthanized with intravenous pentobarbital sodium. A board certified veterinary pathologist, blinded to the source of the pigs, performed complete necropsies and histopathology. Tissues collected included lung (1 section from each lobe) and tracheobronchial lymph node. Tissues were fixed in 10% neutral buffered formalin for at least 7 days, routinely processed in an automated tissue processor, embedded in paraffin, and stained with hematoxylin and eosin (H&E stain). Microscopic lung lesions were scored using a 0-4 system as previously described. Scores were assigned as follows: 0, no significant lung lesions; 1, mild multifocal interstitial pneumonia with <50% lung lobe involvement; 2, mild to moderate multifocal interstitial pneumonia with 50-75% lung lobe involvement; 3, moderate to severe multifocal interstitial pneumonia with 50-75% lung lobe involvement; 4, severe diffuse interstitial pneumonia with >75% lung lobe involvement. Degree of lymphoid depletion was scored using a 0-3 system as previously described. Scores were assigned as follows: 0, no lymphoid depletion; 1, mild or small amount of lymphoid depletion; 2, moderate or intermediate amount of lymphoid depletion; 3, severe or large extent of lymphoid depletion.

Measurement of PRRSV and PCV2 viremia:Viral DNA and RNA was extracted simultaneously from 50 µL of serum using Ambion's MagMAX 96 Viral Isolation Kit (Applied Biosystems) in accordance with the manufacturer's instructions. PRRS viral RNA was quantified using EZ-PRRSV MPX 4.0 Real Time RT-PCR Target-Specific Reagents (Tetracore) according to the manufacturer's instructions. For consistency, each plate contained Tetracore Quantification Standards and Control Sets for use with EZ-PRRSV MPX 4.0 RT-PCR Reagents. All PCR reactions were carried out on a CFX96 Touch Real-Time PCR Detection System (Bio-Rad) in a 96-well format using the recommended cycling parameters. The PCR assay results were reported as log 10 PRRSV RNA starting quantity (copy number) per 50 µL reaction volume.

PCV2 DNA was quantified using SsoAdvanced Universal SYBR green supermix (Bio-Rad) as previously described (Niederwerder et al., 2015; Niederwerder et al., 2016). Briefly, forward and reverse PCR primers were 5'-AATGCAGAGGCGTGATTGGA-3' (SEQ ID NO. 1) and 5'-CCAGTATGTGGTTTCCGGGT-3' (SEQ ID NO. 2), respectively, and were used at a final concentration of 300 µM. Standard curves and positive and negative controls were included on each plate. Plasmid DNA was used for the PCV2 standard curve and positive control template. DNA inserted into the plasmid was obtained from a field strain of PCV2 (PCV2b 321/393). The PCV2 PCR was carried out on a CFX96 Touch Real-Time PCR Detection System using the following settings: activation at 98° C. for 2 minutes, followed by 40 cycles of denaturing at 98° C. for 5 seconds and annealing/extension at 60° C. for 10 seconds. The PCR assay results were reported as log 10 PCV2 DNA starting quantity (copy number) per 20 µL reaction volume.

Microarray Analysis of Fecal Samples: LLMDA was designed to detect all sequenced microbes. The version 7 of the LLMDA in the 4plex 180K probe format was used to analyze the microbiome in fecal samples from this study. This version of the array targets all vertebrate infecting microbes including 3,856 viruses, 3,855 bacteria, 254 archaebacteria, 100 fungi, and 36 protozoa. The LLMDA oligonucleotide probes are around 60 nucleotides in length and were designed to detect all sequenced microbial families with a large number of probes per sequence (average of 30 probes) to improve sensitivity in the evaluation of microbial nucleic acids in a variety of samples. The high-density oligo LLMDA microarray and statistical analysis method have been extensively tested in numerous studies for viral and bacterial detection in pure or complex environmental and clinical samples.

DNA and RNA from fecal samples were extracted using the PowerViral™ Environmental RNA/DNA Isolation Kit (MO BIO, San Diego, Calif.) in accordance to the manufacturer's instructions. Briefly, for each sample approximately 0.25 g of feces was added to 600 µl of PV1 in a bead beating tube included in the PowerViral™ kit. Samples were homogenized and lysed using the vortex adaptor for the MO BIO Vortex-Genie 2 for 10 minutes at maximum speed. Samples were further purified using the manufacturer's standard protocols. All samples were eluted into 100 µl of RNase-Free water. The purified nucleic acids were quantified using the Life Technologies Qubit fluorimeter. For each sample, 10 µl of the extracted DNA and RNA was amplified using the random amplification procedure as previously described. The amplified cDNA and DNA was purified with the Qiaquick PCR purification columns (Qiagen) and quantified using the Qubit fluorometer. Between 400-500 ng of amplified cDNA and DNA were fluorescently labeled using a one-coloring labeling kit (Roche NimbleGen, Madison, Wis.) following the manufacturer's instructions.

Comparative genomic hybridization (CGH) mix was prepared in the following manner using the Agilent Technologies Oligo aCGH/ChIP-on-Chip Hybridization kit (Santa Clara, Calif.). For each sample, 10 µg of fluorescently labeled DNA was mixed with CGH mastermix, denatured at 95° C. for 3 min, and incubated at 65° C. until the arrays were ready to load. The LLMDA version 7 4×180K format microarray (Agilent Technologies Inc., Santa Clara, Calif.) was utilized for this experiment. Each sample was loaded onto the array and hybridized for 40 hr at 65° C. in a microarray rotator oven (Agilent Technologies Inc., Santa Clara, Calif.) set to a speed of 20. Microarrays were then washed using the standard manufacturer's protocol with Oligo aCGH/ChIP-on-chip Wash Buffer 1 and Oligo aCGH/ChIP-on-chip Wash Buffer 2 (Agilent Technologies Inc., Santa Clara, Calif.). The arrays were each washed in CGH Wash 1 for 5 min at room temperature, followed by CGH Wash 2 for 1 min at 37° C. Arrays were then streamed with nitrogen gas to remove particulate matter from the surface. Using the MS200 microarray scanner (Roche NimbleGen, Madison, Wis.), all arrays were scanned at a resolution of 2 µM.

Microarray data was generated from the microbe sequences at ≥99% threshold using the CLiMax method developed at Lawrence Livermore National Laboratory (Gardner et al., 2010). The log likelihood for each of the positive targets is estimated from the BLAST similarity scores of the array feature and target sequences, together with the feature sequence complexity and other covariates derived from BLAST results.

Statistical Analysis: All statistical analyses were performed using GraphPad Prism 7.01 software (La Jolla, Calif.). Mean weekly weights, ADG, and viremia were compared between groups using the unpaired t-test. Microscopic lung and lymph node lesion scores were compared between groups using the Mann-Whitney U test. Microbiome diversity and number of species within family and phylum were compared between groups using the Mann-Whitney U test. Proportions of each growth rate group with individual species and families detected were compared using Fisher's exact test.

Results

Weight gain of high and low growth rate groups diverged after co-infection: Of the 50 pigs, 10 pigs had moderate to severe clinical disease that required veterinary medical treatment (20% overall morbidity). No mortalities occurred during the 42 dpi. Thus, 40 pigs qualified for selection of the high and low growth rate groups; these pigs supported subclinical infections or had mild and transient clinical disease that did not require veterinary intervention or antibiotic treatment. ADG between 0 and 35 dpi was used as the criteria for the selection of the two groups of pigs in this study. Mean ADG for the 10 high growth rate pigs was 0.903±0.043 kg, with a range between 0.836 kg and 0.962 kg. This compares to a mean ADG for the 10 low growth rate pigs of 0.755±0.075 kg, with a range between 0.596 kg and 0.827 kg. ADG values between the two groups did not overlap. Mean ADG difference between the groups was statistically significant (p<0.0001, unpaired t-test). Mean weights upon arrival after weaning were 5.3±0.6 kg and 5.7±0.9 kg for the low and high growth rate groups, respectively (p=0.26, unpaired t-test). Mean weights continued to be similar during the acclimation period and on the day of co-infection; 19.2±2.2 kg for the low growth rate group and 19.5±1.9 kg for the high growth rate group on 0 dpi (p=0.75, unpaired t-test; FIG. 1B). No significant difference was detected between the mean weights of the two groups prior to virus infection.

After infection, the mean weights between the two groups began to diverge, initially noting a trend for absolute weight differences on 21 and 28 dpi. On 21 dpi, mean weights for the low and high growth rate groups were 33.1±4.3 kg and 36.1±2.6 kg, respectively (p=0.077, unpaired t-test). By 28 dpi, mean weights had diverged by approximately 4.4 kg; low growth rate pigs weighed an average of 38.7±4.7 kg and high growth rate pigs weighed an average of 43.1±6.1 kg (p=0.09, unpaired t-test). It was not until 35 and 42 dpi that mean weights between the high and low growth rate groups were significantly different (p=0.001 and p=0.028, respectively). Final weights on 42 dpi were 52.5±5.3 kg and 57.1±2.9 kg for the low and high growth rate groups, respectively.

High growth rate pigs had reduced PRRSV and PCV2 replication: PRRSV and PCV2 viremia were measured at 9 time points during the course of the study. Individual days as well as total virus replication were compared between the two groups. Overall, PRRS virus replication in the low growth rate group had a more rapid increase and a more prolonged decay. On 4 dpi, mean viral loads for the low and high growth rate groups were 4.1 and 3.6 log 10 copies/PCR reaction, respectively (p=0.03, unpaired t-test). Both groups had peak PRRS virus replication on 11 dpi. On 14 dpi, high growth rate pigs had a significant decline in PRRSV viremia; viral loads for low and high growth rate pigs were 4.4 and 2.8 log 10 copies/PCR reaction, respectively (0.004, unpaired t-test). A trend for reduced PRRS virus replication in the high growth rate pigs continued on 21 dpi (0.05, unpaired t-test).

PCV2 viremia followed a similar trend to PRRSV, with low growth rate pigs having a more rapid rise in viral load followed by a more gradual decline. Significant differences between the two groups were noted on days 11 and 14 post-infection. On 11 dpi, mean PCV2 loads for the low and high growth rate groups were 1.3 and 0.4 log 10 copies/PCR reaction, respectively (p=0.03, unpaired t-test). On 14 dpi, the low growth rate group continued to have an increase in mean virus load of approximately 0.73 log 10 copies/PCR reaction (p=0.019, unpaired t-test). This trend continued at 21 dpi; however, group differences were not statistically significant (p=0.086, unpaired t-test). Overall, virus replication followed a similar pattern in the two groups, peaking at 28 dpi and initiating a decay in PCV2 at 35 dpi.

Total virus replication over the 42-day study was determined by calculating the area under the viremia curve (AUC) as previously described. The PRRSV AUC ranges for the low and high growth rate groups were 83.3-115.6 and 56.0-87.7, respectively, with only a single value overlapping between the two groups. Mean PRRS viral load for the low and high growth rate groups was 98.6±8.5 and 78.3±9.9, respectively. This difference was statistically significant (p=0.0001, unpaired t-test). For PCV2, there was significant variation and a broad range of total virus load in each of the groups; 0-94.9 and 0-77.5 for the low and high growth rate pigs, respectively. Mean PCV2 AUC values were higher in low growth rate pigs; 57.6±28.5 and 35.6±22.6 for the low and high growth rate groups, respectively. However, this difference was not statistically significant (p=0.07, unpaired t-test). Taken together, this data further supports the role for pathogen load in determining the outcome after PRRSV/PCV2 co-infection.

High growth rate pigs had decreased lung lesion severity, but similar lymphoid lesions. Histopathologic lesions of tissues collected on 42 dpi were scored by a board certified pathologist blinded to the selection of pig groups. The degree of interstitial pneumonia was scored between 0-4 based on microscopic evaluation of lung tissue from each lung lobe. Mean lung lesion scores were 2.3 and 1.2 for low and high growth rate groups, respectively (p=0.05, Mann-Whitney U test). The majority of high growth rate pigs (80%) had normal lung or mild multifocal interstitial pneumonia with <50% lung lobe involvement. These data show that even when pigs are lacking in the presentation of overt clinical signs of respiratory disease, significant interstitial pneumonia may still be present.

Lymph nodes were examined for lymphocytic infiltration and for the presence of germinal centers as lymphoid depletion is essentially a pathognomonic lesion of PCVAD. Almost all pigs had some degree of lymphoid depletion, with only a single high growth rate pig having normal microscopic lymph node appearance. Although mean scores were slightly increased for low growth rate pigs (1.9 compared to 1.6 for high growth rate pigs), no significant difference was detected between the two groups (p=0.6, Mann-Whitney U test).

The microbiomes of high growth rate pigs had increased diversity, Ruminococcaceae, and Streptococcaceae, but reduced Methanobacteriaceae. The presence of microbial families and species was determined by the Microbial Detection Array. Overall, a total of 29 microbial families and 112 microbial species (data not shown) were detected by the microarray. Microbial families included 6 viral families, 1 archaea family, and 22 eubacterial families. Both DNA and RNA viruses were detected, including the families of Reoviridae, Picornaviridae, Astroviridae, Circoviridae, Parvoviridae, and Pospiviroidae. Bacterial families were detected from several phyla, including Firmicutes (10/22), Proteobacteria (6/11), Bacteroidetes (2/11), Actinobacteria (1/22), Tenericutes (1/22), Chlamydiae (1/22), and Spirochaetae (1/22).

Each of the 29 microbial families were detected at similar prevalence rates in both the high and low growth rate groups. Both groups had a 100% prevalence rate of the bacterial families Lactobacillaceae, Lachnospiraceae, Prevotellaceae, and Mycoplasmataceae. In addition, the majority of pigs in both groups had the microbial families of Astroviridae, Methanobacteriaceae, Vibrionaceae, Veillonellaceae, Ruminococcaceae, and Streptococcaceae detected. No significant difference was detected in the proportion of the two groups with each family detected (p>0.05, Fisher's exact test).

To further investigate microbiome differences between the two groups, the number of species detected within each family was compared. The greatest number of species were detected in the Lactobacillaceae family, with a mean of 5.1 and 5.8 species detected in the low and high growth rate groups, respectively; however, this difference was not statistically significant (p=0.44, Mann-Whitney U test). Three families had notable differences in the number of species detected between the two groups. First, there was a trend towards greater species diversity of the high growth rate pigs in the Streptococcaceae family; 4.2 species compared to 2.8 species detected in the low growth rate group (p=0.0998, Mann-Whitney U test). Overall, 12 Streptococcus species were detected in the feces of these pigs. Second, there was a significant decrease in the species diversity of the Methanobacteriaceae family in the high growth rate group. An average of 1.4 Methanobacteriaceae species were detected in the high growth rate pigs versus an average of 2.5 species detected in the low growth rate pigs (p=0.0086, Mann-Whitney U test). Third, an increased number of Ruminococcaceae species were detected in the high growth rate group; 1.5 species versus 1.1 species in the low growth rate group (p=0.0573, Mann-Whitney U test). This data suggests that microbiome composition at the time of virus exposure may play a role in determining outcome during co-infection. Most interestingly, species within the Streptococcaceae and Ruminococcaceae families may be beneficial to growth after co-infection whereas species within the Methanobacteriaceae family may be detrimental to growth after co-infection.

The prevalence rate of each of the 112 individual species were also compared between the two groups (data not shown). Only a single species was detected at a significantly different rate between the high and low growth rate groups. *Streptococcus equi* was detected at a significantly higher rate in high growth rate pigs; 10 and 70% of the low and high growth rate pigs, respectively, had *Strep. equi* detected (p=0.0198, Fisher's exact test). This data suggests that the presence of *Streptococcus equi* may be beneficial to weight gain during viral infection.

Although we are unable to calculate the relative abundance of bacteria in the Firmicutes and Bacteroidetes phyla using the LLMDA, we were able to evaluate the overall number of species detected within each phylum and compare these numbers between the low and high growth rate groups (data not shown). In general, the high growth rate pigs had increased numbers of Firmicutes species detected; 19.4±1.4 species vs 15.8±1.0 species for the low growth rate group (p=0.08, Mann-Whitney U test). High growing pigs also tended to have decreased species numbers detected in the Bacteroidetes phylum; 3.6±0.3 species compared to 4.1±0.4 species in the low growing pigs (p=0.34, Mann-Whitney U test). Although the differences in the current study were not statistically significant, it is interesting to consider the similarities with characteristics of the obese human microbiome, where increased Firmicutes bacteria coupled with reduced Bacteroidetes bacteria are associated with obesity.

Microbiome diversity was determined by calculating the number of families and species detected in the feces of each pig. The mean number of families detected in the low growth rate group was 13.1 with a range of 9-16 compared to a mean of 15.1 with a range of 10-18 for the high growth rate group. The difference in family diversity between the two groups was significant (p=0.0385, Mann-Whitney U test). Species diversity between the two groups followed a similar trend. The mean number of species detected in the low growth rate group was 32.7 with a range of 29-37 whereas the high growth rate group had a mean of 36.9 species with a range of 29-42. The difference in species diversity was also significant (p=0.0328, Mann-Whitney U test). Overall, high growth rate pigs had greater microbiome diversity, on both a family and species level, than low growth rate pigs. This data suggests that increased microbiome diversity may contribute to improved weight gain in pigs after co-infection.

Discussion

The current study builds on our previous work describing the microbiome profiles of best and worst clinical outcome pigs 10 weeks after co-infection with PRRSV and PCV2. The study described herein sought to investigate the microbiome characteristics prior to co-infection that may predict or predispose outcome. Second, in the current study, we included only those pigs which had not developed clinical signs warranting veterinary intervention or antibiotic treatment.

Prior to profiling the microbiome, we also investigated several other pathogenic characteristics of PRRSV/PCV2 co-infection. Perhaps the most interesting was the significant increase in virus replication of low growth rate pigs. This was surprising given the subclinical nature of disease and again emphasizes the importance of pathogen load in determining even subclinical outcomes of viral infections. Moreover, the low growth rate pigs had more severe lung lesions, with 2 low growth rate pigs having severe diffuse interstitial pneumonia. This is important to consider in a population of infected pigs, as poor growth, even in the absence of dyspnea, coughing, or nasal discharge, may be indicative of severe pulmonary pathology. Furthermore, this underscores the significant impact of subclinical infections on animal health and welfare.

At the level of the fecal microbiome, the LLMDA detected 29 microbial families and 112 microbial species, including viruses, bacteria, and archaebacteria in samples from pigs. In this study, we observed an increase in the Firmicutes:Bacteroidetes species ratio in the microbiomes of high growth rate pigs (5.6 compared to 4.2 for the low growth rate group; p=0.05, Mann-Whitney U test). The association between the relative abundance of Firmicutes to Bacteroidetes can be found in studies of human obesity. The microbiome of obese individuals has been described as having an enhanced ability to extract energy from food and is typically characterized by an increase in the abundance of the Firmicutes phylum coupled with a decrease in the abundance of the Bacteroidetes phylum. Similar to humans, obese pigs have also been described as having decreased members of the Bacteroidetes phylum when compared to lean pigs and have a positive correlation between weight gain and the Firmicutes phylum. We found similar correlations in the current study between high and low growth rate pigs, supporting a role for Firmicutes and Bacteroidetes bacteria in growth during viral infection; however, limitations to quantifying the relative abundance of microbial populations with the LLMDA should be considered.

Perhaps the most intriguing microbiome characteristic present in low growth rate pigs prior to infection was the decrease in microbiome diversity. This finding was consistent with our previous work, where pigs with the worst clinical outcome had reduced microbiome diversity at 70 dpi compared to pigs with the best clinical outcome. Reduced microbiome diversity is associated with the development of several non-infectious diseases of the respiratory tract, such as allergy and asthma, as well as the severity of infectious respiratory disease following experimental inoculation. For example, Schachtschneider et al. (2013) evaluated the effects of increasing microbiome diversity through fecal microbiota transplantation on the response of pigs to *Mycoplasma hyopneumoniae* infection. Pigs with increased microbiome diversity had a more rapid antibody response, decreased gross lung lesions, and a significant reduction in coughing compared to their non-transplanted littermates. Similar effects have been seen in mice models of human respiratory pathogens. For example, Schuijt et al. (2016) compared antibiotic-treated mice with reduced microbiome diversity to mice with endogenous microflora in response to *Streptococcus pneumoniae* infection. Mice with increased microbiome diversity had reduced *S. pneumoniae* present in lung tissue, enhanced alveolar macrophage phagocytosis, lower mortality rates, and decreased interstitial pneumonia. Taken together, microbiome diversity appears to play an advantageous role in the host response to pathogens targeting pulmonary tissues. Furthermore, microbiome diversity has proven to be beneficial in the response of pigs to 3 of the most important swine pathogens, PRRSV, PCV2 and M *hyopneumoniae*.

In addition to microbial diversity, differences in microbiome composition were also detected between high and low growth rate pigs. First, high growth rate pigs had increased species present in the Streptococcaceae family with a specific increase in the prevalence of the species *Streptococcus equi*. Other studies investigating weight gain and the swine microbiome have also found associations with members of the Streptococcaceae family. Kim et al. (2016) reported a positive correlation between the abundance of Streptococcaceae in feces and weight gain in growing pigs being fed the antibiotic growth promoter tylosin. In 2013, Pedersen et al. compared microbiome characteristics between obese and lean pigs that were either cloned or not cloned. Although Streptococcaceae was 6.3 fold higher in the terminal ileum of obese cloned pigs when compared to their lean counterparts, this finding was not consistent in samples collected from the colon. In obese cloned and non-cloned pigs, the abundance of Streptococcaceae in the colon was decreased when compared to lean pigs. Collectively, these results suggest that *Streptococcus* species may play a role in weight gain and the availability of nutrients in swine; however, this role may be dependent upon location in the gastrointestinal tract.

A second microbiome composition shift occurred within the Archaea family of Methanobacteriaceae. These archaebacteria were the only microbes detected at an overall higher prevalence rate in low growth rate pigs. Species detected within the Methanobacteriaceae family included *Methanobacterium* sp., *Methanobrevibacter ruminantium*, and *Methanobrevibacter smithii*. Similar to our findings, Luo et al. (2012) reported that lean pigs had a greater abundance and diversity of methanogens in feces when compared to obese pigs. Interestingly, methanogens have also been associated with host metabolism and several weight phenotypes in humans; however, studies have been inconsistent in their findings. For example, Million et al. (2013) found that the prevalence of *Methanobrevibacter smithii* was negatively correlated with body mass index when comparing the feces of obese, overweight, lean, and anorexic individuals in France. In contrast, Lee et al. (2011) reported that the presence and abundance of methanogens was associated with higher body mass index and waist circumference in Korean women. For cattle, sheep and goats, it is well known that methane production by methanogens in the rumen results in lost available energy from the diet. In monogastrics, however, additional research into how methanobacteria impact nutrient availability and weight gain is needed to better define their role in host metabolism.

The final microbiome composition feature associated with improved growth was the presence of increased species in the Ruminococcaceae family. Ruminococcaceae species are common gut inhabitants of both ruminants and monogastrics, considered beneficial due to a major role in cellulose digestion and the production of short-chain fatty acids. The positive correlation between Ruminococcaceae species abundance and level of dietary fiber in swine has long been. Recently, high relative abundance of the Ruminococcaceae family was associated with reduced fecal *Salmonella* shedding in pigs after infection with *Salmonella enterica* serovar *Typhimurium*. Other beneficial effects of Ruminococcaceae have been shown in chickens where improved feed conversion ratios were associated with increased caecal Ruminococcaceae abundance and in mice, where *Ruminococcus gnavus* was shown to reverse impaired growth phenotypes after transplanting the microbiota from malnourished children into germ-free mice. Due to their role in metabolism and overall gut health, increasing Ruminococcaceae species through inoculation or through fiber source may be a potential target for improving the growth of health-challenged pigs.

One finding from our initial study that was inconsistent with the current study was the increase in non-pathogenic *Escherichia coli* in the feces of pigs with improved clinical outcomes. Several study design differences may account for this discrepancy. Perhaps the most likely is timing of collection (i.e., PRRSV/PCV2 co-infection presumably shifts the microbial populations and collecting feces prior to or after viral infection would impact the microbiome). Second, pigs in the worst clinical outcome group had been treated with antibiotics. It is possible that antibiotic therapy targeted and reduced *E. coli* prevalence in pigs with poor outcomes. Nonetheless, due to the potential role of *Escherichia coli* on weight, further studies into the effects of *E. coli* on outcome after PRRSV/PCV2 co-infection are warranted.

Example 4

Materials and Methods

This example cultures and quantifies the bacteria from the original FMT material developed above.

Isolation of organisms from the original fecal microbiota transplant material:

An aliquot of the original fecal microbiota transplant (FMT) material described above was serially diluted using ten-fold dilutions from $10^{-1}$ through $10^{-5}$. Dilutions were made in microcentrifuge tubes beginning with 100 µL of the FMT material and 900 µL of sterile water. The $10^{-1}$ dilution was inoculated onto blood agar (tryptic soy agar with sheep blood). The $10^{-2}$ through $10^{-4}$ dilutions were inoculated onto blood agar, Columbia colistin naladixic acid agar with sheep blood (CNA agar), MacConkey agar, and Brucella agar with 5% sheep blood with hemin and vitamin K (Brucella agar). The $10^{-5}$ dilution was inoculated onto Brucella agar. Selective and differential media were used to aid in the generation of pure cultures and differentiation among species based on morphologic differences. Inoculated plates of blood agar, CNA agar, and MacConkey agar were incubated overnight under aerobic conditions at 37° C. with 5% CO2. Following the incubation period, all plates were examined for bacterial growth and morphologic differences among individual colonies. Colonies of each distinct morphology observed on the plates were then re-inoculated onto fresh blood agar plates for isolation. These plates were incubated as described previously.

Inoculated plates of Brucella agar were incubated overnight at 37° C. under anaerobic conditions utilizing an anaerobe container with a Mitsubishi anaerobic environment-generating sachet and anaerobic indicator. Following incubation, all plates were examined for bacterial growth and morphologic differences among colonies. Individual colonies of each unique morphology were re-inoculated onto fresh plates of Brucella agar for isolation and incubated under the same anaerobic conditions. Following overnight incubation, individual colonies from each plate were re-inoculated onto fresh plates of blood agar and incubated under aerobic conditions to determine if the isolates were facultative or obligate anaerobes.

All plates inoculated for isolation were inspected to ensure each contained a pure culture isolate. Bacterial growth from each of the pure cultures was harvested from the plates and suspended in 10 mL of sterile normal saline containing 10% glycerol. Two 500-4, aliquots were prepared from each pure culture for quantification. The remaining 9 mL of each culture was stored in a 15-mL conical tube. All tubes and vials were stored at −80° C. A total of 19 aerobic isolates and 7 anaerobic isolates were preserved in this manner. Isolates were designated A through Z. See Table 7 for the list of isolates.

Quantification of Isolates and Original FMT Material:

Quantification of each isolate was accomplished by performing ten-fold serial dilutions starting with 100 µL of the isolate in 900 µL of sterile normal saline. Dilutions from $10^{-1}$ through $10^{-10}$ were prepared. The $10^{-3}$ through $10^{-10}$ dilutions were inoculated onto blood agar for aerobic organisms (n=19) and Brucella agar for anaerobic organisms (n=7). Plates were then incubated as previously described for both aerobic and anaerobic growth conditions. All plates were examined for growth after 24 hours of incubation. Plates with insufficient growth were returned to the incubator for additional 24-hour periods up to 72 hours of total incubation. Two of the isolates failed to grow during the quantification process (X and Y). Concentration in CFU/mL for the remaining 24 isolates was calculated. Quantification calculations were based on plates containing between 30-300 colonies.

The plates inoculated with $10^{-1}$ through $10^{-5}$ dilutions of the original FMT material were used to estimate the CFU/mL of each of the isolates present in the original FMT material. This was completed by counting the number of colonies present for each distinct colony morphology present on each type of agar (blood agar, CNA agar, MacConkey agar, and Brucella agar). The CFU/mL of each individual isolate cultured in the lab was compared to the estimate of its CFU/mL in the original FMT material. For some isolates, it was necessary to prepare additional cultures in order to obtain the desired quantity of bacteria required for the cultivable bacterial therapeutic administered to pigs.

Culturing Methods Utilized to Grow Bacterial Isolates:

Concentrations of aerobic isolates O (*Streptococcus alactolyticus*) and Q (*Lactobacillus mucosae*) were inadequate from the initial growth and additional cultures were required. First, O and Q were inoculated onto blood agar plates using 100 µL of inoculum and incubated at 37° C. with 5% CO2 for 24 to 48 hours. Following incubation, bacterial growth was transferred into brain heart infusion (BHI) broth and either immediately stored or stored after a 24 hour incubation in BHI. For storage, the liquid cultures were preserved with 10% sterile glycerol and placed in −80° C. Second, O and Q were cultured directly into BHI broth from 75 µL of the original isolates. Cultures were incubated at 37° C. with 5% CO2 for 48 hours. Following incubation, the liquid cultures were preserved with the addition of 10% sterile glycerol before storing at −80° C. Quantification was performed as previously described.

Concentrations of anaerobic isolates T (*Clostridium perfringens*), V (*Clostridium perfringens*), and Z (*Bifidobacterium boum*) were inadequate from the initial growth and additional cultures were required. First, T, V and Z were inoculated onto Brucella agar using 100 µL of inoculum/plate and incubated at 37° C. with 5% CO2 for 24 to 48 hours under the anaerobic conditions described previously. Following incubation, bacterial growth was transferred to thioglycollate (FTG) broth and incubated for 24 hours. Liquid cultures were preserved with 10% sterile glycerol and stored at −80° C. Second, isolate Z was cultured in De Man, Rogosa, and Sharpe (MRS) broth in an anaerobic chamber/glove box and bench-top nitrogen gas system for 24 hours at 37° C. Culture material containing isolate Z was preserved with 10% glycerol and anaerobically stored at −80° C. in glass vials. Quantification of the isolates was performed as previously described until all isolates reached the desired concentrations.

Two anaerobic organisms identified only as a gram negative (isolate X) and gram positive (isolate Y) were unable to be cultured following their initial isolation on Brucella agar. Quantification attempts were unsuccessful when dilutions of these isolates were inoculated onto Brucella agar and incubated under two different anaerobic conditions, including the anaerobe box containing anaerobic environment-generating pouch and the anaerobic chamber/glove box.

Identification of isolates was completed using two diagnostic assays, including 1) MALDI-TOF mass spectrometry and 2) the Lawrence Livermore Microbial Detection Array (LLMDA). Together, MALDI-TOF and microarray analyses resulted in identification of 24 of the 26 isolates.

TABLE 7

Bacterial isolates cultured from fecal microbiota transplant material shown to be beneficial for prophylactic administration prior to PRRSV/PCV2 co-infection in nursery pigs*

| | | Identification | | CFU/ml |
|---|---|---|---|---|
| Growth | Isolate | MALDI-TOF | LLMDA | (FMT) |
| Aerobic | A | *Bacillus* sp. | *Bacillus amyloliquefaciens* | 2.00E+02 |
| | B | *Bacillus* sp. | *Bacillus licheniformis* | 1.00E+02 |
| | C | *Escherichia coli* | *Escherichia coli* | 1.00E+02 |
| | D | *Bacillus pumilus* | *Bacillus safensis* | 1.00E+02 |
| | E | *Escherichia coli* | *Escherichia coli* | 1.00E+03 |
| | F | *Escherichia coli* | *Escherichia coli* | 1.20E+04 |

TABLE 7-continued

Bacterial isolates cultured from fecal microbiota transplant material shown to be beneficial for prophylactic administration prior to PRRSV/PCV2 co-infection in nursery pigs*

| Growth | Isolate | Identification MALDI-TOF | LLMDA | CFU/ml (FMT) |
|---|---|---|---|---|
| | G | Escherichia coli | Escherichia coli | 1.70E+04 |
| | H | Bacillus megaterium | Bacillus sp. | 1.00E+03 |
| | I | Staphylococcus simulans | Staphylococcus carnosus | 1.00E+03 |
| | J | Escherichia coli | Escherichia coli | 5.90E+04 |
| | K | Gram negative unable to ID | Shigella sonnei | 2.00E+03 |
| | L | Enterococcus mundtii | Enterococcus mundtii | 5.00E+03 |
| | M | Enterococcus hirae | Enterococcus faecium | 1.20E+04 |
| | N | Escherichia coli | Escherichia coli | 3.70E+04 |
| | O | Streptococcus alactolyticus | Streptococcus gallolyticus | 7.30E+05 |
| | P | Enterococcus faecium | Enterococcus faecium | 1.00E+04 |
| | Q | Lactobacillus mucosae | Lactobacillus vaginalis | 1.30E+05 |
| | R | Actinomyces hyovaginalis | ND | 5.00E+04 |
| | S | Escherichia coli | Escherichia coli | 4.00E+04 |
| Anaerobic | T | Clostridium perfringens | Clostridium sp. | 2.90E+05 |
| | U | Clostridium perfringens | Clostridium sp. | 6.00E+04 |
| | V | Clostridium perfringens | Clostridium sp. | 8.00E+05 |
| | W | Clostridium perfringens | Clostridium sp. | 1.00E+05 |
| | X | Gram negative unable to ID | ND | 1.00E+05 |
| | Y | Gram positive unable to ID | ND | 4.80E+06 |
| | Z | Bifidobacterium thermophilum | Bifidobacterium indicum | 8.50E+06 |
| | Total quantity of cultivable bacteria in original FMT material | | | 1.58E+07 |

*MALDI-TOF, matrix-assisted laser desorption/ionization-time of flight mass spectrometry; LLMDA, Lawrence Livermore microbial detection array; ID, identify; ND, not determined

Example 5

Materials and Methods.

This example determined the efficacy of a cultivable bacterial microbiome therapeutic obtained from the original FMT material for improving the response of pigs to PRRSV/PCV2 co-infection over time.

High health pigs were obtained at weaning (n=100) and delivered to Kansas State University. Experimental design is shown in supplemental information page 10. The 100 pigs consisted of 50 littermate groups, each comprised of 2 sibling barrows. The 2 siblings were divided into the 2 experimental groups and balanced by weight. One group of pigs (n=50; Microbiome therapeutic) was administered the cultivable bacteria described above and the second group of pigs (n=50; Control) was administered a mock transplant with sterile saline and 10% glycerol. The cultivable bacteria was administered at a dose similar to the concentration of each species detected in the original FMT material. Microbiome therapeutic and control groups were housed in separate but identical environmentally controlled rooms and maintained under BSL-2 conditions. All pigs were housed in groups of 10 pigs/pen.

Groups were orally transplanted or mock transplanted using a flexible extended tip syringe for 7 consecutive days at a dose of 5 ml/pig/day prior to co-infection with PRRSV and PCV2d. There was no evidence of aspiration, no adverse reactions or anaphylaxis, and no diarrhea or vomiting. After 7 days of oral transplantation, all pigs in both rooms were co-infected with PRRSV and PCV2d, administered as a 2 ml dose delivered intranasally and intramuscularly. Pigs were evaluated by a veterinarian or veterinary assistant daily for clinical signs of co-infection. Blood samples and weights were collected from individual pigs either weekly or twice weekly throughout the experiment. Blood samples were tested by qPCR for viremia load. Absolute weights and average daily gain were compared between groups throughout the course of the transplantation and co-infection periods.

Pigs in both groups were serial sacrificed to evaluate the effects of the cultivable bacteria on the outcome of co-infection over time, including measurements of gross and histopathologic lesions. Two pigs from each pen were randomly selected (corresponding to sibling groups in the two rooms) on days 0, 14, and 43 post-infection for serial sacrifice and necropsy. Complete necropsies were performed by a blinded board-certified pathologist. Gastrointestinal contents were collected from several locations within the GI tract, including duodenum, ileum, cecum, colon and feces for microbial analysis and comparison between the two groups.

The goal of this study was to determine the efficacy of cultivable bacteria from the FMT material in the control of polymicrobial respiratory disease, through measurements of morbidity, mortality, lung and lymphoid lesions, virus replication, prescribed antimicrobial treatments, weight gain, antibody production, and cytokine expression at various time points after co-infection as described below in Table 8.

TABLE 8

Microbiome Therapeutic Efficacy Criteria

| Measurement | Method | Comparison to Controls | Therapeutic Success |
|---|---|---|---|
| PRRSV viremia | qPCR | −1, 3, 7, 10, 14, 21, 28, 35, 42, dpi; daily and total virus load | Significant reduction in virus replication |
| PCV2 viremia | qPCR | −1, 3, 7, 10, 14, 21, 28, 35, 42, dpi; daily and total virus load | Significant reduction in virus replication |
| PRRSV antibodies | Luminex | −1, 3, 7, 10, 14, 21, 28, 35, 42, dpi | More rapid seroconversion, increase in Ab titers, prolonged Ab production |
| PCV2 antibodies | Luminex | −1, 3, 7, 10, 14, 21, 28, 35, 42, dpi | More rapid seroconversion, increase in Ab titers, prolonged Ab production |
| Weight gain | Scale (individual Pigs) | −8, −1, 3, 7, 10, 14, 17, 21, 24, 28, 31, 35, 38, 42 dpi; absolute weights on each day, ADG post-infection | Significant increase in weight gain, increased uniformity of weights |
| Macroscopic lung lesions | Lung weight, body weight ratio, photo score to estimate % of lung affected by pneumonia | Time of euthanasia or death | Significant reduction in ratio or photo score |
| Microscopic lung lesions | Assigned a score between 0-4 based on histopathologic evaluation, degree of interstitial pneumonia | Time of euthanasia or death | Significant reduction in lung lesion scores |
| Microscopic lymphoid lesions | Assigned a score between 0-3 based on histopathologic evaluation, degree of lymphoid depletion | Time of euthanasia or death | Significant reduction in lymphoid depletion scores |
| Morbidity | Standardized health evaluations utilized to calculate prevalence of clinical signs and prescribed veterinary treatment | Daily, −8 to 44 dpi | Significant reduction in overall morbidity, prevalence of clinical signs, prescribed treatments. |
| Mortality | Pigs that die or are humanely euthanized due to severity of clinical signs or lack of response to veterinary treatment | Daily, −8 to 44 dpi | Significant reduction in mortality |

An overview of the study design is provided in FIG. 15 and results of the study are presented in FIGS. 16-21. Overall, the bacterial microbiome therapeutic appeared to be safe after administration with no adverse reactions reported, increased average daily gain of pigs during the transplantation period prior to challenge and appeared to be beneficial for growth in non-challenge conditions, resulted in a statistically significant increased average daily gain of transplanted pigs between 28-31 dpi ($p<0.1$) and 38-42 dpi ($p<0.05$) (FIG. 16), and increased the rate of PCV2 clearance in the serum of transplanted pigs. As shown in FIG. 17, PCV2 replication was lower starting around day 35 or day 36 ($p<0.05$). Mortality was decreased by 15% in the group receiving the microbiome therapeutic (FIG. 18). Table 9 provides the raw data.

TABLE 9

| Pig ID | Interstitial pneumonia (0) no lesions (1) mild and multifocal <50% lobe involvement (2) mild to moderate and multifocal 50-75% (3) moderate to severe and multifocal 50-75% (4) severe diffuse >75% | Lymph node lymphoid depletion (0) none (1) mild (small lymphocyte depletion) (2) moderate (intermediate) (3) prominent/severe (large extent) | Tracheitis (0) none (1) mild (small lymphocyte depletion) (2) moderate (intermediate) (3) prominent/severe (large extent) |
|---|---|---|---|
| 0 | 4 | 3 | 3 |
| 1 | 4 | 3 | 2 |
| 2 | 4 | 3 | 2 |
| 3 | 4 | 2 | 2 |
| 4 | 4 | 2 | 3 |
| 5 | 3 | 2 | 2 |
| 6 | 4 | 3 | 2 |
| 7 | 4 | 2 | 1 |
| 8 | 3 | 2 | 2 |
| 9 | 3 | 2 | 2 |
| 10 | 3 | 2 | 1 |
| 11 | 1 | 3 | 1 |
| 12 | 2 | 2 | 2 |
| 13 | 1 | 1 | 1 |
| 14 | 2 | 1 | 1 |
| 15 | 2 | 2 | 2 |
| 16 | 2 | 1 | 1 |
| 17 | 2 | 2 | 2 |
| 18 | 2 | 2 | 2 |
| 19 | 3 | 2 | 2 |
| 20 | 2 | 1 | 3 |
| 21 | 2 | 2 | 1 |
| 22 | 1 | 0 | 2 |
| 23 | 2 | 3 | 2 |
| 24 | 1 | 1 | 1 |
| 25 | 3 | 3 | 3 |
| 26 | 1 | 2 | 1 |
| 27 | 1 | 1 | 1 |
| 28 | 3 | 2 | NA |
| 29 | 0 | 1 | 0 |
| 30 | 0 | NA | 0 |
| 31 | 2 | 1 | 1 |
| 32 | 1 | 1 | 1 |
| 33 | 1 | 2 | 1 |
| 34 | 3 | 1 | 1 |
| 35 | 1 | 1 | 1 |
| 36 | 2 | 2 | 0 |
| 37 | 1 | 1 | 0 |
| 38 | 2 | 2 | 1 |
| 39 | 2 | 2 | 1 |
| 40 | 2 | 1 | 0 |
| 41 | 4 | 3 | 1 |
| 42 | 0 | 0 | 0 |
| 43 | 1 | 2 | 1 |
| 44 | 2 | 2 | 2 |
| 45 | 1 | 0 | 0 |
| 46 | 4 | 3 | 3 |
| 47 | 4 | 3 | 1 |
| 48 | 2 | 2 | 1 |
| 49 | 2 | 1 | 1 |
| 50 | 2 | 0 | 1 |
| 51 | 2 | 1 | 1 |
| 52 | 4 | 3 | 1 |
| 53 | 2 | 2 | 1 |
| 54 | 1 | 1 | 0 |
| 55 | 1 | 1 | 0 |
| 56 | 4 | 3 | 1 |
| 57 | 3 | 2 | 0 |
| 58 | 4 | 3 | 1 |
| 59 | 3 | 3 | 1 |
| 60 | 4 | 3 | 2 |
| 61 | 3 | 1 | 0 |
| 62 | 1 | 0 | 0 |
| 63 | 2 | 2 | 2 |
| 64 | 4 | 4 | 3 |
| 65 | 2 | 1 | 1 |
| 66 | 0 | 0 | 0 |
| 67 | 3 | 1 | 2 |
| 68 | 4 | 3 | 1 |
| 69 | 3 | 2 | 1 |

TABLE 9-continued

| Pig ID | Interstitial pneumonia (0) no lesions (1) mild and multifocal <50% lobe involvement (2) mild to moderate and multifocal 50-75% (3) moderate to severe and multifocal 50-75% (4) severe diffuse >75% | Lymph node lymphoid depletion (0) none (1) mild (small lymphocyte depletion) (2) moderate (intermediate) (3) prominent/severe (large extent) | Tracheitis (0) none (1) mild (small lymphocyte depletion) (2) moderate (intermediate) (3) prominent/severe (large extent) |
|---|---|---|---|
| 70 | 3 | 2 | 1 |
| 71 | 2 | 1 | 1 |
| 72 | 3 | 3 | 1 |
| 73 | 4 | 3 | 2 |
| 74 | 3 | 2 | 1 |
| 75 | 4 | 3 | 2 |
| 76 | 3 | 3 | 2 |
| 77 | 4 | 3 | 0 |
| 78 | 0 | 0 | 0 |
| 79 | 2 | 2 | 0 |
| 80 | 2 | 1 | 1 |
| 81 | 0 | 0 | 0 |
| 82 | 2 | 1 | 0 |
| 83 | 3 | 2 | 1 |
| 84 | 2 | 2 | 1 |
| 85 | 4 | 2 | 1 |
| 86 | 2 | 1 | 0 |
| 87 | 1 | 0 | 1 |
| 88 | 3 | 2 | 1 |
| 89 | 2 | 2 | 0 |
| 90 | 3 | 3 | 0 |
| 91 | 4 | 2 | 1 |
| 92 | 3 | 2 | 1 |
| 93 | 2 | 1 | 0 |
| 94 | 3 | 3 | 1 |
| 95 | 2 | 1 | 0 |
| 96 | 3 | 2 | 1 |
| 97 | 1 | 0 | 1 |
| 98 | 1 | 2 | 1 |
| 99 | 1 | 1 | 0 |

CONCLUSION

Infection with PRRSV and/or PCV2 results in significant production losses to the swine industry. In this study, both microbiome diversity and composition were associated with response to co-infection with PRRSV and PCV2, including lung pathology, virus replication, and growth rate. Microbiome characteristics of high growth rate pigs included increased diversity, decreased Methanobacteriaceae, increased Streptococcaceae, and increased Ruminococcaceae. Modulating the piglet microbiome to have one or more of these characteristics may be an alternative tool for control of disease associated with PRRSV and PCV2.

I claim:

1. A method of reducing the incidence of or severity of clinical signs associated with or caused by a pathogen known to cause respiratory infections comprising the step of:
    administering at least one dose of a composition comprising a quantity of at least one bacteria selected from the group consisting of *Bacillus* sp., *Clostridium* sp., *Escherichia* sp., *Staphylococcus* sp., *Shigella* sp., *Enterococcus* sp., *Streptococcus* sp., *Lactobacillus* sp., *Bifidobacterium* sp., *Actinomyces* sp., and any combination thereof, wherein the at least one bacteria is sourced from the gut of a healthy individual; and
    a component selected from the group consisting of a prebiotic, preservative, stabilizer, antibiotic, or any combination thereof to an animal in need thereof, wherein the composition is administered at a time selected from the group consisting of 1-2 days after birth, up to or at the time of weaning, after weaning in the early nursery period, and any combination thereof, and
    wherein the composition is administered more than once to a pig in need thereof.

2. The method of claim 1, wherein said composition includes at least 2 log CFU/ml/dose of said bacteria.

3. The method of claim 1, wherein said composition includes between 2-10 bacteria species.

4. The method of claim 1, wherein the composition is administered at a time selected from the group consisting of 1-2 days after birth, up to or at the time of weaning, after weaning in the early nursery period, after the presence of a pathogen is discovered in a herd or group of animals, on a repeated basis to members of the group used for breeding purposes, and any combination thereof.

5. The method of claim 1, wherein said clinical signs are selected from the group consisting of dyspnea, aural cyanosis, coughing, nasal discharge, open mouth breathing, poor body condition, muscle wasting, pallor or jaundice, lameness, joint effusion, depression, lethargy, and any combination thereof.

6. The method of claim 1, wherein said clinical signs are reduced by at least 10% in comparison to an animal or group of animals that did not receive an administration of the composition.

7. The method of claim 1, wherein the composition is administered via a bolus, chewable product, oral drench, nasal drench, placement on feed, placement in water, or placed on the mammary gland of a sow for subsequent consumption by suckling animals.

8. The method of claim 1, wherein the bacteria is selected from the group consisting of *Bacillus amyloliquefaciens*, *Bacillus licheniformis*, *Escherichia coli*, *Bacillus safensis*, *Staphylococcus carnosus*, *Shigella sonnei*, *Enterococcus mundtii*, *Enterococcus faecium*, *Streptococcus gallolyticus*, *Enterococcus faecium*, *Lactobacillus vaginalis*, *Bifidobacterium indicum*, *Bacillus pumilus*, *Bacillus megaterium*, *Staphylococcus simulans*, *Enterococcus hirae*, *Streptococcus alactolyticus*, *Lactobacillus mucosae*, *Actinomyces hyovaginalis*, *Clostridium perfringens*, *Bifidobacterium thermophilum*, and any combination thereof.

9. The method of claim 1, wherein the composition comprises at least $1.00 \times 10^2$ of the at least one bacterium.

10. A method of reducing the incidence of or severity of clinical signs associated with or caused by a pathogen known to cause respiratory infections and being selected from the group consisting of Porcine Circovirus Type 2 (PCV2), Porcine Reproductive and Respiratory Syndrome Virus (PRRSV), *Mycoplasma* hyopneumonia, swine influenza, and any combination thereof, wherein the method comprises the step of:
    administering at least one dose of a composition comprising a quantity of at least one bacteria selected from the group consisting of *Bacillus* sp., *Clostridium* sp., *Escherichia* sp., *Staphylococcus* sp., *Shigella* sp., *Enterococcus* sp., *Streptococcus* sp., *Lactobacillus* sp., *Bifidobacterium* sp., *Actinomyces* sp., and any combination thereof, wherein the at least one bacteria is sourced from the gut of a healthy individual; and a component selected from the group consisting of a prebiotic, preservative, stabilizer, antibiotic, or any combination thereof to an animal in need thereof, wherein the composition is administered at a time selected from the group consisting of 1-2 days after birth, up to or at the time of weaning, after weaning in the early nursery period, and any combination thereof.

11. The method of claim 10, wherein said composition is in a form selected from the group consisting of a bolus, a chewable product, oral drench, nasal drench, combined or placed on feed, placed in water, or any combination thereof.

12. The method of claim 10, wherein the composition is administered more than once to a pig in need thereof.

13. The method of claim 10, wherein said composition includes at least 2 log CFU/ml/dose of said bacteria.

14. The method of claim 10, wherein the said composition includes between 2-10 bacterial species.

15. The method of claim 10, wherein said clinical signs are selected from the group consisting of dyspnea, aural cyanosis, coughing, nasal discharge, open mouth breathing, poor body condition, muscle wasting, pallor or jaundice, lameness, joint effusion, depression, lethargy, and any combination thereof.

16. The method of claim 10, wherein said clinical signs are reduced by at least 10% in comparison to an animal or group of animals that did not receive an administration of the composition.

17. The method of claim 10, wherein the composition comprises at least $1.00 \times 10^2$ of the at least one bacterium.

* * * * *